(12) United States Patent
Oballa et al.

(10) Patent No.: US 6,525,036 B2
(45) Date of Patent: Feb. 25, 2003

(54) COMPOUNDS AND COMPOSITIONS AS PROTEASE INHIBITORS

(75) Inventors: Renata Marcella Oballa, Kirkland (CA); Petpiboon Prasit, Pierrefonds (CA); Joel Stephane Robichaud, Dollard des Ormeaux (CA); Elise Isabel, Pointe-Claire (CA); Eduardo Setti, San Mateo, CA (US); Dan-Xiong Wang, Foster City, CA (US); Rohan V. Mendonca, South San Francisco, CA (US); Shankar Venkatraman, Pleasanton, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/754,962

(22) Filed: Jan. 5, 2001

(65) Prior Publication Data

US 2002/0052378 A1 May 2, 2002

Related U.S. Application Data

(60) Provisional application No. 60/174,978, filed on Jan. 6, 2000, and provisional application No. 60/256,793, filed on Dec. 19, 2000.

(51) Int. Cl.$^7$ .................. A61K 31/277; C07C 253/00
(52) U.S. Cl. ............ 514/112; 514/521; 514/238.5; 514/352; 514/357; 544/168; 544/336; 544/344; 544/366; 544/389; 544/393; 544/400; 546/17; 546/133; 546/175; 546/231; 546/330; 548/214; 548/253; 548/336.1; 548/455; 548/484; 558/384; 558/386; 558/392
(58) Field of Search ............... 546/308, 337; 514/352, 357, 238.5, 521, 112; 544/165; 558/392, 384, 386

(56) References Cited

U.S. PATENT DOCUMENTS

6,075,055 A    6/2000  Masuda et al. ............ 514/619
6,140,358 A   10/2000  Lieb et al. ................ 514/425

FOREIGN PATENT DOCUMENTS

WO    WO 9638406 A1 * 12/1996
WO    WO0048992        8/2000
WO    WO0049008        8/2000

OTHER PUBLICATIONS

DuFour, et al., *Engineering Nitrile Hydratase Activity in a Cysteine Protease by a Single Mutation*; Biochemistry, vol. 34, No. 50, 1995, pp. 16382–16388.
Gour–Salin et al., *Inhibition of papain by peptide nitriles: conversion of the nitrile group into other functionalities via the papain:nitrile thioimidate ester adduct*; Can J. Chem., vol. 69, 1991, pp. 1288–1297.
Hanzlik et al., *Reversible covalent binding of peptide nitriles to papain*; Biochimica et Biophysica Acta, vol. 1035; 1990; pp. 62–70.
Lipshutz et al., *Heterocycles as Masked Diamide/Dipeptide Equivalents. Formation and Reactions of Substituted 5–(Acylamino)oxazoles as Intermediates en route to the Cyclopeptide Alkaloids*; J. Am. Chem. Soc., vol. 105, No. 26, 1983; pp. 7703–7713.
McMath et al., *Direct dialkylation of peptide nitriles. Application to the synthesis of 1–aminocyclopropane–1–carboxylic acid (Acc)–containing dipeptides*; Bull Soc. Chim Fr., vol. 134, 1997; pp. 105–110.
Picken et al., *Inhibition of bovine cathepsin B by amino acid–derived nitriles*; Biochemical Society Transactions, 1990; p. 316.
Suzue et al., *Studies on Hepatic Agents. I. Synthesis of Aminoacyl (and Hydroxyacyl) Aminoacetonitriles*; Chem. Pharm. Bull., vol. 16, No. 8; Aug. 1968, pp. 1417–1432.
Vargha, *Noi Derivati Peptidici (VI) Di–si tripeptidonitrili N–protejati*; Studio Universitatis Babes–Bolgai. Series Chiemia, vol. 13, No. 2, 1968; pp. 31–35.

* cited by examiner

Primary Examiner—Richard L. Raymond
(74) Attorney, Agent, or Firm—Nicole M. Wallinger; Mark R. Daniel

(57) ABSTRACT

The present invention relates to novel cysteine protease inhibitors of Formula I:

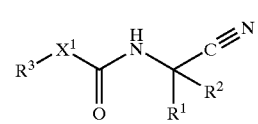

the pharmaceutically acceptable salts and N-oxide derivatives thereof, their use as therapeutic agents and methods of making them.

25 Claims, No Drawings

COMPOUNDS AND COMPOSITIONS AS PROTEASE INHIBITORS

The present application is based on and claims priority from U.S. Provisional Patent Applications No. 60/174,978, filed Jan. 6, 2000, and No. 60/256,793, filed Dec. 19, 2000.

THE INVENTION

This application relates to compounds and compositions for treating diseases associated with cysteine protease activity, particularly diseases associated with activity of cathepsins B, K, L or S.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteo arthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in osteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis. In addition, cathepsin S is implicated in: allergic disorders, including, but not limited to asthma; and allogenic immune responses, including, but not limited to, rejection of organ transplants or tissue grafts.

In view of the number of diseases wherein it is recognized that an increase in cysteine protease activity contributes to the pathology and/or symptomatology of the disease, molecules which are shown to inhibit the activity of this class of enzymes, in particular molecules which are inhibitors of cathepsins B, K, L and/or S, will be useful as therapeutic agents.

SUMMARY OF THE INVENTION

This Application relates to compounds of Formula I:

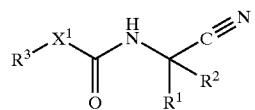

in which:
X$^1$ is selected from a group consisting of —CR$^4$R$^5$—, —CR$^6$R$^7$— and —NR$^7$—, wherein:
R$^4$ and R$^5$ along with the carbon atom to which they are attached represents

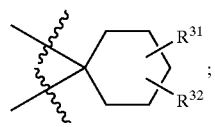

where
R$^{31}$ and R$^{32}$ independently represent hydrogen or hydroxy, alternatively R$^{31}$ and R$^{32}$ can be taken together to represent an oxo (=O) group;
R$^6$ is hydrogen or (C$_{1-6}$)alkyl; and
R$^7$ is (C$_{1-8}$)alkyl or (CH$_2$)$_{1-3}$ cyclopropyl;
R$^1$ is hydrogen or (C$_{1-6}$)alkyl;
R$^2$ is selected from a group consisting of hydrogen and R$^{2a}$; alternatively R$^1$ and R$^2$ together represent C$_{2-5}$ alkylene or —CH$_2$NR$^8$CH$_2$—, or both R$^1$ and R$^2$ simultaneously represent fluoro;
R$^{2a}$ represents (C$_{1-8}$) alkyl optionally substituted with a group selected from —NR$^8$R$^{35}$, —NR$^8$C(O)R$^{35}$, —NR$^8$C(O)OR$^{35}$, —NR$^8$C(O)NR$^8$R$^{35}$, —NR$^8$C(NR$^8$)NR$^8$R$^{35}$, —OR$^{35}$, —SR$^{35}$, —S(O)R$^{35}$, —S(O)$_2$R$^{35}$, —C(O)R$^{35}$, —C(O)OR$^{35}$, —OC(O)R$^{35}$, —C(O)NR$^8$R$^{35}$, —OC(O)NR$^8$R$^{35}$, —S(O)$_2$NR$^8$R$^{35}$, —P(O)(OR$^8$)OR$^{35}$, —OR$^{52}$, —CONR$^8$R$^{52}$, —SO$_2$NR$^8$R$^{52}$ and —OP(O)(OR$^8$)OR$^{35}$;
R$^{35}$ is selected from a group consisting of (C$_{1-4}$)alkyl, —(CH$_2$)$_{0-3}$(C$_{3-12}$)cycloalkyl, —CH$_2$)$_{0-3}$hetero(C$_{5-10}$)cycloalkyl, —(CH$_2$)$_{0-3}$(C$_{6-10}$)aryl, —CH$_2$)$_{0-3}$hetero(C$_{5-10}$)aryl, —(CH$_2$)$_{0-3}$(C$_{9-10}$)bicycloaryl and -(CH$_2$)$_{0-3}$hetero(C$_{8-10}$)bicycloaryl;
R$^3$ is selected from a group consisting of (C$_{6-10}$)aryl, (C$_{3-10}$)cycloalkyl, (C$_{3-10}$)heterocycloalkyl, hetero(C$_{5-10}$)aryl, (C$_{9-10}$)bicycloaryl and hetero(C$_{8-10}$)bicycloaryl, wherein:
R$^3$ may be substituted further by a radical selected from a group consisting of —X$^3$NR$^8$R$^{21}$, —X$^3$NR$^8$C(O)R$^{21}$, —X$^3$NR$^8$C(O)OR$^{21}$, —X$^3$NR$^8$C(O)NR$^8$R$^{21}$, —X$^3$NR$^8$C(NR$^8$)NR$^8$R$^{21}$, —X$^3$OR$^{21}$, —X$^3$SR$^{21}$, —X$^3$S(O)R$^{21}$, —X$^3$S(O)$_2$R$^{21}$, —X$^3$C(O)R$^{21}$, —X$^3$C(O)OR$^{21}$, —X$^3$OC(O)R$^{21}$, —X$^3$C(O)NR$^8$R$^{21}$, —X$^3$OC(O)NR$^8$R$^{21}$, —X$^3$S(O)$_2$NR$^8$R$^{21}$, —X$^3$P(O)(OR$^8$)OR$^{21}$, —X$^3$OR$^{52}$, —X$^3$CONR$^8$R$^{52}$, —X$^3$SO$_2$NR$^8$R$^{52}$, —X$^3$OP(O)(OR$^8$)OR$^{21}$ and —R$^{21}$, wherein:
X$^3$ is a bond or (C$_{1-6}$)alkylene, R$^8$ at each occurrence independently is hydrogen or (C$_{1-6}$)alkyl, R$^{52}$ represents —CH$_2$CH$_2$—N(CH$_2$CH$_2$OH)$_2$, —CH(CH$_3$)CH$_2$N(CH$_3$)$_2$, —CH$_2$CH$_2$OH, —CH$_2$CH$_2$N(CH$_3$)$_2$ or —CH$_2$CN, and R$^{21}$ is —(C$_{1-8}$)alkyl or —X³R²², wherein X³ is as defined above and R²² is selected from a group consisting of $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl, wherein:

R²² may be substituted further by a radical selected from a group consisting of —X³NR⁸R²³, —X³NR⁸C(O)R²³, —X³NR⁸C(O)OR²³, —X³NR⁸C(O)NR⁸R²³, —X³OR²³, —X³NR⁸C(NR⁸)NR⁸R²³, —X³SR²³, —X³S(O)R²³, —X³S(O)₂R²³, —X³C(O)R²³, —X³OC(O)R²³, —X³C(O)OR²³, —X³C(O)NR⁸R²³, —X³OC(O)NR⁸R²³, —X³S(O)₂NR⁸R²³, —X³OR⁵², —X³CONR⁸R⁵², —X³SO₂NR⁸R⁵², —X³P(O)(OR⁸)OR²³, —X³OP(O)(OR⁸)OR²³ and —R²³, wherein:

X³ is a bond or $(C_{1-6})$alkylene and R⁸ at each occurrence independently is hydrogen or $(C_{1-6})$alkyl, R⁵² represents CH₂CH₂—N(CH₂CH₂OH)₂, CH(CH₃)CH₂N(CH₃)₂, CH₂CH₂OH, CH₂CH₂N(CH₃)₂ or CH₂CN, and R²³ is $(C_{1-8})$alkyl or —X³R²⁴, wherein X³ is as defined above and R²⁴ is selected from a group consisting of $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl, wherein R²⁴ may be substituted further by a radical selected from a group consisting of —X³NR⁸R²⁵, —X³NR⁸C(O)R²⁵, —X³NR⁸C(O)OR²⁵, —X³OR²⁵, —X³NR⁸C(O)NR⁸R²⁵, —X³NR⁸C(NR⁸)NR⁸R²⁵, —X³SR²⁵, —X³S(O)R²⁵, —X³S(O)₂R²⁵, —X³C(O)R²⁵, —X³OC(O)R²⁵, —X³C(O)OR²⁵, —X³C(O)NR⁸R²⁵, —X³OC(O)NR⁸R²⁵, —X³S(O)₂NR⁸R²⁵, —X³P(O)(OR⁸)OR²⁵, —X³OR⁵², —X³CONR⁸R⁵², —X³SO₂NR⁸R⁵², —X³OP(O)(OR⁸)OR²⁵ and —R²⁵, wherein:

X³ is a bond or $(C_{1-6})$alkylene and R⁸ at each occurrence independently is hydrogen or $(C_{1-6})$alkyl, R⁵² represents —CH₂CH₂—N(CH₂CH₂OH)₂, —CH(CH₃)CH₂N(CH₃)₂, —CH₂CH₂OH, —CH₂CH₂N(CH₃)₂ or —CH₂CN, and R²⁵ is —$(C_{1-8})$alkyl or —X³R²⁶, wherein X³ is as defined above and R²⁶ is selected from a group consisting of $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl; wherein any of the $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl contained within R³, R²², R²⁴ and R²⁶ may be substituted further with up to five substituents selected from a group consisting of $(C_{1-6})$alkyl, $(C_{1-6})$alkylidene, cyano, halo, nitro, halo-substituted $(C_{1-3})$alkyl, —X³NR¹⁶R¹⁶, —X³NR¹⁶C(O)OR¹⁶, —X³NR¹⁶C(O)NR¹⁶R¹⁶, —X³NR¹⁶C(NR¹⁶)NR¹⁶R¹⁶, —X³OR¹⁶, —X³SR¹⁶, —X³C(O)OR¹⁶, —X³C(O)NR¹⁶R¹⁶, —X³S(O)₂NR¹⁶R¹⁶, —X³P(O)(OR⁸)OR¹⁶, —X³OR⁵², —X³CONR⁸R⁵², —X³C(O)R¹⁶, —X³SO₂NR⁸R⁵², —X³S(O)R¹⁷, —X³OP(O)(OR⁸)OR¹⁶, —X³NR¹⁶C(O)R¹⁷, —X³S(O)₂R¹⁷ and —X³C(O)R¹⁶, wherein:

X³ is a bond or $(C_{1-6})$alkylene, R⁵² represents —CH₂CH₂—N(CH₂CH₂OH)₂, —CH(CH₃)CH₂N(CH₃)₂, —CH₂CH₂OH, —CH₂CH₂N(CH₃)₂ or —CH₂CN, R¹⁶ at each occurrence independently is selected from a group consisting of hydrogen, $(C_{1-3})$alkyl or halo-substituted $(C_{1-3})$alkyl and R¹⁷ is —$(C_{1-3})$alkyl or halo-substituted $(C_{1-3})$alkyl; and the N-oxide derivatives, prodrug derivatives, protected derivatives, individual stereo isomers and mixtures of stereo isomers, and pharmaceutically acceptable salts thereof, with the proviso that only one of R³, R²², R²⁴ and R²⁶ represents a fused bicyclic ring structure.

A second aspect of this invention is a pharmaceutical composition that contains a compound of Formula I or a N-oxide derivative, prodrug derivative, individual isomer or mixture of isomers or a pharmaceutically acceptable salt thereof in admixture with one or more suitable excipients.

A third aspect of this invention is a method of treating a disease in an animal in which inhibition of a cysteine protease can prevent, inhibit or ameliorate the pathology and/or symptomatology of the disease. Said method comprises administering to the animal a therapeutically effective amount of compound of Formula I or a N-oxide derivative, prodrug derivative, individual isomer or mixture of isomers or a pharmaceutically acceptable salt thereof.

A fourth aspect of this invention is the processes for preparing compounds of Formula I and the N-oxide derivatives, prodrug derivative, protected derivatives, individual isomers and mixtures of isomers, and the pharmaceutically acceptable salts thereof as set forth in "Detailed Description of the Invention".

DETAILED DESCRIPTION OF THE INVENTION

Definitions

Unless otherwise stated, the following terms used in the specification and claims are defined for the purposes of this Application and have the meanings given this Section:

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by straight or branched chain arrangement of the constituent carbon atoms and may be saturated or partially unsaturated with two or more double or triple bonds.

"Alkyl" represented by itself means a straight or branched, saturated or unsaturated, aliphatic radical having the number of carbon atoms indicated (e.g., $(C_{1-6})$alkyl includes methyl, ethyl, propyl, 2-methylpropyl, butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means a bond (e.g., $(C_{6-10})$aryl$(C_{0-6})$alkyl includes phenyl, benzyl, phenethyl, 1-phenylethyl 3-phenylpropyl, and the like). An alkyl group can be substituted with one or more groups selected from —NH₂, —NH(CH₃)$_{1-4}$, —N[(CH₃)$_{1-4}$]₂, —OH and —OCH₃.

"Alkylene", unless indicated otherwise, means a straight or branched, saturated or unsaturated, aliphatic, divalent radical having the number of carbon atoms indicated (e.g., $(C_{2-5})$alkylene includes ethylene (—CH₂CH₂— or —CH(CH₃)—), 1-methylethylene (—CH(CH₃)CH₂—), trimethylene (—CH₂CH₂CH₂—), tetramethylene (—CH₂CH₂CH₂CH₂—), pentamethylene (—CH₂CH₂CH₂CH₂CH₂—), and the like). Thus, a compound of Formula I in which R¹ together with R² forms pentamethylene is depicted by the following illustration:

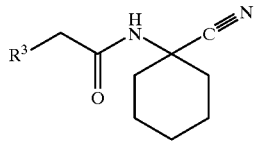

wherein R¹, R² and R³ are as defined in the Summary of the Invention.

"Alkylidene" means a straight or branched saturated or unsaturated, aliphatic, divalent radical having the number of carbon atoms indicated (e.g., ($C_{1-6}$)alkylidene includes methylene ($CH_2$), ethylidene ($CHCH_3$), isopropylidene ($C(CH_3)_2$), propylidene ($CHCH_2CH_3$), allylidene (CHCH $CH_2$), and the like).

"Amino" means the radical —$NH_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, non-human primates such as monkeys, apes, etc., or the like) and non-mammals (e.g., birds, or the like).

"Aromatic" means a moiety wherein the constituent atoms make up an unsaturated ring system, all atoms in the ring system are sp2 hybridized and the total number of pi electrons is equal to 4n+2.

"Aryl" means a monocyclic or fused bicyclic aromatic ring assembly containing the total number of ring carbon atoms indicated. For example, optionally substituted ($C_{6-10}$) aryl as used in this Application includes phenyl, 3-bromophenyl, 3-carbamoylphenyl, 4-carbamoylphenyl, 3-[2-(1-methylpyrrolidin-2-yl)-ethoxycarbonylamino] phenyl, morpholin-4-ylcarbonylmethyl, 3-(2-morpholin-4-ylethoxycarbonylamino)phenyl, 3-[3-(3-morpholin-4-ylpropyl)ureido]phenyl, naphth-1-yl, naphth-2-yl, 3-nitrophenyl, 4-nitrophenyl, 2-methoxyphenyl, 4-methoxyphenyl, 3-phenoxyphenyl, 4-phenoxyphenyl, phenyl, 4-(3-pyrid-3-ylmethylureido)phenyl, 4-(3-pyrid-4-ylmethylureido)phenyl, 3-pyrid-3-ylphenyl, 4-(3-pyrid-4-ylureido)phenyl, 4'-sulfamoylbiphenyl-3-yl, 3-thien-3-ylphenyl, and the like.

"Bicycloaryl" means a bicyclic ring assembly containing the number of ring carbon atoms indicated, wherein the rings are fused and one, but not both, of the rings comprising the assembly is aromatic, and any carbocyclic ketone, thioketone or iminoketone derivative thereof (e.g., ($C_{9-10}$) bicycloaryl includes 1,2-dihydronaphthyl, 5,6,7,8-tetrahydronaphth-1-yl, 2,4-dioxo-1,2,3,4-tetrahydronaphthyl, indanyl, indenyl, 1,2,3,4-tetrahydronaphthyl, and the like).

"Carbamoyl" means the radical —$C(O)NH_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carbocyclic ketone, thioketone or iminoketone derivative" means an alicyclic derivative wherein one or more ring members are substituted by an oxo (=O), thioxo (=S) or imino (=NR) group, wherein R is hydrogen, ($C_{1-6}$)alkyl or a protecting group (e.g., 1-oxoindan-5-yl, 3-thioxocyclohexyl, 5-iminopiperidin-3-yl, and the like).

"Carboxy" means the radical —C(O)OH. Unless indicated otherwise, the compounds of the invention containing carboxy moieties include protected derivatives thereof. Suitable protecting groups for carboxy moieties include benzyl, tert-butyl, and the like.

"Cycloalkyl" means a saturated or partially unsaturated, monocyclic ring, or bridged polycyclic ring assembly containing the number of ring carbon atoms indicated, and any carbocyclic ketone, thioketone or iminoketone derivative thereof (e.g., ($C_{3-10}$)cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like).

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" means fluoro, chloro, bromo or iodo. "Heteroaryl" means aryl, as defined in this Application, provided that one or more of the ring carbon atoms indicated are replaced by a hetero atom moiety selected from N, NR, O or S, wherein R is hydrogen, ($C_{1-6}$)alkyl or a protecting group, and each ring is comprised of 5 or 6 ring atoms. For example, optionally substituted hetero($C_{5-10}$)aryl as used in this Application includes 4-(3-aminophenyl)thiazol-2-yl, 3-(6-aminopyrid-3-yl)phenyl, 2-dimethylaminothiazol-4-yl, 3-(4,6-dimethylpyrid-2-yl)phenyl, 6-methoxypyrid-3-yl, 2-(4-morpholin-4-ylphenyl)thiazol-4-yl, 4-(3-nitrophenyl) thiazol-2-yl, 2-phenylthiazol-4-yl, 4-phenylthiazol-2-yl, pyrid-2-yl, pyrid-3-yl, pyrid-4-yl, 2-pyrid-4-ylaminothiazol-4-yl, 3-pyrid-2-ylphenyl, 3-pyrid-3-ylphenyl, 3-pyrid-4-ylphenyl, 2-pyrid-4-ylthiazol-4-yl, 4-pyrid-4-ylthiazol-2-yl, 4-(4-pyrrolidin-1-ylphenyl)thiazol-2-yl, thien-2-yl, thien-3-yl, thien-2-ylphenyl, thiazol-2-ylphenyl, 6-bromopyrid-2-ylphenyl, 6-bromopyrid-3-ylphenyl, 3-(2,3-dihydrobenzo[1,4]dioxin-6-yl)phenyl, 3-(2,3-dihydrobenzo[1,3]dioxol-5-yl) phenyl, indol-1-yl, and the like. Suitable protecting groups include tert-butoxycarbonyl, benzyloxycarbonyl, benzyl, 4-methoxybenzyl, 2-nitrobenzyl, and the like.

"Heterobicycloaryl" means bicycloaryl, as defined in this Application, provided that one or more of the ring carbon atoms indicated are replaced by a hetero atom moiety selected from N, NR, O, S or B, wherein R is hydrogen, ($C_{1-6}$)alkyl or a protecting group, and any carbocyclic ketone, thioketone or iminoketone derivative thereof. In general, the term heterobicycloaryl as used in this Application includes, for example, benzo[1,3]dioxol-5-yl, 3,4-dihydro-2H-[1,8]naphthyridinyl, 3,4-dihydro-2H-quinolinyl, 2,4-dioxo-3,4-dihydro-2H-quinazolinyl, 3-oxo-2,3-dihydrobenzo[1,4]oxazinyl, 5,6,7,8-tetrahydroquinolinyl, and the like. Suitable protecting groups include tert-butoxycarbonyl, benzyloxycarbonyl, benzyl, 4-methoxybenzyl, 2-nitrobenzyl, and the like.

"Heterocycloalkyl" means cycloalkyl, as defined in this Application, provided that one or more of the ring carbon atoms indicated are replaced by a hetero atom moiety selected from N, NR, O, S or B, wherein R is hydrogen, ($C_{1-6}$)alkyl or a protecting group, and any carbocyclic ketone, thioketone or iminoketone derivative thereof (e.g., the term heterocyclo($C_{5-10}$)alkyl includes imidazolidinyl, morpholinyl, piperazinyl, piperidyl, pyrrolidinyl, pyrrolinyl, quinuclidinyl, and the like). For example, optionally substituted hetero($C_{5-10}$)cycloalkyl as used in this Application to define R³ includes morpholin-4-yl, 1-methylpyrrolidin-2-yl, pyrrolidin-1-yl, tetrahydrofur-2-yl, and the like. Suitable protecting groups include acetyl, tert-butoxycarbonyl, benzyloxycarbonyl, benzyl, 4-methoxybenzyl, 2-nitrobenzyl, and the like.

"Hydroxy" means the radical OH. Unless indicated otherwise, the compounds of the invention containing hydroxy radicals include protected derivatives thereof. Suitable protecting groups for hydroxy moieties include benzyl and the like.

"Isomers" mean compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 3rd edition, March, Jerry, John Wiley & Sons, New York, 1985). It is understood that the names and illustration used in this Application to describe compounds of Formula I are meant to be encompassed all possible stereoisomers.

"Leaving group" has the meaning conventionally associated with it in synthetic organic chemistry, i.e., an atom or group displaceable under alkylating conditions, and includes, halogen, hydroxy, alkyloxy, alkylsulfonloxy (e.g., mesyloxy, ethanesulfonyloxy, or the like), arylsulfonyloxy (e.g., benzenesulfonyloxy and tosyloxy, thienyloxy), dihalophosphinoyloxy, tetrahalophosphaoxy, and the like.

"Nitro" means the radical $NO_2$.

"Optional" or "optionally" means that the subsequently described event or circumstance may or may not occur, and that the description includes instances where the event or circumstance occurs and instances in which it does not. For example, the phrase "$R^3$ can be optionally substituted" means that the moiety referred to may or may not contain substituents in order to fall within the scope of the invention.

"N-oxide derivatives" means derivatives of compounds of Formula I in which nitrogens are in an oxidized state (i.e., O—N) and which possess the desired pharmacological activity.

"Oxo" means the radical =O.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide, ammonium hydroxide and calcium hydroxide. Acceptable organic bases include ethanolamine, diethanolamine, triethanolamine, trimethamine, N-methylglucamine and the like.

"Prodrug derivatives" means derivatives of compounds of Formula I which are converted in vivo to the corresponding non-derivatized form of a compound of Formula I.

"Protected derivatives" means derivatives of compounds of Formula I in which a reactive site or sites are blocked with protective groups. Protected derivatives of compounds of Formula I are useful in the preparation of compounds of Formula I or in themselves may be active cysteine protease inhibitors. A comprehensive list of suitable protective groups can be found in T. W. Greene, *Protective Groups in Organic Synthesis,* John Wiley & Sons, Inc. 1981.

"Therapeutically effective amount" means that amount which, when administered to an animal for treating a disease, is, by itself or in combination with additional active ingredients, sufficient to effect such treatment for the disease.

"Treatment" or "treating" means any administration of a compound of the present invention and includes:

(1) Preventing the disease from occurring in an animal which may be predisposed to the disease but does not yet experience or display the pathology or symptomatology of the disease, (2) Inhibiting the disease in an animal that is experiencing or displaying the pathology or symptomatology of the diseased (i.e., arresting further development of the pathology and/or symptomatology), or (3) Ameliorating the disease in an animal that is experiencing or displaying the pathology or symptomatology of the diseased (i.e., reversing the pathology and/or symptomatology).

"Ureido" means the radical —NHC(O)NH$_2$. Unless indicated otherwise, the compounds of the invention containing ureido moieties include protected derivatives thereof. Suitable protective groups for ureido moieties include acetyl, tert-butoxycarbonyl, benzyloxycarbonyl, and the like. For example, a compound of Formula I wherein the $R^1$ contains an ureido radical may exist as either the unprotected or a protected derivative and both the unprotected and protected derivatives fall within the scope of the invention.

Specific Embodiments of the Invention

While the broadest definition of this invention is set forth in the Summary of the Invention, certain aspects of the invention are preferred. One preferred embodiment provides compounds of Formula I in which:

$X^1$ is —$CR^4R^5$— or —$CHR^7$—;

$R^6$ is H;

$R^7$ is ($C_{4-8}$) branched alkyl or —$CH_2$-cyclopropyl;

$R^1$ is hydrogen;

$R^2$ is hydrogen or $R^{2a}$; alternatively, $R^1$ and $R^2$ together represent —$CH_2$—$CH_2$— or —$CH_2$—$NR^8$—$CH_2$—;

$R^{2a}$ represents ($C_{2-4}$) alkyl optionally substituted with a group selected from —$NR^8C(O)OR^{35}$, —$OR^{35}$, —$SR^{35}$, —$S(O)R^{35}$, —$S(O)_2R^{35}$, —$C(O)R^{35}$, —$SO_2NR^8R^{52}$ and —$OP(O)(OR^8)OR^{35}$;

$R^3$ is ($C_{6-10}$)aryl or hetero($C_{5-10}$)aryl, wherein $R^3$ may be substituted further by a radical selected from a group consisting of —$X^3NR^8R^{21}$, —$X^3NR^8C(O)R^{21}$, —$X^3NR^8C(O)OR^{21}$, —$X^3NR^8C(O)NR^8R^{21}$, —$X^3OR^{21}$, —$X^3SR^{21}$, —$X^3C(O)R^{21}$, —$X^3C(O)OR^{21}$, —$X^3OC(O)R^{21}$, —$X^3C(O)NR^8R^{21}$, —$X^3OR^{52}$, —$X^3CONR^8R^{52}$ and —$R^{21}$, wherein:

$X^3$ is a bond or ($C_{1-6}$)alkylene, $R^8$ at each occurrence independently is hydrogen or ($C_{1-6}$)alkyl and $R^{21}$ is ($C_{1-8}$)alkyl or —$X^3R^{22}$, wherein $X^3$ is as defined above;

$R^{22}$ is selected from a group consisting of hetero($C_{5-10}$)cycloalkyl, ($C_{6-10}$)aryl, hetero($C_{5-10}$)aryl and hetero($C_{8-10}$)bicycloaryl, wherein $R^{22}$ may be substituted further by a radical selected from a group consisting of ($C_{1-4}$)alkyl, —$X^3NR^8R^{23}$, —$X^3C(O)NR^8R^{52}$, —$X^3OR^{23}$, —$X^3NR^8C(O)OR^{23}$, —$X^3SO_2NR^8R^{52}$, —$X^3C(O)NR^8R^{23}$, —$X^3SO_2NR^8R^{23}$, —$X^3COR^{23}$, —$X^3OR^{52}$, —$X^3S(O)_2R^{23}$, $X^3N(R^8)_2$ and —$R^{23}$, wherein $X^3$ is a bond or ($C_{1-6}$)alkylene, $R^{52}$ represents —$CH_2CH_2$—$N(CH_2CH_2OH)_2$, —$CH(CH_3)CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{23}$ is ($C_{1-8}$)alkyl or —$X^3R^{24}$, wherein $X^3$ is as defined above;

$R^{24}$ is selected from a group consisting of hetero($C_{5-10}$)cycloalkyl and hetero($C_{5-10}$)aryl, wherein $R^{24}$ may be substituted further with $R^{25}$, —$X^3OR^{52}$, —$X^3NR^8R^{25}$, —$X^3COOR^{25}$ and —$X^3SO_2NR^8R^{52}$; wherein $X^3$ is a bond or ($C_{1-6}$) alkylene, $R^{52}$ represents —$CH_2CH_2$—$N(CH_2CH_2OH)_2$, —$CH(CH_3)CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{25}$ is ($C_{1-8}$)alkyl or —$X^3R^{26}$, wherein $X^3$ is as defined above;

$R^{26}$ is hetero($C_{5-10}$)cycloalkyl; and wherein any of the ($C_{3-10}$)cycloalkyl, hetero($C_{5-10}$)cycloalkyl, ($C_{6-10}$)aryl, hetero($C_{5-10}$)aryl, ($C_{9-10}$)bicycloaryl and hetero($C_{8-10}$)bicycloaryl contained within $R^3$, $R^{22}$, $R^{24}$ and $R^{26}$ may be substituted further with up to five substituents selected from a group consisting of ($C_{1-6}$)alkyl, cyano, halo, nitro, halo-substituted ($C_{1-3}$alkyl, —$X^3NR^{16}R^{16}$, —$X^3OR^{52}$ and —$X^3C(O)R^{16}$, wherein:

$X^3$ is a bond or ($C_{1-6}$)alkylene, $R^{52}$ represents —$CH_2CH_2$—$N(CH_2CH_2OH)_2$, —$CH(CH_3)CH_2N$ ($CH_3)_2$, —$CH_2CH_2OH$, —$CH_2CH_2N(CH_3)_2$ or —$CH_2CN$, $R^{16}$ at each occurrence independently is selected from a group consisting of hydrogen, ($C_{1-3}$)alkyl or halo-substituted ($C_{1-3}$)alkyl and $R^{17}$ is —($C_{1-3}$)alkyl or halo-substituted ($C_{1-3}$)alkyl; and the N-oxide derivatives, prodrug derivatives, protected derivatives, individual stereo isomers and mixtures of stereo isomers, and pharmaceutically acceptable salts thereof, with the proviso that only one of $R^3$, $R^{22}$, $R^{24}$ and $R^{26}$ represents a fused bicyclic ring structure.

A further preferred embodiment of the present invention provides compounds of Formula I wherein:

$X^1$ is —$CHR^7$—;

$R^7$ is i-propyl;

$R^2$ is hydrogen or $R^{2a}$;

$R^{2a}$ represents ($C_4$) alkyl optionally substituted with a group selected from —$NR^8C(O)OR^{35}$ or —$SR^{35}$;

$R^3$ is phenyl or hetero($C_{5-6}$)aryl, wherein $R^3$ may be substituted further by a radical selected from a group consisting of —$X^3NR^8R^{21}$, —$X^3NR^8C(O)R^{21}$, —$X^3NR^8C(O)OR^{21}$ and —$R^{21}$;

$R^{21}$ is —$X^3R^{22}$;

$R^{22}$ is selected from a group consisting of hetero($C_{5-6}$)cycloalkyl, ($C_6$)aryl, hetero($C_{5-10}$)aryl and hetero($C_{8-9}$)bicycloaryl, wherein $R^{22}$ can be optionally substituted further by a radical selected from a group consisting of ($C_{1-4}$)alkyl, —$X^3OR^{23}$, —$X^3NR^8R^{23}$, —$X^3C(O)NR^8R^{23}$, —$X^3C(O)NR^8R^{52}$, —$X^3SO_2NR^8R^{23}$ and $R^{23}$; wherein $X^3$ is a bond or ($C_{1-6}$)alkylene, $R^{52}$ represents —$CH_2CH_2$—$N(CH_2CH_2OH)_2$, —$CH(CH_3)CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{23}$ is ($C_{1-8}$)alkyl or —$X^3R^{24}$, wherein $X^3$ is as defined above;

$R^{24}$ is selected from a group consisting of hetero($C_{5-6}$)cycloalkyl and hetero($C_{5-6}$)aryl, wherein $R^{24}$ may be substituted further with $R^{25}$, —$X^3OR^{52}$, —$X^3NR^8R^{25}$, —$X^3COOR^{25}$ and —$X^3SO_2NR^8R^{52}$; wherein $X^3$ is a bond or ($C_{1-6}$) alkylene, $R^{52}$ represents —$CH_2CH_2$—$N(CH_2CH_2OH)_2$, —$CH(CH_3)CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{25}$ is ($C_{1-4}$)alkyl or —$X^3R^{26}$, wherein $X^3$ is as defined above;

$R^{26}$ is hetero($C_{5-10}$)cycloalkyl; and wherein the ($C_{3-10}$)cycloalkyl contained within $R^{26}$ may be substituted further with up to three groups selected from a group consisting of ($C_{1-2}$)alkyl.

Another preferred embodiment provides compounds of Formula I wherein:

$R^2$ is hydrogen;

$R^3$ is phenyl or hetero($C_{5-6}$)aryl, wherein $R^3$ is substituted by —$R^{21}$;

$R^{21}$ is —$X^3R^{22}$;

$X^3$ is a bond;

$R^{22}$ is hetero($C_6$)aryl and hetero($C_{5-6}$)aryl; wherein $R^{22}$ is substituted further by $R^{23}$;

$R^{23}$ is —$X^3R^{24}$, wherein $X^3$ is a bond;

$R^{24}$ is hetero($C_{5-6}$)aryl, wherein $R^{24}$ may be substituted further with $R^{25}$, —$X^3OR^{52}$, —$X^3NR^8R^{25}$, —$X^3COOR^{25}$ or —$X^3SO_2NR^8R^{52}$; wherein $X^3$ is a bond or ($C_{1-6}$)alkylene, $R^{52}$ represents —$CH_2CH_2$—N($CH_2CH_2OH)_2$, —$CH(CH_3)CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{25}$ is —$X^3R^{26}$, wherein $X^3$ is a bond; and $R^{26}$ is hetero($C_{5-6}$)cycloalkyl substituted with up to two (0–2) groups selected from a group consisting of ($C_{1-2}$)alkyl.

In yet another preferred embodiment of the present invention are provided compounds of Formula I wherein:

$R^1$ and $R^2$ is hydrogen;

$R^3$ is phenyl or hetero($C_{5-6}$)aryl, wherein $R^3$ is substituted by —$R^{21}$;

$R^{21}$ is —$X^3R^{22}$;
—$X^3$ is a bond;
$R^{22}$ is hetero($C_{5-6}$)aryl; wherein $R^{22}$ is substituted by —$R^{23}$;
$R^{23}$ is —$X^3R^{24}$, wherein $X^3$ is a bond;
$R^{24}$ is hetero($C_{5-6}$)aryl substituted by $R^{25}$;
$R^{25}$ is —$X^3R^{26}$, wherein $X^3$ is a bond; and
$R^{26}$ is hetero($C_{5-6}$)cycloalkyl substituted with up to two (0–2) groups selected from a group consisting of ($C_{1-2}$)alkyl.

Particularly preferred compounds of Formula I of the present invention are:

4-Methyl-2-[3'-(2-piperazin-1-yl-thiazol-4-yl)-biphenyl-3-yl]-pentanoic acid cyanomethyl-amide;

4-Methyl-2-{3'-[2-(4-methyl-piperazin-1-yl)-thiazol-4-yl]-biphenyl-3-yl}-pentanoic acid cyanomethyl-amide;

2-{3'-[2-(4-tert-Butyl-piperazin-1-yl)-thiazol-4-yl]-biphenyl-3-yl}-4-methyl-pentanoic acid cyanomethyl-amide;

2-{3'-[2-(3-Dimethylamino-pyrrolidin-1-yl)-thiazol-4-yl]-biphenyl-3-yl}-4-methyl-pentanoic acid cyanomethyl-amide;

4-Methyl-2-[4'-(2-piperazin-1-yl-thiazol-4-yl)-biphenyl-3-yl]-pentanoic acid cyanomethyl-amide;

4-Methyl-2-{4'-[2-(4-methyl-piperazin-1-yl)-thiazol-4-yl]-biphenyl-3-yl}-pentanoic acid cyanomethyl-amide;

4-Methyl-2-{3'-[2-(4-methyl-piperazin-1-yl)-thiazol-4-yl]-biphenyl-3-yl}-pentanoic acid (1-cyano-cyclopropyl)-amide;

4-Methyl-2-[3'-(2-piperazin-1-ylmethyl-thiazol-4-yl)-biphenyl-3-yl]-pentanoic acid cyanomethyl-amide;

4-Methyl-2-{4'-[2-(4-methyl-piperazin-1-yl)-thiazol-4-yl]-biphenyl-3-yl}-pentanoic acid (1-cyano-cyclopropyl)-amide;

4-Methyl-2-{3'-[2-(4-methyl-piperazin-1-yl)-thiazol-4-yl]-biphenyl-3-yl}-pentanoic acid cyanomethyl-amide;

4-Methyl-2-{3'-[2-(4-methyl-piperazin-1-yl)-thiazol-4-yl]-biphenyl-3-yl}-pentanoic acid cyanomethyl-amide;

2-{3'-[2-(4-tert-Butyl-piperazin-1-yl)-thiazol-4-yl]-biphenyl-3-yl}-4-methyl-pentanoic acid cyanomethyl-amide;

4-Methyl-2-[4'-(2-piperazin-1-yl-thiazol-4-yl)-biphenyl-3-yl]-pentanoic acid (1-cyano-cyclopropyl)-amide;

4-Methyl-2-{4'-[2-(4-methyl-piperazin-1-yl)-thiazol-4-yl]-biphenyl-3-yl}-pentanoic acid (1-cyano-cyclopropyl)-amide;

4-Methyl-2-(4'-piperazin-1-yl-biphenyl-3-yl)-pentanoic acid (1-cyano-cyclopropyl)-amide;

4-Methyl-2-[3'-(pyrrolidin-2-ylmethoxy)-biphenyl-3-yl]-pentanoic acid cyanomethyl-amide;

2-[4'-(4-tert-Butyl-piperazin-1-yl)-biphenyl-3-yl]-4-methyl-pentanoic acid cyanomethyl-amide;

4-Methyl-2-(4'-piperazin-1-yl-biphenyl-3-yl)-pentanoic acid cyanomethyl-amide;

4-Methyl-2-[4'-(1,2,3,6-tetrahydro-pyridin-4-yl)-biphenyl-3-yl]-pentanoic acid cyanomethyl-amide;

4-Methyl-2-[4'-(4-methyl-piperazin-1-yl)-biphenyl-3-yl]-pentanoic acid cyanomethyl-amide;

2-[4'-(4-tert-Butyl-piperazin-1-yl)-biphenyl-3-yl]-4-methyl-pentanoic acid (1-cyano-cyclopropyl)-amide;

4-Methyl-2-{4'-[methyl-(1-methyl-pyrrolidin-3-yl)-amino]-biphenyl-3-yl}-pentanoic acid cyanomethyl-amide;

4-Methyl-2-[3'-(pyrrolidin-2-ylmethoxy)-biphenyl-3-yl]-pentanoic acid cyanomethyl-amide;

4-Methyl-2-[4'-(pyrrolidin-2-ylmethoxy)-biphenyl-3-yl]-pentanoic acid cyanomethyl-amide;

4-Methyl-2-[4'-(pyrrolidin-2-ylmethoxy)-biphenyl-3-yl]-pentanoic acid cyanomethyl-amide;

4-Methyl-2-[3'-(1-methyl-pyrrolidin-3-ylmethyl)-biphenyl-3-yl]-pentanoic acid cyanomethyl-amide;

2-{4'-[4-(2-Hydroxy-ethyl)-piperazin-1-yl]-biphenyl-3-yl}-4-methyl-pentanoic acid (1-cyano-cyclopropyl)-amide;

3'-[1-(Cyanomethyl-carbamoyl)-3-methyl-butyl]-biphenyl-4-carboxylic acid methyl-(1-methyl-pyrrolidin-3-yl)-amide;

4-Methyl-2-[3'-(pyrrolidin-3-yloxy)-biphenyl-3-yl]-pentanoic acid cyanomethyl-amide;

4-Methyl-2-(4'-piperazin-1-yl-biphenyl-3-yl)-pentanoic acid cyanomethyl-amide;

3'-[1-(Cyanomethyl-carbamoyl)-3-methyl-butyl]-biphenyl-4-carboxylic acid (2-dimethylamino-ethyl)-amide;

4-Methyl-2-[3'-(pyrrolidin-3-yloxy)-biphenyl-3-yl]-pentanoic acid cyanomethyl-amide;

4-Methyl-2-[3-(7-nitro-1H-indol-4-yl)-phenyl]-pentanoic acid cyanomethyl-amide;

4-Methyl-2-[3'-(pyrrolidin-3-yloxy)-biphenyl-3-yl]-pentanoic acid cyanomethyl-amide;

3'-[1-(Cyanomethyl-carbamoyl)-3-methyl-butyl]-biphenyl-4-carboxylic acid (2-morpholin-4-yl-ethyl)-amide;

2-{3'-[1-(2-Hydroxy-ethyl)-piperidin-4-ylmethyl]-biphenyl-3-yl}-4-methyl-pentanoic acid cyanomethyl-amide;

2-(3-{5-[4-(2-Hydroxy-ethyl)-piperazine-1-sulfonyl]-thiophen-2-yl}-phenyl)-4-methyl-pentanoic acid cyanomethyl-amide;

4-Methyl-2-{3-[2-(4-methyl-piperazin-1-yl)-thiazol-5-yl]-phenyl}-pentanoic acid cyanomethyl-amide;

3'-[1-(Cyanomethyl-carbamoyl)-3-methyl-butyl]-biphenyl-4-carboxylic acid (2-dimethylamino-ethyl)-methyl-amide;

4-Methyl-2-[4'-(piperidin-4-yloxy)-biphenyl-3-yl]-pentanoic acid cyanomethyl-amide;

4-Methyl-2-{3-[5-(4-methyl-piperazine-1-sulfonyl)-thiophen-2-yl]-phenyl}-pentanoic acid cyanomethyl-amide;

2-{3-[3-(2-Amino-ethyl)-1H-indol-5-yl]-phenyl}-4-methyl-pentanoic acid cyanomethyl-amide;

4-Methyl-2-[4'-(pyrrolidin-3-yloxy)-biphenyl-3-yl]-pentanoic acid cyanomethyl-amide;

2-[3'-(2-Dimethylamino-thiazol-4-yl)-biphenyl-3-yl]-4-methyl-pentanoic acid cyanomethyl-amide;

N-(cyanomethyl)-4-methyl-2-[3-(pyrid-2-yl)phenyl]pentanamide;

N-(cyanomethyl)-2-[3-(1H-indol-5-yl)phenyl]-4-methylpentanamide;

N-(cyanomethyl)-2-[3-(1H-indol-6-yl)phenyl]-4-methylpentanamide;

N-cyanomethyl-2-(4'-methylsulfonylbiphenyl-3-yl)-4-methylpentanamide;

N-(cyanomethyl)-4-methyl-2-[3-(5-pyrimidinyl)phenyl]pentanamide;

N-(cyanomethyl)-4-methyl-2-[3-(2-pyrimidinyl)phenyl]
pentanamide;
3'-(1-cyanomethylcarbamoyl)-3-methylbutyl]biphenyl-4-
carboxamide;
N-(cyanomethyl)-2-[3-(4-isoquinolinyl)phenyl]-4-
methylpentanamide;
N-(cyanomethyl)-4-methyl-2-[3-(3-quinolinyl)phenyl]
pentanamide;
2-[4'-(acetylamino)[1,1'-biphenyl]-3-yl]-N-(cyanomethyl)-
4-methylpentanamide;
N-(cyanomethyl)-2-[3-(3-furyl)phenyl]-4-
methylpentanamide;
N-(cyanomethyl)-4-methyl-2-[3-(2-methyl-6-quinolinyl)
phenyl]pentanamide;
N-(cyanomethyl)-2-[3-(4,5-dichloro-1H-imidazol-2-yl)
phenyl]-4-methylpentanamide;
N-(cyanomethyl)-2-[3-(3,5-dimethyl-4-isoxazolyl)phenyl]-
4-methylpentanamide;
tert-butyl 3'-(1-cyanomethylcarbamoyl-3-methylbutyl)
biphenyl-4-ylcarbamate;
N-(cyanomethyl)-4-methyl-2-[3-(1-oxo-2,3-dihydro-1H-
inden-5-yl)phenyl]pentanamide;
N-(cyanomethyl)-2-(3-methoxyphenyl)-4-
methylpentanamide;
2,2-dichloroethyl 3'-(1-cyanomethylcarbamoyl-3-
methylbutyl)biphenyl-4-ylcarbamate;
N-(cyanomethyl)-4-methyl-2-(4'-phenoxy[1,1'-biphenyl]-3-
yl)pentanamide;
N-(cyanomethyl)-4-methyl-2-[3-(2-oxo-2,3-dihydro-1,3-
benzothiazol-6-yl)phenyl]pentanamide;
3-(1-{[(cyanomethyl)amino]carbonyl}-3-methylbutyl)
phenyl 2-(3-hydroxyphenyl)-4-methylpentanoate;
tert-butyl 3'-(1-cyanomethylcarbamoyl-3-methylbutyl)
biphenyl-4-ylmethylcarbamate;
N-(cyanomethyl)-2-[3-(2,3-dihydro-1H-indol-5-yl)phenyl]-
4-methylpentanamide;
tert-butyl N-5-[3-(1-cyanomethylcarbamoyl-3-methylbutyl)
phenyl]pyrimidin-2-yl-N-(tert-butoxycarbonyl)
carbamate;
N-(cyanomethyl)-4-methyl-2-[3-(1-methyl-1H-indol-5-yl)
phenyl]pentanamide;
N-(cyanomethyl)-4-methyl-2-[3-(7-nitro-1H-indol-5-yl)
phenyl]pentanamide;
N-(cyanomethyl)-4-methyl-2-[3-(1H-pyrrolo[2,3-b]pyridin-
5-yl)phenyl]pentanamide;
2-[3-(7-amino-1H-indol-5-yl)phenyl]-N-(cyanomethyl)-4-
methylpentanamide;
N-(cyanomethyl)-4-methyl-2-[3-(7-nitro-2,3-dihydro-1H-
indol-5-yl)phenyl]pentanamide;
5-[3-(1-{[(cyanomethyl)amino]carbonyl}-3-methylbutyl)
phenyl]-1H-indole-2-carboxylic acid;
5-[3-(1-{[(cyanomethyl)amino]carbonyl}-3-methylbutyl)
phenyl]-1H-indole-2-carboxamide;
N-(cyanomethyl)-4-methyl-2-[3-(2-oxo-2,3-dihydro-1H-
pyrrolo[2,3-b]pyridin-5-yl)phenyl]pentanamide;
N-(cyanomethyl)-4-methyl-2-[3'-(4-morpholinyl)[1,1'-
biphenyl]-3-yl]pentanamide;
N-(cyanomethyl)-4-methyl-2-[4'-(4-morpholinyl)[1,1'-
biphenyl]-3-yl]pentanamide;
N-(cyanomethyl)-4-methyl-2-[2'-(4-morpholinyl)[1,1'-
biphenyl]-3-yl]pentanamide;
N-(cyanomethyl)-2-(3-{3-[(dimethylamino)methyl]-1H-
indol-5-yl}phenyl)-4-methylpentanamide;
2-[4'-(aminomethyl)[1,1'-biphenyl]-3-yl]-N-(cyanomethyl)-
4-methylpentanamide;
N-(cyanomethyl)-4-methyl-2-[4'-(4-methyl-1-piperazinyl)
[1,1'-biphenyl]-3-yl]pentanamide;
N-(cyanomethyl)-4-methyl-2-[4'-(1-piperazinyl)[1,1'-
biphenyl]-3-yl]pentanamide;
ethyl 4-[3'-(1-{[(cyanomethyl)amino]carbonyl}-3-
methylbutyl)[1,1'-biphenyl]-4-yl]-1-
piperazinecarboxylate;
2-{3-[3-(2-aminoethyl)-1H-indol-5-yl]phenyl}-N-
(cyanomethyl)-4-methylpentanamide;
4-Methyl-2-[3'-(2-piperazin-1-yl-thiazol-4-yl)-biphenyl-3-
yl]-pentanoic acid cyanomethyl-amide;
2-(4'-Hydroxy-3'-isoxazol-5-yl-biphenyl-3-yl)-4-methyl-
pentanoic acid cyanomethyl-amide;
2-[4'-(2-Dimethylamino-thiazol-4-yl)-biphenyl-3-yl]-4-
methyl-pentanoic acid cyanomethyl-amide;
2-[3'-(2-Guanidino-thiazol-4-yl)-biphenyl-3-yl]-4-methyl-
pentanoic acid cyanomethyl-amide;
4-Methyl-2-{3-[5-(4-methyl-piperazine-1-sulfonyl)-
thiophen-2-yl]-phenyl}-pentanoic acid cyanomethyl-
amide;
4-Methyl-2-{3-[2-(4-methyl-piperazin-1-yl)-thiazol-4-yl]-
phenyl}-pentanoic acid cyanomethyl-amide;
N-{3-[5-(3,5-Dichloro-2-hydroxy-phenyl)-1H-pyrazol-3-
yl]-propyl}-guanidine;
2-{3-[2-(3,5-Dimethyl-piperazin-1-yl)-thiazol-4-yl]-
phenyl}-4-methyl-pentanoic acid cyanomethyl-amide;
4-Methyl-2-{3-[2-(4-methyl-piperazin-1-yl)-thiazol-5-yl]-
phenyl}-pentanoic acid cyanomethyl-amide;
4-Methyl-2-[2-(4-piperazin-1-yl-phenyl)-thiazol-4-yl]-
pentanoic acid cyanomethyl-amide;
4-Methyl-2-{3'-[2-(4-methyl-piperazin-1-yl)-thiazol-4-yl]-
biphenyl-3-yl}-pentanoic acid cyanomethyl-amide;
4-Methyl-2-{4'-[2-(4-methyl-piperazin-1-yl)-thiazol-4-yl]-
biphenyl-3-yl}-pentanoic acid cyanomethyl-amide;
4-Methyl-2-[3'-(pyrrolidin-3-yloxy)-biphenyl-3-yl]-
pentanoic acid cyanomethyl-amide;
2-{3'-[1-(2-Hydroxy-ethyl)-piperidin-4-yloxy]-biphenyl-3-
yl}-4-methyl-pentanoic acid cyanomethyl-amide;
4-Methyl-2-[3'-(piperidin-4-yloxy)-biphenyl-3-yl]-
pentanoic acid cyanomethyl-amide;
4-Methyl-2-[4'-(piperidin-4-yloxy)-biphenyl-3-yl]-
pentanoic acid cyanomethyl-amide;
2-{4'-[1-(2-Hydroxy-ethyl)-piperidin-4-yloxy]-biphenyl-3-
yl}-4-methyl-pentanoic acid cyanomethyl-amide;
4-Methyl-2-[4'-(pyrrolidin-3-yloxy)-biphenyl-3-yl]-
pentanoic acid cyanomethyl-amide;
2-[3'-(2-Dimethylamino-ethoxy)-biphenyl-3-yl]-4-methyl-
pentanoic acid cyanomethyl-amide;
4-{3'-[1-(Cyanomethyl-carbamoyl)-3-methyl-butyl]-
biphenyl-4-yloxy}-piperidine-1-carboxylic acid tert-butyl
ester;
4-{3'-[1-(Cyanomethyl-carbamoyl)-3-methyl-butyl]-
biphenyl-3-yloxy}-piperidine-1-carboxylic acid tert-butyl
ester;
3-{3'-[1-(Cyanomethyl-carbamoyl)-3-methyl-butyl]-
biphenyl-3-yloxy}-pyrrolidine-1-carboxylic acid tert-
butyl ester;
3-{3'-[1-(Cyanomethyl-carbamoyl)-3-methyl-butyl]-
biphenyl-4-yloxy}-pyrrolidine-1-carboxylic acid tert-
butyl ester;
2-[5'-Fluoro-2'-(pyrrolidin-3-yloxy)-biphenyl-3-yl]-4-
methyl-pentanoic acid cyanomethyl-amide;
3-{3'-[1-(Cyanomethyl-carbamoyl)-3-methyl-butyl]-
biphenyl-3-yloxy}-pyrrolidine-1-carboxylic acid tert-
butyl ester;
4-Methyl-2-[3'-(pyrrolidin-3-yloxy)-biphenyl-3-yl]-
pentanoic acid cyanomethyl-amide;
4-Methyl-2-[3-(2-piperazin-1-ylmethyl-thiazol-4-yl)-
phenyl]-pentanoic acid cyanomethyl-amide;

4-(4-{3-[1-(Cyanomethyl-carbamoyl)-3-methyl-butyl]-phenyl}-thiazol-2-ylmethyl)-piperazine-1-carboxylic acid tert-butyl ester;

3-{3'-[1-(Cyanomethyl-carbamoyl)-3-methyl-butyl]-5-fluoro-biphenyl-2-yloxy}-pyrrolidine-1-carboxylic acid tert-butyl ester;

4-Methyl-2-[3'-(pyrrolidin-3-yloxy)-biphenyl-3-yl]-pentanoic acid cyanomethyl-amide;

2-(3-Isoquinolin-4-yl-phenyl)-4-methyl-pentanoic acid cyanomethyl-amide;

4-Methyl-2-[4'-(toluene-3-sulfonylamino)-biphenyl-3-yl]-pentanoic acid cyanomethyl-amide;

4-Methyl-2-(4'-nitro-biphenyl-3-yl)-pentanoic acid cyanomethyl-amide;

2-(2',4'-Dimethoxy-biphenyl-3-yl)-4-methyl-pentanoic acid cyanomethyl-amide;

2-(4'-Methoxy-biphenyl-3-yl)-4-methyl-pentanoic acid cyanomethyl-amide;

2-(4'-Amino-biphenyl-3-yl)-4-methyl-pentanoic acid cyanomethyl-amide;

2-(3'-Amino-biphenyl-3-yl)-4-methyl-pentanoic acid cyanomethyl-amide;

4-Methyl-2-(3'-nitro-biphenyl-3-yl)-pentanoic acid cyanomethyl-amide;

4-Methyl-2-(4'-sulfamoyl-biphenyl-3-yl)-pentanoic acid cyanomethyl-amide;

2-(5'-Acetyl-2'-morpholin-4-yl-biphenyl-3-yl)-4-methyl-pentanoic acid cyanomethyl-amide;

N-(cyanomethyl)-4-methyl-2-[3-(2-methyl-6-quinolinyl)phenyl]pentanamide;

N-(cyanomethyl)-4-methyl-2-[3-(3-quinolinyl)phenyl]pentanamide;

N-(cyanomethyl)-2-[3-(1H-indol-5-yl)phenyl]-4-methylpentanamide;

4-[(tert-butoxycarbonyl)amino]-3'-(1-{[(cyanomethyl)amino]carbonyl}-3-methylbutyl)-1,1'-biphenyl;

4-{[(tert-butoxycarbonyl)amino]methyl}-3'-(1-{[(cyanomethyl)amino]carbonyl}-3-methylbutyl)-1,1'-biphenyl;

2-[4'-(aminomethyl)[1,1'-biphenyl]-3-yl]-N-(cyanomethyl)-4-methylpentanamide;

N-(cyanomethyl)-4-methyl-2-[3-(1-methyl-1H-indol-5-yl)phenyl]pentanamide;

2-[3-(7-nitro-1H-indol-5-yl)phenyl]-N-(cyanomethyl)-4-methylpentanamide;

N-(cyanomethyl)-4-methyl-2-[3-(7-nitro-2,3-dihydro-1H-indol-5-yl)phenyl]pentanamide;

2-[3-(7-amino-1H-indol-5-yl)phenyl]-N-(cyanomethyl)-4-methylpentanamide;

N-(cyanomethyl)-2-(3-{3-[(dimethylamino)methyl]-1H-indol-5-yl}phenyl)-4-methylpentanamide;

N-(cyanomethyl)-4-methyl-2-[3-(1H-pyrrolo[2,3-b]pyridin-5-yl)phenyl]pentanamide;

2-{3-[3-(2-aminoethyl)-1H-indol-5-yl]phenyl}-N-(cyanomethyl)-4-methylpentanamide;

(2R)-N-(cyanomethyl)-4-methyl-2-[4'-(4-methyl-1-piperazinyl)[1,1'-biphenyl]-3-yl]pentanamide;

(2R)-N-(cyanomethyl)-4-methyl-2-[4'-(1-piperazinyl)[1,1'-biphenyl]-3-yl]pentanamide;

N-(cyanomethyl)-4-methyl-2-[3-(6-quinolinyl)phenyl]pentanamide;

N-(cyanomethyl)-3-cyclopropyl-2-[4'-(4-methyl-1-piperazinyl)[1,1'-biphenyl]-3-yl]propanamide;

N-(cyanomethyl)-4-methyl-2-[4'-(1,2,3,6-tetrahydro-4-pyridinyl)[1,1'-biphenyl]-3-yl]pentanamide;

(4S)-N-(cyanomethyl)-4-methyl-2-[4'-(4-methyl-1-piperazinyl)[1,1'-biphenyl]-3-yl]hexanamide;

(2R)-N-(cyanomethyl)-2-{4'-[4-(2-hydroxyethyl)-1-piperazinyl][1,1'-biphenyl]-3-yl}-4-methylpentanamide;

N-(cyanomethyl)-4-methyl-2-[2'-(1-piperazinyl)[1,1'-biphenyl]-3-yl]pentanamide;

(2R)-N-(cyanomethyl)-4-methyl-2-{3-[6-(1-piperazinyl)-3-pyridinyl]phenyl}pentanamide;

(2R)-N-(cyanomethyl)-4-methyl-2-[4'-(4-pyridinyl)[1,1'-biphenyl]-3-yl]pentanamide;

(2R)-N-(cyanomethyl)-2-{4'-[4-(2-hydroxy-2-methylpropyl)-1-piperazinyl][1,1'-biphenyl]-3-yl}-4-methylpentanamide;

N-(cyanomethyl)-4-methyl-2-[4'-(4-piperidinyl)[1,1'-biphenyl]-3-yl]pentanamide;

4-Methyl-2-[4'-(4-methyl-piperazin-1-yl)-biphenyl-3-yl]-pentanoic acid cyanomethyl-amide;

2-{4'-[4-(2-Hydroxy-ethyl)-piperazin-1-yl]-biphenyl-3-yl}-4-methyl-pentanoic acid (1-cyano-cyclopropyl)-amide;

4-Methyl-2-[3'-(4-methyl-piperazin-1-yl)-biphenyl-3-yl]-pentanoic acid cyanomethylamide;

2-(3-{2-[4-(2-Hydroxy-ethyl)-piperazin-1-yl]-thiazol-4-yl}-phenyl)-4-methyl-pentanoic acid (1-cyano-cyclopropyl)-amide;

2-Biphenyl-3-yl-4-methyl-pentanoic acid (cyano-methyl-methyl)-amide;

2-Biphenyl-3-yl-4-methyl-pentanoic acid (1-cyano-3-methylsulfanyl-propyl)-amide;

[5-(2-Biphenyl-3-yl-4-methyl-pentanoylamino)-5-cyano-pentyl]-carbamic acid benzyl ester;

4-Methyl-2-[3-(4-methyl-piperazin-1-yl)-phenyl]-pentanoic acid cyanomethyl-amide;

2-Biphenyl-3-yl-4-methyl-pentanoic acid (1-cyano-pentyl)-amide;

4-Methyl-2-(3'-piperazin-1-yl-biphenyl-3-yl)-pentanoic acid cyanomethyl-amide;

4-{3'-[1-(Cyanomethyl-carbamoyl)-3-methyl-butyl]-biphenyl-3-yl}-piperazine-1-carboxylic acid tert-butyl ester;

2-(5-{4-[4-(2-Hydroxy-ethyl)-piperazin-1-yl]-phenyl}-pyridin-3-yl)-4-methyl-pentanoic acid cyanomethyl-amide;

2-{5-[4-(4-Formyl-piperazin-1-yl)-phenyl]-pyridin-3-yl}-4-methyl-pentanoic acid cyanomethyl-amide;

4-Methyl-2-[5-(4-piperazin-1-yl-phenyl)-pyridin-3-yl]-pentanoic acid cyanomethyl-amide;

3'-[1-(Cyanomethyl-carbamoyl)-3-methyl-butyl]-biphenyl-2-carboxylic acid methyl ester;

2-[3-(2,3-Dihydro-benzo[1,4]dioxin-6-yl)-phenyl]-4-methyl-pentanoic acid cyanomethyl-amide;

2-[4'-(1-Hydroxy-ethyl)-biphenyl-3-yl]-4-methyl-pentanoic acid cyanomethyl-amide;

2-(3',5'-Bis-trifluoromethyl-biphenyl-3-yl)-4-methyl-pentanoic acid cyanomethyl-amide;

2-(4'-Cyano-2'-methyl-biphenyl-3-yl)-4-methyl-pentanoic acid cyanomethyl-amide;

N-[1-(Cyanomethyl-carbamoyl)-2-(2-fluoro-3-methyl-phenylmethanesulfonyl)-ethyl]-benzamide;

N-[1-(Cyanomethyl-carbamoyl)-2-(2,5-difluoro-phenylmethanesulfonyl)-ethyl]-benzamide;

2-{3'-[4-(2-Hydroxy-ethyl)-piperazine-1-sulfonyl]-4'-methoxy-biphenyl-3-yl}-4-methyl-pentanoic acid cyanomethyl-amide;

3'-[1-(Cyanomethyl-carbamoyl)-3-methyl-butyl]-biphenyl-4-carboxylic acid (2-morpholin-4-yl-ethyl)-amide;

3'-[1-(Cyanomethyl-carbamoyl)-3-methyl-butyl]-biphenyl-3-carboxylic acid (2-morpholin-4-yl-ethyl)-amide;

4-Methyl-2-[3'-(2-morpholin-4-yl-ethylsulfamoyl)-biphenyl-3-yl]-pentanoic acid cyanomethyl-amide;

3'-[1-(Cyanomethyl-carbamoyl)-3-methyl-butyl]-biphenyl-2-carboxylic acid (2-morpholin-4-yl-ethyl)-amide;

3'-[1-(Cyanomethyl-carbamoyl)-3-methyl-butyl]-biphenyl-4-carboxylic acid (2-dimethylamino-ethyl)-methyl-amide;

3'-[1-(Cyanomethyl-carbamoyl)-3-methyl-butyl]-biphenyl-4-carboxylic acid (2-dimethylamino-ethyl)-amide;

3'-[1-(Cyanomethyl-carbamoyl)-3-methyl-butyl]-biphenyl-4-carboxylic acid methyl-(2-morpholin-4-yl-ethyl)-amide;

2-(3'-Fluoro-biphenyl-3-yl)-4-methyl-pentanoic acid cyanomethyl-amide;

2-[3-(6-Bromo-pyridin-2-yl)-phenyl]-4-methyl-pentanoic acid cyanomethyl-amide;

2-(2'-Cyano-biphenyl-3-yl)-4-methyl-pentanoic acid cyanomethyl-amide;

2-(3'-Cyano-biphenyl-3-yl)-4-methyl-pentanoic acid cyanomethyl-amide;

2(4'-Cyano-biphenyl-3-yl)-4-methyl-pentanoic acid cyanomethyl-amide;

4-Methyl-2-(3-quinolin-8-yl-phenyl)-pentanoic acid cyanomethyl-amide;

4-Methyl-2-(3-quinolin-3-yl-phenyl)-pentanoic acid cyanomethyl-amide;

4-Methyl-2-(4'-trifluoromethoxy-biphenyl-3-yl)-pentanoic acid cyanomethyl-amide;

4-Methyl-2-[3-(5-nitro-thiazol-2-yl)-phenyl]-pentanoic acid cyanomethyl-amide;

2-(4'-Acetylamino-biphenyl-3-yl)-4-methyl-pentanoic acid cyanomethyl-amide;

4-Methyl-2-[4'-(4-methyl-piperazine-1-sulfonyl)-biphenyl-3-yl]-pentanoic acid cyanomethyl-amide;

4-Methyl-2-[3'-(4-methyl-piperazine-1-sulfonyl)-biphenyl-3-yl]-pentanoic acid cyanomethyl-amide;

4-Methyl-2-[4'-(piperazine-1-sulfonyl)-biphenyl-3-yl]-pentanoic acid cyanomethyl-amide;

2-{4'-[4-(2-Hydroxy-ethyl)-piperazine-1-carbonyl]-biphenyl-3-yl}-4-methyl-pentanoic acid cyanomethyl-amide;

2-{3'-[4-(2-Hydroxy-ethyl)-piperazine-1-carbonyl]-biphenyl-3-yl}-4-methyl-pentanoic acid cyanomethyl-amide;

4-Methyl-2-[4'-(2-morpholin-4-yl-ethylsulfamoyl)-biphenyl-3-yl]-pentanoic acid cyanomethyl-amide;

2-(4'-{2-[Bis-(2-hydroxy-ethyl)-amino]-ethylsulfamoyl}-biphenyl-3-yl)-4-methyl-pentanoic acid cyanomethyl-amide;

4-Methyl-2-[4'-(3-morpholin-4-yl-propylsulfamoyl)-biphenyl-3-yl]-pentanoic acid cyanomethyl-amide;

4-Methyl-2-[4'-(3-morpholin-4-yl-propylsulfamoyl)-biphenyl-3-yl]-pentanoic acid cyanomethyl-amide;

2-[4'-(2-Dimethylamino-1-methyl-ethylsulfamoyl)-biphenyl-3-yl]-4-methyl-pentanoic acid cyanomethyl-amide;

2-[4'-(2-Hydroxy-ethylsulfamoyl)-biphenyl-3-yl]-4-methyl-pentanoic acid cyanomethyl-amide;

2-[4'-(2-Hydroxy-ethylsulfamoyl)-biphenyl-3-yl]-4-methyl-pentanoic acid cyanomethyl-amide;

2-[4'-(3-Dimethylamino-pyrrolidine-1-sulfonyl)-biphenyl-3-yl]-4-methyl-pentanoic acid cyanomethyl-amide;

2-{3'-[2-(3-Dimethylamino-pyrrolidin-1-yl)-thiazol-4-yl]-biphenyl-3-yl}-4-methyl-pentanoic acid cyanomethyl-amide;

4-Methyl-2-[4'-(2-piperazin-1-yl-thiazol-4-yl)-biphenyl-3-yl]-pentanoic acid cyanomethyl-amide;

[5-(5-Amino-1H-pyrrolo[3,2-b]pyridin-2-yl)-6,3'-dihydroxy-biphenyl-3-yl]-acetic acid;

2-{3'-[2-(4-tert-Butyl-piperazin-1-yl)-thiazol-4-yl]-biphenyl-3-yl}-4-methyl-pentanoic acid cyanomethyl-amide;

2-{3'-[2-(3-Dimethylamino-pyrrolidin-1-yl)-thiazol-4-yl]-biphenyl-3-yl}-4-methyl-pentanoic acid cyanomethyl-amide;

4-Methyl-2-[3'-(2-piperazin-1-yl-thiazol-4-yl)-biphenyl-3-yl]-pentanoic acid (1-cyano-cyclopropyl)-amide;

4-Methyl-2-[3'-(2-piperazin-1-ylmethyl-thiazol-4-yl)-biphenyl-3-yl]-pentanoic acid cyanomethyl-amide;

4-Methyl-2-[4'-(2-piperazin-1-yl-thiazol-4-yl)-biphenyl-3-yl]-pentanoic acid (1-cyano-cyclopropyl)-amide;

4-Methyl-2-{4'-[methyl-(1-methyl-pyrrolidin-3-yl)-sulfamoyl]-biphenyl-3-yl}-pentanoic acid cyanomethyl-amide; and 2-[4'-(4-Formyl-piperazine-1-sulfonyl)-biphenyl-3-yl]-4-methyl-pentanoic acid cyanomethyl-amide; and the N-oxide derivatives, prodrug derivatives, protected derivatives, individual isomers and mixtures of isomers thereof; and the pharmaceutically acceptable salts thereof.

Another aspect of the present invention provides a pharmaceutical composition comprising a therapeutically effective amount of a compound of claim 1 in combination with one or more pharmaceutically acceptable excipient(s). A preferred pharmaceutical composition further comprises one or more active ingredient(s) selected from the group consisting of (i) a therapeutically effective amount of a bisphosphonic acid or acid ester thereof or a pharmaceutically acceptable salt thereof and (ii) a therapeutically effective amount of an estrogen receptor agonist or a pharmaceutically acceptable salt thereof.

A preferred bisphosphonic acid is selected from the group consisting of 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof.

A particularly preferred pharmaceutical composition is one wherein the bisphosphonic acid is 1,1-dichloromethylene-1,1-diphosphonic acid or a pharmaceutically acceptable salt thereof. The preferred pharmaceutical salt of the bisphonic acid is 1,1-dichloromethylene-1,1-diphosphonate monosodium trihydrate.

In yet another aspect of the present invention is provided a method for treating a disease in an animal in which inhibition of a cysteine protease can prevent, inhibit or ameliorate the pathology and/or symptomatology of the disease, which method comprises administering to the animal a therapeutically effective amount of compound of claim 1 or a N-oxide derivative or individual isomer or mixture of isomers thereof; or a pharmaceutically acceptable salt thereof; preferably the disease treated is osteoporosis.

The present invention in yet another aspect provides a process for preparing a compound of Formula I:

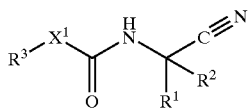

I

X¹ is selected from a group consisting of —CR⁴R⁵—, —CR⁶R⁷— and —NR⁷—, wherein:
R⁴ and R⁵ along with the carbon atom to which they are attached represents

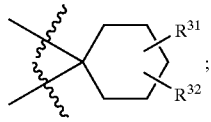

where R³¹ and R³² independently represent hydrogen or hydroxy, alternatively R³¹ and R³² can be taken together to represent an oxo (=O) group;
R⁶ is hydrogen or (C₁₋₆)alkyl; and
R⁷ is (C₁₋₈)alkyl or (CH₂)₁₋₃ cyclopropyl;
R¹ is hydrogen or (C₁₋₆)alkyl;
R² is selected from a group consisting of hydrogen and R²ᵃ;
alternatively R¹ and R² together represent C₂₋₅ alkylene or —CH₂NR⁸CH₂—, or both R¹ and R² simultaneously represent fluoro;
R²ᵃ represents (C₁₋₈) alkyl optionally substituted with a group selected from —NR⁸R³⁵, —NR⁸C(O)R³⁵, —NR⁸C(O)OR³⁵, —NR⁸C(O)NR⁸R³⁵, —NR⁸C(NR⁸)NR⁸R³⁵, —OR³⁵, —SR³⁵, —S(O)R³⁵, —S(O)₂R³⁵, —C(O)R³⁵, —C(O)OR³⁵, —OC(O)R³⁵, —C(O)NR⁸R³⁵, —OC(O)NR⁸R³⁵, —S(O)₂NR⁸R³⁵, —P(O)(OR⁸)OR³⁵, —OR⁵², —CONR⁸R⁵², —SO₂NR⁸R⁵² and —OP(O)(OR⁸)OR³⁵;
R³⁵ is selected from a group consisting of (C₁₋₄) alkyl, —(CH₂)₀₋₃(C₃₋₁₂)cycloalkyl, —(CH₂)₀₋₃hetero(C₅₋₁₀)cycloalkyl, —(CH₂)₀₋₃(C₆₋₁₀)aryl, —(CH₂)₀₋₃hetero(C₅₋₁₀)aryl, —(CH₂)₀₋₃(C₉₋₁₀)bicycloaryl and —(CH₂)₀₋₃hetero(C₈₋₁₀)bicycloaryl;
R³ is selected from a group consisting of (C₆₋₁₀)aryl, (C₃₋₁₀)cycloalkyl, (C₃₋₁₀)heterocycloalkyl, hetero(C₅₋₁₀)aryl, (C₉₋₁₀)bicycloaryl and hetero(C₈₋₁₀) bicycloaryl, wherein:
R³ may be substituted further by a radical selected from a group consisting of —X³NR⁸R²¹, —X³NR⁸C(O)R²¹, —X³NR⁸C(O)OR²¹, —X³NR⁸C(O)NR⁸R²¹, —X³NR⁸C(NR⁸)NR⁸R²¹, —X³OR²¹, —X³SR²¹, —X³S(O)R²¹, —X³S(O)₂R²¹, —X³C(O)R²¹, —X³C(O)OR²¹, —X³OC(O)R²¹, —X³C(O)NR⁸R²¹, —X³OC(O)NR⁸R²¹, —X³S(O)₂NR⁸R²¹, —X³P(O)(OR⁸)OR²¹, —X³OR⁵², —X³CONR⁸R⁵², —X³SO₂NR⁸R⁵², —X³OP(O)(OR⁸)OR²¹ and —R²¹, wherein:
X³ is a bond or (C₁₋₆)alkylene, R⁸ at each occurrence independently is hydrogen or (C₁₋₆)alkyl, R⁵² represents —CH₂CH₂—N(CH₂CH₂OH)₂, —CH(CH₃)CH₂N(CH₃)₂, —CH₂CH₂OH, —CH₂CH₂N(CH₃)₂ or —CH₂CN, and R²¹ is —(C₁₋₈)alkyl or —X³R²², wherein X³ is as defined above and R²² is selected from a group consisting of (C₃₋₁₀)cycloalkyl, hetero(C₅₋₁₀)cycloalkyl, (C₆₋₁₀)aryl, hetero(C₅₋₁₀)aryl, (C₉₋₁₀)bicycloaryl and hetero(C₈₋₁₀)bicycloaryl, wherein:
R²² may be substituted further by a radical selected from a group consisting of —X³NR⁸R²³, —X³NR⁸C(O)R²³, —X³NR⁸C(O)OR²³, —X³NR⁸C(O)NR⁸R²³, —X³OR²³, —X³NR⁸C(NR⁸)NR⁸R²³, —X³SR²³, —X³S(O)R²³, —X³S(O)₂R²³, —X³C(O)R²³, —X³OC(O)R²³, —X³C(O)OR²³, —X³C(O)NR⁸R²³, —X³OC(O)NR⁸R²³, —X³S(O)₂NR⁸R²³, —X³OR⁵², —X³CONR⁸R⁵², —X³SO₂NR⁸R⁵², —X³P(O)(OR⁸)OR²³, —X³OP(O)(OR⁸)OR²³ and —R²³, wherein:
X³ is a bond or (C₁₋₆)alkylene and R⁸ at each occurrence independently is hydrogen or (C₁₋₆)alkyl, R⁵² represents CH₂CH₂—N(CH₂CH₂OH)₂, CH(CH₃)CH₂N(CH₃)₂, CH₂CH₂OH, CH₂CH₂N(CH₃)₂ or CH₂CN, and R²³ is (C₁₋₈)alkyl or —X³R²⁴, wherein X³ is as defined above and R²⁴ is selected from a group consisting of (C₃₋₁₀) cycloalkyl, hetero(C₅₋₁₀)cycloalkyl, (C₆₋₁₀)aryl, hetero(C₅₋₁₀)aryl, (C₉₋₁₀)bicycloaryl and hetero (C₈₋₁₀)bicycloaryl, wherein
R²⁴ may be substituted further by a radical selected from a group consisting of —X³NR⁸R²⁵, —X³NR⁸C(O)R²⁵, —X³NR⁸C(O)OR²⁵, —X³OR²⁵, —X³NR⁸C(O)NR⁸R²⁵, —X³NR⁸C(NR⁸)NR⁸R²⁵, —X³SR²⁵, —X³C(O)R²⁵, —X³S(O)₂R²⁵, —X³C(O)R²⁵, —X³OS(O)R²⁵, —X³C(O)OR²⁵, —X³C(O)NR⁸R²⁵, —X³OC(O)NR⁸R²⁵, —X³S(O)₂NR⁸R²⁵, —X³P(O)(OR⁸)OR²⁵, —X³OR⁵², —X³CONR⁸R⁵², —X³SO₂NR⁸R⁵², —X³OP(O)(OR⁸)OR²⁵ and —R²⁵, wherein:
X³ is a bond or (C₁₋₆)alkylene and R⁸ at each occurrence independently is hydrogen or (C₁₋₆) alkyl, R⁵² represents —CH₂CH₂—N(CH₂CH₂OH)₂, —CH(CH₃)CH₂N(CH₃)₂, —CH₂CH₂OH, —CH₂CH₂N(CH₃)₂ or —CH₂CN, and R²⁵ is —(C₁₋₈)alkyl or —X³R²⁶, wherein X³ is as defined above and R²⁶ is selected from a group consisting of (C₃₋₁₀)cycloalkyl, hetero(C₅₋₁₀)cycloalkyl, (C₆₋₁₀)aryl, hetero(C₅₋₁₀) aryl, (C₉₋₁₀)bicycloaryl and hetero(C₈₋₁₀) bicycloaryl; wherein any of the (C₃₋₁₀)cycloalkyl, hetero(C₅₋₁₀)cycloalkyl, (C₆₋₁₀)aryl, hetero(C₅₋₁₀) aryl, (C₉₋₁₀)bicycloaryl and hetero(C₈₋₁₀) bicycloaryl contained within R³, R²², R²⁴ and R²⁶ may be substituted further with up to five substituents selected from a group consisting of (C₁₋₆)alkyl, (C₁₋₆)alkylidene, cyano, halo, nitro, halo-substituted (C₁₋₃)alkyl, —X³NR¹⁶R¹⁶, —X³NR¹⁶C(O)OR¹⁶, —X³NR¹⁶C(O)NR¹⁶R¹⁶, —X³NR¹⁶C(NR¹⁶)NR¹⁶R¹⁶, —X³OR¹⁶, —X³SR¹⁶, —X³C(O)OR¹⁶, —X³C(O)NR¹⁶R¹⁶, —X³S(O)₂NR¹⁶R¹⁶, —X³P(O)(OR⁸)OR¹⁶, —X³OR⁵², —X³CONR⁸R⁵², —X³C(O)R¹⁶, —X³SO₂NR⁸R⁵², —X³S(O)R¹⁷, —X³OP(O)(OR⁸)OR¹⁶, —X³NR¹⁶C(O)R¹⁷, —X³S(O)₂R¹⁷ and —X³C(O)R¹⁶, wherein:
X³ is a bond or (C₁₋₆)alkylene, R⁵² represents —CH₂CH₂—N(CH₂CH₂OH)₂, —CH(CH₃) CH₂N(CH₃)₂, —CH₂CH₂OH, —CH₂CH₂N (CH₃)₂ or —CH₂CN, R¹⁶ at each occurrence independently is selected from a group consisting of hydrogen, (C₁₋₃)alkyl or halo-substituted (C₁₋₃)alkyl and R¹⁷ is —(C₁₋₃)alkyl or halo-substituted (C₁₋₃)alkyl; and
the N-oxide derivatives, prodrug derivatives, protected derivatives, individual isomers and mixtures of isomers, and pharmaceutically acceptable salts thereof, with the proviso that only one of $R^3$, $R^{22}$, $R^{24}$ and $R^{26}$ represents a fused bicyclic ring structure; which process comprises:

(A) reacting a compound of Formula 2:

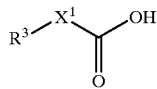

2 a with a compound of the formula $NH_2CR^1R^2CN$, wherein $X^1$, $R^1$, $R^2$ and $R^3$ are as defined above; and (B) optionally converting a compound of Formula I into a pharmaceutically acceptable salt;
(C) optionally converting a salt form of a compound of Formula I to non-salt form;
(D) optionally converting an unoxidized form of a compound of Formula I into a pharmaceutically acceptable N-oxide;
(E) optionally converting an N-oxide form of a compound of Formula I its unoxidized form;
(F) optionally resolving an individual isomer of a compound of Formula I from a mixture of isomers;
(G) optionally converting a non-derivatized compound of Formula I into a pharmaceutically prodrug derivative; and
(H) optionally converting a prodrug derivative of a compound of Formula I to its non-derivatized form.

Pharmacology and Utility

The compounds of this invention are cysteine protease inhibitors. In particular the compounds of this invention inhibit the activity of cathepsins B, L, K and/or S and, as such, are useful for treating diseases in which cathepsin B, L, K and/or S activity contributes to the pathology and/or symptomatology of the disease. For example, the compounds of this invention are useful in treating tumor invasion and metastasis, in particular as anti-angiogenic agents, rheumatoid arthritis, osteo arthritis, pneumocystis carinii, acute pancreatitis, inflammatory airway disease and bone and joint disorders. Furthermore, the compounds of this invention are useful in treating bone resorption disorders, e.g., osteoporosis. The compounds of this invention also are useful in treating autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis. The compounds of this invention also are useful in treating allergic disorders, including, but not limited to asthma; and allogeneic immune responses, including, but not limited to, organ transplants or tissue grafts. In particular, the compounds of this invention are useful in treating osteoporosis in humans by inhibition of cathepsin K, particularly in treating post-menopausal women.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease induced hydrolysis of a peptide based substrate. Details of assays for measuring protease inhibitory activity are set forth in Examples 11, 12, 13 and 14, infra.

Nomenclature

The compounds of Formula I and the intermediates and starting materials used in their preparation are named in accordance with IUPAC rules of nomenclature in which the characteristic groups have decreasing priority for citation as the principle group as follows: acids, esters, amides, etc. or by using the "Autonom", a Beilstein Commander 2.1 Application, distributed by Beilstein. For example, a compound of Formula I in which:

$X^1$ is $CR^6R^7$, $R^1$ and $R^2$ are hydrogen, $R^3$ is biphenyl-3-yl, $R^6$ is hydrogen and $R^7$ is 2-methylpropyl is named 2-biphenyl-3-yl-N-cyanomethyl-4-methylpentanamide; or 2-biphenyl-3-yl-4-methyl-pentanoic acid cyanomethyl-amide.

Administration and Pharmaceutical Compositions

In general, compounds of Formula I will be administered in therapeutically effective amounts via any of the usual and acceptable modes known in the art. A therapeutically effective amount may vary widely depending on the severity of the disease, the age and relative health of the subject, the potency of the compound used and other factors. For example, therapeutically effective amounts of a compound of Formula I may range from 0.1 micrograms per kilogram body weight (μg/kg) per day to 10 milligram per kilogram body weight (mg/kg) per day, typically 1 μg/kg/day to 1 mg/kg/day. Therefore, a therapeutically effective amount for a 80 kg human patient may range from 10 μg/day to 100 mg/day, typically 0.1 mg/day to 10 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, or the like). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01% w to 10% w, preferably 0.3% w to 1% w, of active ingredient with the remainder being the excipient or excipients. Preferably the pharmaceutical compositions is administered in a single unit dosage form for continuous treatment or in a single unit dosage form ad libitum when relief of symptoms is specifically required. Representative pharmaceutical formulations containing a compound of Formula I are described in Example 15.

The compounds of Formula I can be administered alone or in combination with other compounds of Formula I or in combination with one or more other active ingredient(s). For example, the compounds of Formula I can be administered in combination with a therapeutically active amount of a bisphosphonic acid or acid ester derivative or any pharmaceutically acceptable salt thereof. Suitable bisphosphonic acids and acid ester derivatives include compounds corresponding to the following formula:

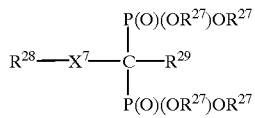

wherein $X^7$ is a bond or $(C_{1-7})$alkylene, each $R^{27}$ independently is hydrogen or $(C_{1-30})$alkyl, $R^{28}$ and $R^{29}$ are selected independently from a group consisting of hydrogen, halo, optionally substituted $(C_{1-30})$alkyl, $(C_{3-30})$cycloalkyl, hetero $(C_{5-30})$cycloalkyl, optionally substituted $(C_{6-10})$aryl, hetero $(C_{6-10})$aryl, $NR^{30}R^{30}$, $OR^{30}$, $SR^{30}$, wherein each $R^{30}$ independently is hydrogen, $(C_{1-10})$alkyl, $(C_{3-10})$cycloalkyl, optionally substituted $(C_{6-10})$aryl, provided that both $R^{28}$ and $R^{29}$ are not selected from hydrogen or hydroxy when $X^7$ is a bond; or $R^{28}$ and $R^{29}$ taken together form $(C_{2-9})$alkylene; wherein $(C_{3-10})$cycloalkyl includes adamantyl and the like, hetero$(C_{5-10})$cycloalkyl includes pyrrolidinyl and the like, $(C_{6-10})$aryl includes phenyl and naphthyl, and hetero$(C_{6-10})$ aryl includes quinolyl, isoquinolyl, pyridyl, furyl, imidazolyl, imidazopyridyl and the like.

Instances wherein $R^{28}$ and/or $R^{29}$ are substituted $(C_{1-30})$ alkyl may include, but are not limited to, $(C_{1-30})$alkyl substituted by hetero$(C_{5-10})$cycloalkyl, $(C_{6-10})$aryl, hetero $(C_{6-10})$aryl, $NR^{31}R^{31}$, $OR^{31}$ and $SR^{31}$, wherein each $R^{31}$ is independently hydrogen or $(C_{1-10})$alkyl; wherein hetero$(C_{5-10})$cycloalkyl includes pyrrolidinyl and the like, $(C_{6-10})$aryl includes phenyl and naphthyl, and hetero$(C_{6-10})$ aryl includes quinolyl, isoquinolyl, pyridyl, furyl, imidazolyl, imidazopyridyl and the like. Suitable optionally substituted aryl groups include, but are not limited to, halo-substituted phenyl.

A non-limiting class of bisphosphonic acids and acid ester derivatives thereof suitable for administration in combination with compounds of Formula I include those in which $R^{28}$ is selected from the group consisting of hydrogen, hydroxy or halo, and $R^{29}$ is selected from the group consisting of optionally substituted $(C_{1-30})$alkyl, halo and $SR^{30}$, wherein $R^{30}$ is $(C_{1-10})$alkyl or phenyl.

A non-limiting subclass of bisphosphonic acids and acid ester derivatives thereof suitable for administration in combination with compounds of Formula I include those in which $R^{28}$ is selected from the group consisting of hydrogen, hydroxy and chloro and $R^{29}$ is selected from the group consisting of optionally substituted $(C_{1-30})$alkyl, chloro and chlorophenylthio.

A non-limiting example of a bisphosphonic acid suitable for administration in combination with compounds of Formula I include that in which $X^7$ is a bond, each $R^{27}$ is hydrogen, $R^{28}$ is hydroxy and $R^{29}$ is 3-aminopropyl, namely 4-amino-1-hydroxybutylidene-1,1-bisphosphonic acid (aka alendronic acid), or the monosodium trihydrate salt thereof, namely 4-amino-1-hydroxybutylidene-1,1-bisphosphonate monosodium trihydrate (aka alendronate monosodium trihydrate), described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which patents are incorporated by reference herein in their entirety.

Further non-limiting examples of bisphosphonic acids suitable for administration in combination with compounds of Formula I include the following:

cycloheptylaminomethylene-1,1-bisphosphonic acid (aka cimadronic acid), described in U.S. Pat. No. 4,970,335, to Isomura et al., issued Nov. 13, 1990;

1,1-dichloromethylene-1,1-diphosphonic acid (aka clodronic acid) and the disodium salt thereof, namely clodronate disodium, described in Belgium Patent 672,205 (1966) and *J. Org. Chem* 32, 4111 (1967);

1-hydroxy-3-pyrrolidin-1-ylpropylidene-1,1-bisphosphonic acid (aka EB-1053);

1-hydroxyethylidene-1,1-diphosphonic acid (aka etidronic acid);

1-hydroxy-3-(N-methyl-N-pentylamino)propylidene-1,1-bisphosphonic acid (aka ibandronic acid), described in U.S. Pat. No. 4,927,814, issued May 22, 1990;

6-amino-1-hydroxyhexylidene-1,1-bisphosphonic acid (aka neridronic acid);

3-(dimethylamino)-1-hydroxypropylidene-1,1-bisphosphonic acid (aka olpadronic acid);

3-amino-1-hydroxypropylidene-1,1-bisphosphonic acid (aka pamidronic acid);

2-pyrid-2-ylethylidene-1,1-bisphosphonic acid (aka piridronic acid), described in U.S. Pat. No. 4,761,406;

1-hydroxy-2-pyrid-3-ylethylidene-1,1-bisphosphonic acid (aka risedronic acid);

4-chlorophenylthiomethylenebisphosphonic acid (aka tiludronic acid), described in U.S. Pat. No. 4,876,248, to Breliere et al., Oct. 24, 1989; and 1-hydroxy-2-(1H-imidazol-1-yl)ethylidene-1,1-bisphosphonic acid (aka zoledronic acid); all of which patents and other documents referred to above are incorporated by reference herein in their entirety.

A non-limiting subclass of bisphosphonic acids suitable for administration in combination with compounds of Formula I include those selected from the group consisting of alendronic acid, cimadronic acid, clodronic acid, tiludronic acid, etidronic acid, ibandronic acid, risedronic acid, piridronic acid, pamidronic acid, zolendronic acid, pharmaceutically acceptable salts thereof, and mixtures thereof. A further example of a bisphosphonic acid suitable for administration in combination with compounds of Formula I is alendronic acid or a pharmaceutically acceptable salt thereof, and mixtures thereof. A further non-limiting example is alendronate monosodium trihydrate.

Compounds of Formula I can be administered in combination with a therapeutically active amount of an estrogen receptor agonist. Non-limiting examples of estrogen receptor agonists suitable for administration in combination with the compounds of Formula I include naturally occurring estrogens such as estradiol, estrone and estroil, or synthetic estrogen receptor agonists such as [6-hydroxy-2-(4-hydroxyphenyl)benzo[b]thien-3-yl][4-(2-piperidin-1-ylethoxy)phenyl]methanone (aka raloxifene) and {2-[4-(1,2-diphenylbut-1-enyl)phenoxy]ethyl}dimethylamine (aka tamoxifen). A non-limiting subclass of estrogen receptor agonists suitable for administration in combination with the compounds of Formula I include estrogen receptor partial agonists (i.e., estrogen receptor agonists with mixed agonist/antagonist properties), sometimes referred to as estrogen receptor modulators. Estrogen receptor partial agonists can exert tissue-selective estrogen agonist effects. Tamoxifen, for example, selectively exerts an estrogen agonist effect on the bone, in humans. Additional suitable estrogen receptor partial agonists are described in Tissue-Selective Actions Of Estrogen Analogs, Bone Vol. 17, No. 4, October 1995, 181S-190S. Certain 3-[4-(2-phenylindol-1-ylmethyl) phenyl]acrylamides, described in U.S. Pat. No. 5,985,910 to Miller et al., Nov. 16, 1999; benzothiphene compounds, described in U.S. Pat. No. 5,985,897 to Meuhl et al., Nov. 16, 1999; naphthyl compounds, described in U.S. Pat. No. 5,952,350 to Cullinan et al., Sep. 14, 1999; substituted benzothiophene compounds, described in U.S. Pat. No. 5,962,475 to Schmid et al., Oct. 4, 1999, are suitable estrogen receptor partial agonists for administration with the compounds of Formula I; all of which patents and other documents referred to above are incorporated by reference herein in their entirety.

More particularly a pharmaceutical composition of this invention may comprise a therapeutically effect amount of a compound of Formula I in combination with one or more active ingredient(s) selected from the group consisting of (i) a therapeutically effect amount of a bisphosphonic acid or acid ester thereof or a pharmaceutically acceptable salt thereof and (ii) a therapeutically effect amount of an estrogen receptor agonist or a pharmaceutically acceptable salt thereof; and one or more pharmaceutically acceptable excipient(s). Non-limiting examples of such bisphosphonic acids include 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof; particularly 1,1-dichloromethylene-1,1-diphosphonic acid or a pharmaceutically acceptable salt thereof and preferably 1,1-dichloromethylene-1,1-diphosphonate monosodium trihydrate.

Chemistry

Compounds of Formula I can be prepared by proceeding as in the following Reaction Scheme 1:

Reaction Scheme 1

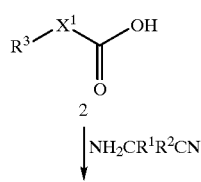

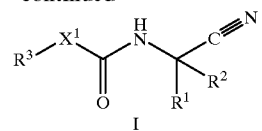

I in which $X^1$, $R^1$, $R^2$ and $R^3$ are as defined in the Summary of the Invention.

Compounds of Formula I can be prepared by condensing an acid of Formula 2 with an aminoalkanonitrile of the formula $NH_2CR^1R^2CN$. The condensation reaction can be effected with an appropriate coupling agent (e.g., benzotriazol-1-yloxytrispyrrolidinophosphonium hexafluorophosphate (PyBOP®), 1-(3-dimethylaminopropyl)-3-ethylcarbodiimide hydrochloride (EDCI), O-benzotriazol-1-yl-N,N,N',N'-tetramethyluronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), or the like) and non-nucleophillic base (e.g., N-methylmorpholine, triethylamine, or the like, or any suitable combination thereof) in a suitable solvent (N-methylpyrrolidinone, or the like) at ambient temperature and requires 3 to 10 hours to complete the reaction. A detailed description for the synthesis of a compound of Formula I by the processes in Reaction Scheme 1 is set forth in Examples 7, 8 and 9, infra.

Compounds of Formula I in which $R^3$ is substituted phenyl can be prepared by proceeding as in the following Reaction Scheme 2:

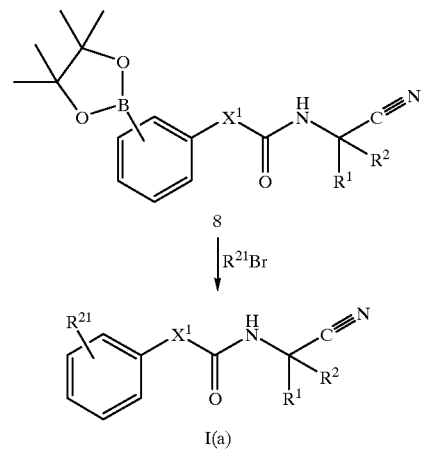

in which $X^1$, $R^2$ and $R^{21}$ are as defined in the Summary of the Invention.

Compounds of Formula I in which $R^3$ is substituted phenyl can be prepared by reacting a boronic ester of Formula 8 with a compound of the formula $R^{21}Br$. The reaction is carried out in a suitable solvent (e.g., N,N-dimethylformamide (DMF), 2-propanol, or the like) in the presence of sodium bicarbonate and palladium(II) chloride under nitrogen at 80 to 85° C. and requires 1 to 5 hours to complete the reaction. A detailed description for the synthesis of a compound of Formula I by the processes in Reaction Scheme 2 is set forth in Example 10, infra.

Compounds of Formula 2 in which $X^1$ is $CHR^7$ can be prepared by reacting a compound of Formula 3:

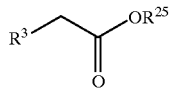

with a compound of the formula R⁷L in which L is a leaving group, R²⁵ is hydrogen or (C₁₋₆)alkyl and R³ and R⁷ are as defined in the Summary of the Invention for Formula I. The reaction is carried out in a suitable solvent (e.g., dimethoxyethane, dioxane, ether, hexane, tetrahydrofuran (THF), or the like) and in the presence of a strong non-nucleophillic base (e.g., lithium diisopropylamide (LDA), sodium hexamethyldisilazide (NaHMDS), potassium hexamethyldisilazide (KHMDS), potassium tert-butoxide, sodium methoxide, tert-butyl lithium, or the like) at approximately −78° C. and requires 1 to 2 hours to complete the reaction.

Compounds of Formula 2 in which R³ is optionally substituted 4-phenylthiazol-2-yl can be prepared by reacting a compound of Formula 4:

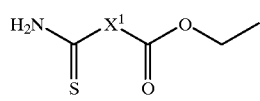

with a compound of Formula RC(O)CH₂L in which L is a leaving group and R is optionally substituted phenyl to provide a corresponding 2-(4-phenylthiazol-2-yl)acetate or 4-phenylthiazol-2-ylcarbamate and then hydrolyzing to the corresponding compound of Formula 2. The reaction with the compound of Formula 4 is carried out in a suitable solvent (e.g., ethanol, acetonitrile, THF, methanol, DMF, or the like) at reflux and requires 0.5 to 1 hour to complete the reaction. Hydrolysis can be effected by treating the ester with base (e.g., sodium hydroxide, lithium hydroxide, or the like) in a suitable solvent (methanol, THF/water, DMF/water, acetonitrile/water, or the like) for 2 to 6 hours.

Chiral compounds of Formula 2 in which X¹ is CHR⁷ can be prepared by condensing a compound of Formula 5:

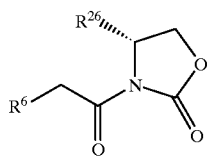

with a compound of the formula R³L, wherein L is a leaving group, R²⁶ is a chiral auxiliary, e.g., isopropyl or benzyl, and X¹, R³ and R⁷ are as defined in the Summary of the Invention, to provide a compound of Formula 6:

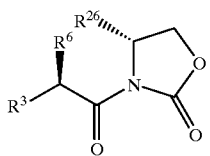

and then converting the compound of Formula I to the corresponding acid. The condensation reaction is carried out is a suitable solvent (e.g., THF, dimethoxymethane, ether, or the like) and in the presence of a strong non-nucleophilic, hydrocarbon-soluble base (e.g., NaHMDS, KHMDS, or the like) at about −78° C. to about −10° C. and requires approximately 1 hour for the reaction to complete the reaction. Conversion to the corresponding acid can be effected by treating the compound of Formula 6 with lithium hydroxide monohydrate and hydrogen peroxide in a suitable solvent (e.g., THF/water, or the like) at ambient temperature for 1 to 16 hours.

Compounds of Formula 4 can be prepared by reacting a corresponding 2-cyanoacetate or cyanocarbamate with hydrogen sulfide gas. The reaction is carried out in a suitable solvent (e.g., pyridine, triethylamine, dioxane, or the like) and in the presence of a suitable non-nucleophillic base (e.g., triethylamine, pyridine, diisopropylethylamine, or the like) at approximately 0° C. and requires 3 to 5 hours to complete the reaction. A detailed description for the synthesis of a compound of Formula 2 in which R³ is optionally substituted 4-phenylthiazol-2-yl is set forth in Example 4, infra.

Compounds of Formula 2 in which R³ is 2-substituted thiazol-4-yl can be prepared by reacting a compound of Formula 7:

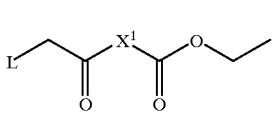

with a compound of the formula RC(S)NH₂, in which L is a leaving group, R is an appropriate substituent and X¹ is as described in the Summary of the Invention, to provide a corresponding acetate or carbamate and then hydrolyzing to the corresponding compound of Formula 2. The reaction with the compound of Formula 7 is carried out in a suitable solvent (e.g., ethanol, methanol, DMF, dioxane, or the like) at reflux and requires 1 to 2 hours to complete the reaction. Hydrolysis can be effected by treating the ester with base (e.g., sodium hydroxide, lithium hydroxide, or the like) in a suitable solvent (methanol, THF/water, DMF/water, acetonitrile/water, or the like) for 2 to 6 hours.

Compounds of Formula 7 in which L is bromo can be prepared by treating a corresponding acetylacetate or acetylcarbamate with bromine in a suitable solvent (e.g., methylene chloride, chloroform, carbon tetrachloride, chlorobenzene, or the like) at approximately 0° C. for 12 to 15 hours. Detailed descriptions for the synthesis of compounds of Formula 2 are set forth in Examples 1, 2, 3, 4, 5 and 6, infra.

Additional Processes for Preparing Compounds of Formula I

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form may be converted to the corresponding free base by treating with a suitable base (e.g., ammonium hydroxide solution, sodium hydroxide, or the like). A compound of Formula I in a base addition salt form can be converted to the corresponding free acid by treating with a suitable acid (e.g., hydrochloric acid, or the like).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as methylene chloride) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g. sulfur, sulfur dioxide, triphenyl phosphine, lithium borohydride, sodium borohydride, phosphorus trichloride, tribromide, or the like) in a suitable organic solvent (e.g., acetonitrile, ethanol, aqueous dioxane, or the like) at 0 to 80° C.

Prodrug derivatives of the compounds of Formula I can be made by means known to those of ordinary skill in the art (e.g., for further details see Saulnier et al. (1994), *Bioorganic and Medicinal Chemistry Letters.* 4: 1985). For example, appropriate drugs can be prepared by reacting a non-derivatized compound of Formula I with a suitable carbamylating agent (e.g., 1,1-acyloxyalkylcarbonochloridate, para-nitrophenyl carbonate, or the like).

Protected derivatives of the compounds of Formula I can be made by means known to those of ordinary skill in the art. A detailed description of the techniques applicable to the creation of protective groups and their removal can be found in T. W. Greene, *Protective Groups in Organic Synthesis,* John Wiley & Sons, Inc. 1981.

Compounds of Formula I can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds of Formula I, dissociable complexes are preferred (e.g., crystalline diastereoisomeric salts). Diastereomers have distinct physical properties (e.g., melting points, boiling points, solubilities, reactivity, and the like) and can be readily separated by taking advantage of these dissimilarities. The diastereomers can be separated by chromatography or, preferable, by separation/resolution techniques based upon differences in solubility. The optically pure enatiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

In summary, the compounds of Formula I are made by a process which comprises:

(A) reacting a compound of Formula 2:

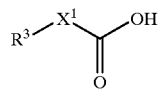

with a compound of the formula $NH_2CR^1R^2CN$, wherein $X^1$, $R^1$, $R^2$ and $R^3$ are as defined in the Summary of the Invention; and (B) optionally converting a compound of Formula I into a pharmaceutically acceptable salt;

(C) optionally converting a salt form of a compound of Formula I to non-salt form;

(D) optionally converting an unoxidized form of a compound of Formula I into a pharmaceutically acceptable N-oxide;

(E) optionally converting an N-oxide form of a compound of Formula I its unoxidized form;

(F) optionally resolving an individual isomer of a compound of Formula I from a mixture of isomers;

(G) optionally converting a non-derivatized compound of Formula I into a pharmaceutically prodrug derivative; and (H) optionally converting a prodrug derivative of a compound of Formula I to its non-derivatized form.

EXAMPLES

Example 1

2-Cyclohexylmethyl-N-phenethylmalonamic acid, a compound of Formula 2 in which $R^3$ is phenethylcarbamoyl and $X^1$ is —$CHR^7$— wherein $R^7$ is cyclohexylmethyl A solution comprised of sodium (6.9 g, 0.3 mmol) in ethanol (250 mL) was treated sequentially with diethyl malonate (53.127 g, 0.3 mol) and then cyclohexylmethyl bromide (46 mL, 0.33 mol) at ambient temperature. The mixture was heated to 70° C. and stirred for approximately 12 hours. The mixture was cooled and solvent was removed by evaporation. The residue was diluted with ice water and the dilution was extracted with ethyl acetate (4x). The combined extracts were washed with water (4x) and brine, dried ($MgSO_4$) and concentrated to provide diethyl 2-cyclohexylmethylmalonate.

A solution comprised of diethyl 2-cyclohexylmethylmalonate (12.817 g, 50 mmol) in ethanol (100 mL) was treated with a solution of comprised of lithium hydroxide (1.198 g, 50 mmol) in water (50 mL) and the mixture was stirred for approximately 12 hours at ambient temperature. Solvent was removed by evaporation and the residue was diluted with water (50 mL). The dilution was extracted with diethyl ether (2x). The aqueous layer was cooled to 0° C., acidified to pH 1.5 with 1N hydrochloric acid (50 mL), saturated with solid sodium chloride and then extracted with ethyl acetate (2x). The combined ethyl acetate extracts were dried ($MgSO_4$) and concentrated. The residue was dried to provide 3-cyclohexyl-2-ethoxycarbonylpropionic acid (8.52 g, 37 mmol) as an oil.

A solution comprised of 3-cyclohexyl-2-ethoxycarbonylpropionic acid (8.52 g, 37 mmol) in ethyl acetate (80 mL) was cooled to 0° C. was treated sequentially with 2 drops of DMF and oxalyl chloride (3.93 mL) added dropwise over five minutes. The mixture was allowed to warm slowly and after approximately 2 hours concentrated to provide ethyl 2-chlorocarbonyl-3-cyclohexylpropionate.

A mixture of ethyl 2-chlorocarbonyl-3-cyclohexylpropionate (2.65 mmol), phenethylamine (0.376 mL, 3 mmol) and N-methylmorpholine (0.44 mL, 4 mmol) in ethyl acetate (6 mL) was cooled to between −20 and −10° C. and stirred for 15 minutes. The mixture was allowed to warm to room temperature, stirred for approximately 12 hours and then diluted with ethyl acetate (5 mL) and ice (5 mL). The organic layer was separated, washed with cold 0.05 N hydrochloric acid, sodium bicarbonate solution and brine, dried ($MgSO_4$) and concentrated to provide ethyl 2-cyclohexylmethyl-N-phenethylmalonamate (366 mg, 1.106 mmol).

A solution comprised of ethyl 2-cyclohexylmethyl-N-phenethylmalonamate (366 mg, 1.106 mmol) in ethanol (10 mL) was treated with 1N aqueous sodium hydroxide (1.3 mL) for 2.5 hours and then diluted with water (30 mL) and brine (10 mL). The dilution was extracted with diethyl ether (3×30 mL). The aqueous layer was cooled to 0° C., acidified with 1N hydrochloric acid (2 mL) and extracted with ethyl acetate (3×30 mL). The combined ethyl acetate extracts were washed with brine, dried ($MgSO_4$) and concentrated to provide 2-cyclohexylmethyl-N-phenethyhnalonamic acid (138 mg, 0.45 mmol).

Example 2

2-Biphenyl-3-yl-4-methylpent-4-enoic acid, a compound of Formula 2 in which $R^3$ is bipheny-3-yl and $X^1$ is —$CHR^7$— wherein $R^7$ is 2-methylprop-3-enyl A solution of LDA (2.2 mL, 2.0 M in THF) in THF (20 mL) was cooled to 0° C. and then treated with biphenyl-3-ylacetic acid (0.212 g, 1.0 mmol). The mixture was stirred for 40 minutes, cooled to −78° C. and then treated with 3-bromo-2-methylpropene (135 µL, 1.3 mmol). The mixture was stirred for 1 hour, treated with 1 M hydrochloric acid (5 mL) and then diluted with ethyl acetate (50 mL). The organic layer was separated washed with water, brine, dried ($MgSO_4$) and concentrated. Product was purified from the residue by flash column on silica gel (60° A) with 33% ethyl acetate in hexane to provide 2-biphenyl-3-yl-4-methylpent-4-enoic acid (250 mg, 0.93 mmol). $^1$H NMR (DMSO-$d_6$): 1.71 (s, 3H), 2.52 (m, 2H), 3.68 (dd, 1H), 4.75 (m, 2H), 7.08 (d, 1H), 7.28–7.37 (m, 8H). LCMS: 267.1 (M+H$^+$).

Example 3

2-Biphenyl-3-yl-4-methylpentanoic acid, a compound of Formula 2 in which $R^3$ is bipheny-3-yl and $X^1$ is —$CHR^7$— wherein $R^7$ is 2-methylpropyl A mixture of 2-biphenyl-3-yl-4-methylpent-4-enoic acid (250 mg, 0.9 mmol), prepared as in Example 2, and 5% Pd/C (50 mg) in 10 ml of ethanol was hydrogenated (40 psi) for 2 hours. The mixture was filtered and the filtrate concentrated to provide 2-biphenyl-3-yl-4-methylpentanoic acid (250 mg, 0.9 mmol). $^1$H NMR (DMSO-$d_6$): 1.01 (d, 6H), 1.81–1.85 (m, 3H), 3.68 (dd, 1H), 7.08 (d, 1H), 7.24–7.37 (m, 8H). LCMS: 269.1 (M+H$^+$).

Example 4

4-Methyl-2-(4-phenylthiazol-2-yl)pentanoic acid, a compound of Formula 2 in which $R^3$ is 4-phenylthiazol-2-yl and $X^1$ is —$CHR^7$— wherein $R^7$ is 2-methylpropyl A solution comprised of ethyl 2-cyano-4-methylpentanoate (1.69 gm, 10 mmol) in pyridine (10 mL) was treated with triethylamine (3.0 mL). The mixture was cooled to 0° C. and bubbled with hydrogen sulfide gas and stirred for 3 hours. The mixture then was diluted with ethyl acetate (100 mL) and the dilution treated with 0.1 M hydrochloric acid until the aqueous layer was acidic. The organic layer was separated, washed with water and brine, dried ($MgSO_4$) and concentrated. The residue was triturated with 5% ethyl acetate in hexane (10 mL) to provide ethyl 4-methyl-2-thiocarbamoylpentanoate (2.01 gm, 10 mmol). $^1$H NMR (DMSO-$d_6$): 1.01 (d, 6H) 1.30 (t, 3H), 1.62 (m, 2H), 1.71 (m, 1H), 2.33 (m, 1H), 4.12 (q, 2H), 7.85 (m, 2H).

A solution comprised of ethyl 4-methyl-2-thiocarbamoylpentanoate (410 mg, 2 mmol) in ethanol (5 mL) was treated with 2-bromo-1-phenylethanone (400 mg, 2 mmol). The mixture was refluxed for 30 minutes and concentrated to provide ethyl 4-methyl-2-(4-phenylthiazol-2-yl)pentanoate as a crude product. The crude product was dissolved in methanol (5 mL, tech. grade) and the solution was treated with sodium hydroxide (100 mg, 2.5 mmol). The mixture was stirred for 2 hours and diluted with 0.1 M hydrochloric acid solution. The dilution was extracted with ethyl acetate (25 mL) and the extract was washed with water and brine, dried ($MgSO_4$) and concentrated. Product was purified from the residue by flash column on silica gel (60° A) with 33% ethyl acetate in hexane to provide 4-methyl-2-(4-phenylthiazol-2-yl)pentanoic acid (500 mg, 1.8 mmol). Rf 0.33. $^1$H NMR (DMSO-$d_6$): 0.96 (d, 6H), 1.71–1.79 (m, 3H), 3.61 (m, 1H), 7.12 (s, 1H), 7.32–7.41 (m, 5H). LCMS: 275.91 (M+H$^+$).

Example 5

4-Methyl-2-(2-phenylthiazol-4-yl)pentanoic acid, a compound of Formula 2 in which $R^3$ is 2-phenythiazol-4-yl and $X^1$ is —$CHR^7$— wherein $R^7$ is 2-methylpropyl A solution comprised of ethyl 2-acetyl-4-methylpentanoate (1.86 gm, 10 mmol) in chloroform (20 mL) was cooled to 0° C. and treated with bromine (0.6 mL, 11.0 mmol in 10 mL chloroform). The mixture was stirred for approximately 12 hours and then concentrated to provide ethyl 2-bromoacetyl-4-methylpentanoate as a crude product.

A solution comprised of ethyl 2-bromoacetyl-4-methylpentanoate (0.264 gm, 1 mmol) in ethanol (5 mL) was treated with thiobenzamide (0.15 gm, 1.1 mmol). The mixture was heated at refluxed for 1 hour and concentrated to provide ethyl 4-methyl-2-(2-phenylthiazol-4-yl) pentanoate as a crude product.

A solution comprised of the ethyl 4-methyl-2-(2-phenylthiazol-4-yl)pentanoate in methanol (5 mL) was treated with sodium hydroxide (0.1 gm, 2 mmol). The mixture was stirred for 4 hours, basified with 0.1 M sodium hydroxide solution, washed with ethyl acetate (10 mL), acidified and extracted with ethyl acetate (50 mL). The extract was washed with water, dried ($MgSO_4$) and concentrated. Product was purified from the residue by flash chromatography on silica gel (60° A) with 33% ethyl acetate in hexane as an eluent to provide 4-methyl-2-(2-phenylthiazol-4-yl)pentanoic acid (200 mg, 1.44 mmol). Rf 0.41. $^1$H NMR (DMSO-$d_6$): 1.01 (m, 6H), 1.61–1.79 (m, 3H), 3.63 (m, 1H), 7.04 (d, 1H), 7.22–7.34 (m, 5H). LCMS: 276.1 (M+H$^+$).

Example 6

2-Cyclohexylmethyl-4-morpholin-4-yl-4-oxobutyric acid, a compound of Formula 2 in which $R^3$ is morpholin-2-ylcarbonylmethyl and $X^1$ is —$CHR^7$— wherein $R^7$ is cyclohexylmethyl A solution of 3-cyclohexylpropanoic acid (9.49 g, 60.7 mmol) in THF (100 mL) was cooled to −78° C. in a cooling bath and then treated with triethylamine (15.14 mL, 108 mmol) and pivaloyl chloride (11.6 mL, 94 mmol) to provide "Mixture A." The cooling bath was removed and Mixture A was stirred at 0° for 1 hour. A solution of 4-(S)-isopropylisoxazolidinone (10.55 g, 81.7 mmol) in THF (100 mL) was cooled to −45° C. and then treated with butyl-lithium (51.1 mL of a 1.6M hexane solution), forming a thick slurry as "Mixture B." Mixture B was allowed to warm to 0° C. over 1 hour. Mixture A was cooled to −78° C. and then Mixture B was added to the Mixture A. The cooling bath was removed and the combine mixture was permitted to warm to ambient temperature. The mixture remained at ambient temperature for 1 hour and then was diluted with 0.25 M hydrochloric acid (200 mL). The dilution was extracted with ethyl acetate (200 mL) and the extract was washed with saturated aqueous sodium bicarbonate (200 mL) and brine (200 mL), dried over $MgSO_4$, filtered, and evaporated to dryness. Product was purified from the residue by chromatography on silica gel, using 0–20% ethyl acetate/hexane as eluent to provide (S)-3-cyclohexylpropionyl-4-isopropyloxazolidin-2-one (17.2 g). MS (M+1): 268.

A solution of sodium hexamethyldisilazide (92.4 mL of a 0.6M toluene solution, Aldrich) in THF (70 mL) was cooled to −78° C. and then treated with a solution of (S)-3-cyclohexylpropionyl-4-isopropyloxazolidin-2-one (10.5 g, 39.3 mmol) in THF (30 mL) added dropwise over 10 minutes. The mixture was stirred for 1 hour and then treated with a solution of tert-butylbromoacetate (9.75 mL, 50 mmol) in THF (20 mL) added dropwise. The mixture was stirred for 1 hour, while warming to −10° C. The mixture reaction was diluted with 1M hydrochloric acid (100 mL) and the dilution was extracted with ethyl acetate (200 mL). The extract was washed with saturated aqueous sodium bicarbonate (100 mL) and brine (100 mL), dried ($MgSO_4$), filtered and concentrated to dryness. The residue was dissolved in hexane and product was crystallized out to provide tert-butyl 3-cyclohexylmethyl-4-(4-isopropyl-2-oxooxazolidin-3-yl)-4-oxobutyrate (9.09 g, 61%). MS (M+1): 382.

A solution of tert-butyl 3-cyclohexylmethyl-4-(4-isopropyl-2-oxooxazolidin-3-yl)-4-oxobutyrate (2.90 g, 7.6 mmol) in methylene chloride (10 mL) was treated with trifluoroacetic acid (4.83 g, 42.5 mmol) and the mixture was stirred at ambient temperature for 3 hours. The solvent and excess acid were removed by evaporation at reduced pressure. The residue was dissolved in ether/hexane and product was crystallized out to provide 3-cyclohexylmethyl-4-(4-isopropyl-2-oxooxazolidin-3-yl)-4-oxobutyric acid (2 g, 81%). MS (M+1): 326.

A mixture of 3-cyclohexylmethyl-4-(4-isopropyl-2-oxooxazolidin-3-yl)-4-oxobutyric acid (2.00 g, 6.14 mmol) and HBTU (2.56 g, 6.76 mmol) in DMF (20 mL) were treated with morpholine (0.591 mL, 6.76 mmol) and N-methylmorpholine (0.811 mL, 7.37 mmol). The mixture was stirred overnight at ambient temperature and then partitioned between 4:1:2:3 ethyl acetate/THF/water/brine (100 mL total). The organic phase was washed with 1M hydrochloric acid, saturated aqueous sodium bicarbonate and brine (50 mL each), dried ($MgSO_4$) filtered and concentrated to dryness. The residue dissolved in ethyl acetate/hexane and product was crystallized out to provide 2-cyclohexylmethyl-1-(4-isopropyl-2-oxooxazolidin-3-yl)-4-morpholin-4-ylbutane-1,4-dione (1.63 g). MS (M+1): 395.

A solution of 2-cyclohexylmethyl-1-(4-isopropyl-2-oxooxazolidin-3-yl)-4-morpholin-4-yl-butane-1,4-dione (1.63 g, 4.13 mmol) in THF (20 mL) was treated with lithium hydroxide monohydrate (0.226 g, 5.37 mmol) and hydrogen peroxide (2 mL of a 30% solution) and the mixture was stirred overnight at ambient temperature. The mixture was treated with sodium nitrite (1.3 g) and stirred for an additional 30 minutes. The organic solvent was removed under reduced pressure and the residual mixture was diluted with water (30 mL). The dilution was extracted with methylene chloride (3×30 mL) and the aqueous layer was acidified to pH 2 with 1M hydrochloric acid and extracted with dichloromethane (3×20 mL). The combined extracts were dried ($MgSO_4$), filtered and concentrated to dryness to provide 2-cyclohexylmethyl-4-morpholin-4-yl-4-oxobutyric acid (0.56 g, 48%).

Example 7

2-Biphenyl-3-yl-N-cyanomethyl-4-methylpentanamide (Compound 1), a compound of Formula I in which $R^1$ and $R^2$ are hydrogen, $R^3$ is biphenyl-3-yl and $X^1$ is —$CHR^7$— wherein $R^7$ is 2-methylpropyl A solution comprised of 2-biphenyl-3-yl-4-methylpentanoic acid (0.251 mg, 0.91 mmol), prepared as in Example 3, in DMF (5 mL) was treated with aminoacetonitrile (180 mg, 2 mmol), PyBOP (520 mg 1 mmol) and triethylamine (500 µL, 3 mmol). The mixture was stirred for 4 hours and then diluted with water (50 mL) and ethyl acetate (20 mL). The organic layer was separated, washed with 1 M saturated sodium bicarbonate solution, 1 M hydrochloric acid solution, water and brine, dried ($MgSO_4$) and concentrated. The residue was recrystallized from 30% ethyl acetate in hexane to provide 2-biphenyl-3-yl-N-cyanomethyl-4-methylpentanamide (300 mg, 0.89 mmol). $^1$H NMR (DMSO-$d_6$): 1.01 (d, 6H), 1.81–1.85 (m, 3H), 3.73 (dd, 1H), 4.35 (m, 2H), 7.12 (d, 1H), 7.24–7.37 (m, 8H) 8.31 (s, 1H). LCMS: 307.3 (M+H$^+$).

The following compounds of Formula I were prepared by proceeding as in Example 7:

2-biphenyl-4-yl-N-cyanomethyl-4-methylpentanamide (Compound 2); $^1$H NMR (DMSO-$d_6$): 0.93 (d, 6H), 1.71–1.83 (m, 3H), 3.72 (dd, 1H), 4.32 (m, 2H), 7.18–7.24 (m, 4H), 7.31 (d, 2H), 8.31–8.47 (m, 3H), 9.81 (s, 1H), 11(s, 1H); LCMS: 307.1 (M+H$^+$);

N-cyanomethyl-4-methyl-2-[4-(3-pyrid-4-ylureido)phenyl]pentanamide (Compound 3); $^1$H NMR (DMSO-$d_6$): 0.87 (d, 6H), 1.78–1.83 (m, 3H), 3.72 (dd, 1H), 4.32 (m, 2H), 7.18–7.24 (m, 4H), 7.31–7.37 (m, 5H); LCMS: 366.3 (M+H$^+$);

N-cyanomethyl-4-methyl-2-[4-(3-pyrid-4-ylmethylureido)phenyl]pentanamide (Compound 4); $^1$H NMR (DMSO-$d_6$): 0.91 (d, 6H), 1.78–1.83 (m, 3H), 3.62 (dd, 1H), 4.17 (m, 2H), 4.53 (d, 2H), 6.98–7.24 (m, 3H), 7.82 (d, 2H), 8.31–8.81 (m, 4H); LCMS: 380.1 (M+H$^+$);

N-cyanomethyl-4-methyl-2-[4-(3-pyrid-3-ylmethylureido)phenyl]pentanamide (Compound 5); $^1$H NMR (DMSO-$d_6$): 0.96 (d, 6H), 1.71–1.83 (m, 3H), 3.62 (t, 1H), 4.12 (m, 2H), 4.57 (d, 2H), 6.98–7.24 (m, 5H), 7.82 (d, 1H), 8.13 (d, 1H), 8.31–8.81 (m, 4H); LCMS: 379.9 (M+H$^+$);

N-cyanomethyl-4-methyl-2-{3-[3-(3-morpholin-4-ylpropyl)ureido]phenyl}pentanamide (Compound 6); $^1$H NMR (DMSO-$d_6$): 1.01 (d, 6H), 1.65–1.83 (m, 5H), 2.37–2.40 (m, 6H), 3.51–3.60 (m, 6H), 3.71 (t, 1H), 4.12 (m, 2H), 6.98 (d, 1H), 7.20 (m, 1H), 7.46–7.52 (m, 2H), 8.13 (d, 1H), 8.71–8.81 (m, 2H); LCMS: 416.3 (M+H$^+$);

2-morpholin-4-ylethyl 3-(1-cyanomethylcarbamoyl-3-methylbutyl)phenylcarbamate (Compound 7); $^1$H NMR (DMSO-d$_6$): 1.01 (d, 6H), 1.65–1.83 (m, 3H), 2.37–2.40 (m, 6H), 3.51–3.60 (m, 6H), 3.68 (t, 1H), 4.17 (m, 2H), 7.03 (d, 1H), 7.20 (m, 1H), 7.48–7.55 (m, 2H), 8.19 (d, 1H), 8.61–8.67 (m, 2H); LCMS: 403.3 (M+H$^+$);

N-cyanomethyl-4-methyl-2-naphth-1-ylpentanamide (Compound 9); $^1$H NMR (DMSO-d$_6$): 0.91–0.96 (d, 6H), 1.30 (m, 2H), 1.62 (m, 1H), 4.31 (m, 2H), 4.42 (m, 1H), 7.41–7.52 (m, 4H), 7.81–7.91 (m, 3H), 8.43 (d, 1H); LCMS: 279.8 (M+H$^+$);

N-cyanomethyl-4-methyl-2-(2-phenylthiazol-4-yl)pent-4-enamide (Compound 10); $^1$H NMR (DMSO-d$_6$): 1.61 (s, 3H), 2.42–2.62 (m, 2H), 4.11–4.21 (m, 3H), 4.62 (m, 2H), 7.41 (m, 4H), 8.43 (d, 1H); LCMS: 308 (M+H$^+$);

N-cyanomethyl-2-(3-bromophenyl)-4-methylpent-4-enamide (Compound 11); $^1$H NMR (DMSO-d$_6$): 1.91 (s, 3H), 2.30 (m, 1H), 2.62 (m, 1H), 3.61 (m, 1H), 4.17 (s, 2H), 4.52 (m, 2H), 7.31–7.52 (m, 4H), 7.83 (m, 2H), 8.43 (d, 1H); LCMS: 308 (M+H$^+$);

N-cyanomethyl-4-methyl-2-naphth-2-ylpentanamide (Compound 12); $^1$H NMR (DMSO-d$_6$): 1.03 (d, 6H), 1.17 (m, 1H), 1.31 (m, 1H), 1.62 (m, 1H), 3.62 (m, 1H), 4.17 (d, 2H), 7.31–7.42 (m, 3H), 7.61–7.67 (m, 4H), 8.38 (d, 1H); LCMS: 280.1 (M+H$^+$);

N-cyanomethyl-4-methyl-2-(4-phenylthiazol-2-yl) pentanamide Compound 13); $^1$H NMR (DMSO-d$_6$): 0.96–1.08 (m, 6H), 1.31–1.59 (m, 3H), 3.81 (m, 1H), 4.13 (d, 2H), 7.12–7.24 (m, 3H), 7.81 (m, 2H), 8.01 (m, 1H), 9.10 (s, 1H); LCMS: 314.0 (M+H$^+$);

N-cyanomethyl-4-methyl-2-[4-(3-nitrophenyl)thiazol-2-yl]pentanamide (Compound 14); $^1$H NMR (DMSO-d$_6$): 0.84–0.93 (m, 6H), 1.31–1.59 (m, 3H), 3.85 (m, 1H), 4.18 (s, 2H), 7.24 (d, 1H), 8.14 (d, 1H), 8.31 (m, 2H), 8.61 (s, 1H), 9.10 (s, 1H); LCMS: 359.0 (M+H$^+$); and 2-[4-(3-aminophenyl)thiazol-2-yl]-N-cyanomethyl-4-methylpentanamide (Compound 15); $^1$H NMR (DMSO-d$_6$).

Example 8

N-Cyanomethyl-4-methyl-2-(2-phenylthiazol-4-yl) pentanamide (Compound 16), a compound of Formula I in which R$^1$ and R$^2$ are hydrogen, R$^3$ is 2-phenylthiazol-4-yl and X$^1$ is —CHR$^7$— wherein R$^7$ is 2-methylpropyl A solution comprised of 4-methyl-2-(2-phenylthiazol-4-yl)pentanoic acid (150 mg, 0.6 mmol), prepared as in Example 5, in DMF (5.0 mL) was treated with PyBOP (300 mg, 0.7 mmol), aminoacetonitrile hydrochloride (100 mg, 1 mmol) and triethylamine (250 μL, 1.5 mmol). The mixture was stirred for 3 hours and then partitioned between water (20 mL) and ethyl acetate (50 mL). The organic layer was separated and washed with 1 M saturated sodium bicarbonate solution, 1 M hydrochloric acid solution and water, dried (MgSO$_4$) and concentrated. Product was purified from the residue by flash column on silica gel (60° A) with 40% ethyl acetate in hexane to provide N-cyanomethyl-4-methyl-2-(2-phenylthiazol-4-yl)pentanamide (120 mg, 0.46 mmol). Rf 0.30. $^1$H NMR (DMSO-d$_6$): 1.01 (m, 6H), 1.31–1.59 (m, 3H), 3.91 (m, 1H), 4.14 (s, 2H), 7.44 (m, 4H), 7.81 (m, 2H), 8.61 (s, 1H). LCMS: 312.2.0 (M+H$^+$).

The following compounds of Formula I were provided by proceeding as in Example 8:

2-biphenyl-4-yl-N-cyanomethyl-5-methylhexanamide (Compound 17);

2-(1-methylpyrrolidin-2-yl)ethyl 3-(1-cyanomethylcarbamoyl-3-methylbutyl)phenylcarbamate (Compound 18);

N-cyanomethyl-4-methyl-2-(3-thien-3-ylphenyl)pent-4-enamide (Compound 19);

N-cyanomethyl-3-methyl-2-phenylpentanamide (Compound 20);

N-cyanomethyl-4-methyl-2-(2-pyrid-4-ylaminothiazol-4-yl)pentanamide (Compound 22);

N-cyanomethyl-2-(2-dimethylaminothiazol-4-yl)-4-methylpentanamide (Compound 23);

N-cyanomethyl-4-methyl-2-[4-(4-pyrrolidin-1-ylphenyl) thiazol-2-yl]pentanamide (Compound 24);

N-cyanomethyl-4-methyl-2-(2-pyrid-4-ylthiazol-4-yl) pentanamide (Compound 25);

N-cyanomethyl-4-methyl-2-(4-pyrid-4-ylthiazol-2-yl) pentanamide (Compound 26);

N-cyanomethyl-4-methyl-2-(3-pyrid-3-ylphenyl) pentanamide (Compound 27);

N-cyanomethyl-4-methyl-2-[2-(4-morpholin-4-ylphenyl) thiazol-4-yl]pentanamide (Compound 28);

Example 9 tert-Butyl 3'-(1-cyanomethylcarbamoyl-3-methylbutyl)biphenyl-4-ylmethylcarbamate (Compound 29)

A mixture comprised of N-cyanomethyl-4-methyl-2-[3-(4,4,5,5-tetramethyl[1,3,2]dioxaborolan-2-yl)phenyl] pentanamide (250 mg, 0.702 mmol), tert-butyl 4-bromobenzylcarbamate (303 mg, 1.053 mmol), sodium bicarbonate (1.1 mL, 2.11 mmol), palladium(II) chloride (18 mg, 0.0211 mmol) and DMF (15.8 mL) was stirred under nitrogen at between 80–85° C. until the reaction was complete. The mixture was diluted with water and the product was extracted with diethyl ether (3×). The combined extracts were washed with brine, dried (MgSO$_4$) and then concentrated in vacuo. The product was purified from the residue by flash chromatography over silica gel (ethyl acetate/hexanes) to provide tert-butyl 3'-(1-cyanomethylcarbamoyl-3-methylbutyl)biphenyl-4-ylmethylcarbamate (252 mg, 0.576 mmol). $^1$H NMR (400 MHz, d$_6$-DMSO): δ 8.79 (br s, 1H), 7.58–7.26 (m, 9H), 4.16 (d, J=5.2 Hz, 2H), 4.11 (br s, 2H), 3.67 (dd, J=7.2, 7.2 Hz, 1H), 1.95–1.91 (m, 1H), 1.57–1.53 (m, 1H), 1.40–1.33 (m, 10H), 0.88 (dd, J=6.7, 6.7 Hz, 6H); MS (–ESI) m/z 434.6 (M–H)$^-$.

The following compounds of Formula I were provided by proceeding as in Example 9:

N-cyanomethyl-4-methyl-2-[3-(2-methylquinolin-6-yl) phenyl]pentanamide (Compound 30), $^1$H NMR (400 MHz, d$_6$-DMSO): δ 8.82 (t, J=5.1 Hz, 1H), 8.32 (d, J=8.3 Hz, 1H) 8.17 (s, 1H), 8.00 (s, 2H), 7.73 (s, 1H), 6.67 (d, J=7.6 Hz, 1H), 7.47–7.43 (m, 2H), 7.34 (d, J=7.5 Hz, 1H), 4.12 (d, J=5.2 Hz, 2H), 3.71 (dd, J=7.5, 7.5 Hz, 1H), 2.66 (s, 3H). 2.01–1.93 (m, 1H), 1.62–1.54 (m, 1H), 1.44–1.39 (m, 1H), 0.90 (dd, J=6.7, 6.7 Hz, 6H); MS (–ESI) m/z 370.4 (M–H)$^-$;

N-cyanomethyl-2-[3-(1H-indol-6-yl)phenyl]-4-methylpentanamide (Compound 31), $^1$H NMR (400 MHz, d$_6$-DMSO): δ 10.42 (s, 1H), 8.84 (t, J=5.3 Hz, 1H), 7.67 (s, 1H), 7.51 (d, J=7.4 Hz, 1H), 7.43–7.39 (m, 3H), 7.28 (d, J=7.6 Hz, 1H), 7.17 (t, J=7.6 Hz, 1H), 7.06 (d, J=7.1 Hz, 1H), 5.56 (s, 1H), 4.13 (br. s, 2H), 3.69 (dd, J=7.5, 7.5 Hz, 1H), 1.94–1.87 (m, 1H), 1.63–1.57 (m, 1H), 1.45–1.39 (m, 1H), 0.89 (dd, J=6.3, 6.3 Hz, 6H); MS (–ESI) m/z 344.2 (M–H)$^-$;

N-cyanomethyl-2-[3-(2,3-dihydro-1H-indol-5-yl) phenyl]-4-methylpentanamide (Compound 32), $^1$H NMR (400 MHz, d$_6$-DMSO): δ 8.76 (t, J=5.4 Hz, 1H), 7.46 (s, 1H), 7.37 (d, J=7.7 Hz, 1H), 7.34–7.26 (m, 3H), 7.18 (d, J=7.1 Hz, 1H), 7.13 (d, J=7.6 Hz, 1H), 6.55 (d, J=8.1 Hz, 1H), 4.11–4.09 (m, 2H), 3.61 (dd, J=7.6, 7.6 Hz, 1H), 4.47–4.42 (m, 2H), 2.98–2.93 (m, 2H), 1.94–1.87 (m, 1H), 1.56–1.49 (m, 1H), 1.43–1.35 (m, 1H), 0.87 (dd, J=6.6, 6.6 Hz, 6H); MS (−ESI) m/z 346.2 (M−H)$^-$;

2,2-dichloroethyl'-(1-cyanomethylcarbamoyl-3-methylbutyl)biphenyl-4-ylcarbamate (Compound 33), $^1$H NMR (400 MHz, d$_6$-DMSO): δ 10.08 (s, 1H), 8.78 (t, J=5.2 Hz, 1H), 7.64–7.50 (m, 5H), 7.48 (d, J=7.4 Hz, 1H), 7.36 (t, J=7.5 Hz, 1H), 7.25 (d, J=7.6 Hz, 1H), 6.52 (t, J=5.0 Hz, 1H), 4.55 (d, J=5.1 Hz, 2H), 4.11 (d, J=5.0 Hz, 2H), 3.65 (dd, J=7.4, 7.4 Hz, 1H), 1.96–1.88 (m, 1H), 1.58–1.50 (m, 1H), 1.45–1.34 (m, 1H), 0.88 (dd, J=7.0, 7.0 Hz, 6H); MS (−ESI) m/z 460.1 (M−H)$^-$;

N-cyanomethyl-4-methyl-2-(4'-phenoxybiphenyl-3-yl)pentanamide (Compound 34), $^1$H NMR (400 MHz, d$_6$-DMSO): δ 8.80 (br s, 1H), 7.63 (d, J=7.4 Hz, 2H), 7.56 (s, 1H), 7.49 (d, J=7.2 Hz, 1H), 7.43–7.36 (m, 3H), 7.28–7.25 (m, 1H), 7.18–7.04 (m, 5H), 4.11 (br. s, 2H), 3.66 (dd, J=7.2, 7.2 Hz, 1H), 1.96–1.89 (m, 1H), 1.58–1.51 (m, 1H), 1.41–1.36 (m, 1H), 0.88 (dd, J=6.5, 6.5 Hz, 6H); MS (−ESI) m/z 397.8 (M−H)$^-$;

N-cyanomethyl-4-methyl-2-[3-(1-oxoindan-5-yl)phenyl]pentanamide (Compound 35), $^1$H NMR (400 MHz, d$_6$-DMSO): δ 8.82 (t, J=5.1 Hz, 1H), 7.82 (s, 1H), 7.73–7.65 (m, 3H), 7.60 (d, J=7.5 Hz, 1H), 7.44 (t, J=7.6 Hz, 1H), 7.36 (d, J=7.6 Hz, 1H), 4.12 (d, J=4.5 Hz, 2H), 3.70 (dd, J=7.5, 7.5 Hz, 1H), 3.18–3.14 (m, 2H), 2.68–2.65 (m, 2H), 1.98–1.93 (m, 1H), 1.60–1.53 (m, 1H), 1.44–1.36 (m, 1H), 0.88 (dd, J=6.8, 6.8 Hz, 6H); MS (−ESI) m/z 359.2 (M−H)$^-$;

N-cyanomethyl-4-methyl-2-(3-pyrid-2-ylphenyl)pentanamide (Compound 36), $^1$H NMR (400 MHz, d$_6$-DMSO): δ 8.83 (br s, 1H), 8.66 (d, J=4.1 Hz, 1H), 8.06 (s, 1H), 7.91–7.85 (m, 3H), 7.44–7.33 (m, 3H), 4.11 (d, J=4.9 Hz, 2H), 3.70 (dd, J=7.4, 7.4 Hz, 1H), 1.98–1.90 (m, 1H), 1.58–1.51 (m, 1H), 1.43–1.37 (m, 1H), 0.88 (dd, J=6.5, 6.5 Hz, 6H); MS (−ESI) m/z 306.0 (M−H)$^-$;

N-cyanomethyl-2-(3-fur-3-ylphenyl)-4-methylpentanamide (Compound 37), $^1$H NMR (400 MHz, d$_6$-DMSO): δ 8.77 (br s, 1H), 8.13 (s, 1H), 7.74 (s, 1H), 7.48 (s, 1H), 7.46 (d, J=7.8 Hz, 1H), 7.31 (t, J=7.7 Hz, 1H), 7.19 (d, J=7.6 Hz, 1H), 6.90 (s, 1H), 4.10 (d, J=4.8 Hz, 2H), 3.61 (dd, J=7.5, 7.5 Hz, 1H), 1.95–1.87 (m, 1H), 1.56–1.48 (m, 1H), 1.42–1.35 (m, 1H), 0.87 (dd, J=6.9 Hz, 6H); MS (−ESI) m/z 295.3 (M−H)$^-$;

3'-(1-cyanomethylcarbamoyl)-3-methylbutyl]biphenyl-4-carboxamide (Compound 38), $^1$H NMR (400 MHz, d$_6$-DMSO): δ 8.80 (t, J=5.3 Hz, 1H), 8.03 (s, 1H), 7.97 (d, J=8.0 Hz, 2H), 7.71 (d, J=8.1 Hz, 2H), 7.63 (s, 1H), 7.58 (d, J=7.7 Hz, 1H), 7.44–7.39 (m, 2H), 7.33 (d, J=7.3 Hz, 1H), 4.11 (d, J=3.6 Hz, 2H), 3.68 (dd, J=7.5, 7.5 Hz, 1H), 1.98–1.90 (m, 1H), 1.59–1.52 (m, 1H), 1.44–1.37 (m, 1H), 0.88 (dd, J=6.9, 6.9 Hz, 6H); MS (−ESI) m/z 348.7 (M−H)$^-$;

N-cyanomethyl-4-methyl-2-(3-pyrimidin-5-ylphenyl)pentanamide (Compound 39), $^1$H NMR (400 MHz, d$_6$-DMSO): δ 9.19 (s, 1H), 9.10 (s, 2H), 8.80 (t, J=5.3 Hz, 1H), 7.69–7.65 (m, 2H), 7.48 (t, J=7.6 Hz, 1H), 7.41 (d, J=7.9 Hz, 1H), 4.11 (br s, 2H), 3.70 (dd, J=7.5, 7.5 Hz, 1H), 1.98–1.93 (m, 1H), 1.61–1.54 (m, 1H), 1.44–1.38 (m, 1H), 0.88 (dd, J=7.4, 7.4 Hz, 6H); MS (−ESI) m/z 306.9 (M−H)$^-$;

N-cyanomethyl-2-(4'-methylsulfonylbiphenyl-3-yl)-4-methylpentanamide (Compound 40), $^1$H NMR (400 MHz, d$_6$-DMSO): δ 8.82 (br s, 1H), 8.01 (d, J=8.4 Hz, 2H), 7.89 (d, J=8.4 Hz, 2H), 7.65 (s, 1H), 7.61 (d, J=7.6 Hz, 1H), 7.46 (t, J=7.6 Hz, 1H), 7.38 (d, J=7.4 Hz, 1H), 4.11 (br s, 2H), 3.70 (dd, J=7.5, 7.5 Hz, 1H), 3.25 (s, 3H), 1.98–1.90 (m, 1H), 1.60–1.52 (m, 1H), 1.42–1.38 (m, 1H), 0.88 (dd, J=7.1, 7.1 Hz, 6H); MS (−ESI) m/z 383.7 (M−H)$^-$;

N-cyanomethyl-2-[3-(3,5-dimethylisoxazol-4-yl)phenyl]-4-methylpentanamide (Compound 41), $^1$H NMR (400 MHz, d$_6$-DMSO): δ 8.81 (t, J=4.9 Hz, 1H), 7.40 (t, J=7.8 Hz, 1H), 7.31–7.23 (m, 3), 4.11 (d, J=5.4 Hz, 2H), 3.66 (dd, J=7.6, 7.6 Hz, 1H), 2.39 (s, 3H), 2.22 (s, 3H), 1.92–1.84 (m, 1H), 1.60–1.52 (m, 1H), 1.41–1.34 (m, 1H), 0.87 (dd, J=6.8, 6.8 Hz, 6H); MS (−ESI) m/z 324.2 (M−H)$^-$;

N-cyanomethyl-4-methyl-2-(3-pyrimidin-2-ylphenyl)pentanamide (Compound 42), $^1$H NMR (400 MHz, d$_6$-DMSO): δ 8.91–8.85 (m, 3H), 8.40 (s, 1H), 8.26 (d, J=5.6 Hz, 1H), 7.47–7.42 (m, 3H), 4.12 (d, J=4.1 Hz, 2H), 3.72 (dd, J=7.5, 7.5 Hz, 1H), 1.98–1.90 (m, 1H), 1.58–1.90 (m, 1H), 1.42–1.35 (m, 1H), 0.88 (dd, J=6.4, 6.4 Hz, 6H); MS (−ESI) m/z 307.3 (M−H)$^-$;

tert-butyl N-5-[3-(1-cyanomethylcarbamoyl-3-methylbutyl)phenyl]pyrimidin-2-yl-N-(tert-butoxycarbonyl)carbamate (Compound 43), $^1$H NMR (400 MHz, d$_6$-DMSO): δ 9.07 (s, 2H), 7.99 (br s, 1H), 7.81 (s, 1H), 7.71–7.68 (m, 1H), 7.52–7.50 (m, 2H), 4.21–4.17 (m, 2H), 3.82 (dd, J=7.2, 7.2 Hz, 1H), 1.74–1.66 (m, 1H), 1.55–1.42 (m, 20H), 0.92 (dd, J=4.3, 4.3 Hz, 6H); MS (−ESI) m/z 522.7 (M−H)$^-$;

N-cyanomethyl-2-[3-(4,5-dichloro-1H-imidazol-2-yl)phenyl]-4-methylpentanamide (Compound 44);

tert-butyl 3'-(1-cyanomethylcarbamoyl-3-methylbutyl)biphenyl-4-ylcarbamate (Compound 45), $^1$H NMR (400 MHz, d$_6$-DMSO): δ 8.80 (t, J=5.1 Hz, 1H), 7.69 (d, J=8.0 Hz, 2H), 7.60 (s, 1H), 7.55 (d, J=7.6 Hz, 1H), 7.44–7.37 (m, 3H), 7.31 (d, J=7.8 Hz, 1H), 4.12 (d, J=3.6 Hz, 2H), 3.69 (dd, J=7.4, 7.4 Hz, 1H), 1.96–1.90 (m, 1H), 1.59–1.52 (m, 1H), 1.43–1.37 (m, 10H), 0.88 (dd, J=6.8, 6.8 Hz, 6H); MS (−ESI) m/z 420.1 (M−H)$^-$;

N-cyanomethyl-4-methyl-2-(3-quinolin-3-ylphenyl)pentanamide (Compound 46);

N-cyanomethyl-2-[3-(1H-indol-5-yl)phenyl]-4-methylpentanamide (Compound 47);

N-cyanomethyl-2-(4'-acetylaminobiphenyl-3-yl)-4-methylpentanamide (Compound 48);

The following compounds of Formula I were provided by proceeding as in the methods described in this Application:

N-cyanomethyl-2-(4'-methoxybiphenyl-3-yl)-4-methylpentanamide (Compound 49);

N-cyanomethyl-2-(2',4'-dimethoxybiphenyl-3-yl)-4-methylpentanamide (Compound 50);

N-cyanomethyl-2-(3'-methoxybiphenyl-3-yl)-4-methylpentanamide (Compound 51);

N-cyanomethyl-4-methyl-2-(4'-morpholin-4-ylsulfonylbiphenyl-3-yl)pentanamide (Compound 52);

N-cyanomethyl-4-methyl-2-(3'-morpholin-4-ylsulfonylbiphenyl-3-yl)pentanamide (Compound 53);

methyl 3'-(1-cyanomethylcarbamoyl-3-methylbutyl)biphenyl-2-carboxylate (Compound 54);

N-cyanomethyl-2-[3-(2,3-dihydrobenzo[1,4]dioxin-6-yl)phenyl]-4-methylpentanamide (Compound 55);

N-cyanomethyl-4-methyl-2-[3-(4,4,5,5-tetramethyl-[1,3,2]dioxaborolan-2-yl)phenyl]pentanamide (Compound 56);

N-cyanomethyl-2-[4'-(1-hydroxyethyl)biphenyl-3-yl]-4-methylpentanamide (Compound 57);

N-cyanomethyl-2-(3',5'-bistrifluoromethylbiphenyl-3-yl)-4-methylpentanamide (Compound 58);

2-(4'-cyano-2'-methylbiphenyl-3-yl)-N-cyanomethyl-4-methylpentanamide (Compound 59);

N-cyanomethyl-4-methyl-2-(4'-sulfamoylbiphenyl-3-yl)pentanamide (Compound 60);

N-cyanomethyl-2-(3-isoquinolin-4-ylphenyl)-4-methylpentanamide (Compound 61);

N-cyanomethyl-2-(3'-fluorobiphenyl-3-yl)-4-methylpentanamide (Compound 62);

2-[3-(6-bromopyrid-2-yl)phenyl]-N-cyanomethyl-4-methylpentanamide (Compound 63);

N-cyanomethyl-2-(2',6'-diethylbiphenyl-3-yl)-4-methylpentanamide (Compound 65);

N-cyanomethyl-2-(2'-methoxy-5'-nitrobiphenyl-3-yl)-4-methylpentanamide (Compound 66);

2-biphenyl-3-yl-N-(1-cyano-3-methylsulfanylpropyl)-4-methylpentanamide (Compound 67);

N-cyanomethyl-4-methyl-2-(3'-nitrobiphenyl-3-yl)pentanamide (Compound 69);

N-cyanomethyl-4-methyl-2-(4'-nitrobiphenyl-3-yl)pentanamide (Compound 70);

2-(2'-cyanobiphenyl-3-yl)-N-cyanomethyl-4-methylpentanamide (Compound 71);

2-(3'-cyanobiphenyl-3-yl)-N-cyanomethyl-4-methylpentanamide (Compound 72);

2-(4'-cyanobiphenyl-3-yl)-N-cyanomethyl-4-methylpentanamide (Compound 73);

N-cyanomethyl-4-methyl-2-(3-quinolin-8-ylphenyl)pentanamide (Compound 74);

N-cyanomethyl-4-methyl-2-(3-quinolin-3-ylphenyl)pentanamide (Compound 75);

N-cyanomethyl-4-methyl-2-(4'-trifluoromethoxybiphenyl-3-yl)pentanamide (Compound 76);

2-(3'-aminobiphenyl-3-yl)-N-cyanomethyl-4-methylpentanamide (Compound 77);

2-(4'-aminobiphenyl-3-yl)-N-cyanomethyl-4-methylpentanamide (Compound 78);

N-cyanomethyl-2-(4'-dimethylaminobiphenyl-3-yl)-4-methylpentanamide (Compound 79);

N-cyanomethyl-4-methyl-2-(3-pyrid-4-ylphenyl)pentanamide (Compound 80);

N-cyanomethyl-4-2-(3-thiazol-2-ylphenyl)pentanaminde (Compound 81);

N-cyanomethyl-2-[3-(1H-indol-5-yl)phenyl]-4-methylpentanamide (Compound 82);

N-cyanomethyl-2-[3'-(2-dimethylaminothiazol-4-yl)biphenyl-3-yl]-4-methylpentanamide (Compound 83);

N-cyanomethyl-2-(4'-hydroxy-3'-isoxazol-5-ylbiphenyl-3-yl)-4-methylpentanamide (Compound 84);

N-cyanomethyl-4-methyl-2-(3-thien-2-ylphenyl)pentanamide (Compound 86);

2-biphenyl-3-yl-N-(1S-cyanoethyl)-4-methylpentanamide (Compound 87);

N-cyanomethyl-4-methyl-2-(4'-methylsulfamoylbiphenyl-3-yl)pentanamide (Compound 88);

N-cyanomethyl-4-methyl-2-(3'-methylsulfamoylbiphenyl-3-yl)pentanamide (Compound 89);

N-cyanomethyl-4-methyl-2-[3-(5-nitrothiazol-2-yl)phenyl]pentanamide (Compound 90);

N-cyanomethyl-2-(4'-acetylaminobiphenyl-3-yl)-4-methylpentanamide (Compound 91);

benzyl[5-(2-biphenyl-3-yl-4-methylpentanoylamino)-5-cyanopentyl]carbamate (Compound 92);

N-cyanomethyl-2-(5'-acetyl-2'-morpholin-4-ylbiphenyl-3-yl)-4-methylpentanamide (Compound 93);

N-(1S-cyanopentyl)-2-biphenyl-3-yl-4-methylpentanamide (Compound 94);

N-cyanomethyl-2-[3'-(2-guanidinothiazol-4-yl)biphenyl-4-yl]-4-methylpentanamide (Compound 95);

3-(1-cyanomethylcarbamoyl-3-methylbutyl)phenyl 2-(3-hydroxyphenyl)-4-methylpentanoate (Compound 96), $^1$H NMR (400 MHz, d$_6$-DMSO): δ 9.46 (s, 1H), 8.80 (br s, 1H), 7.32 (t, J=7.8 Hz, 1H), 7.19–7.14 (m, 2H), 6.92 (s, 1H), 6.85 (d, J=7.9 Hz, 1H), 6.82–6.79 (m, 2H), 6.69 (d, J=7.9 Hz, 1H), 4.09 (br s, 2H), 3.85 (dd, J=7.6, 7.6 Hz, 1H), 3.59 (dd, J=7.4, 7.4 Hz, 1H), 1.95–1.87 (m, 2H), 1.83–1.63 (m, 1H), 1.49–1.29 (m, 3H), 0.99 (d, J=6.1 Hz, 6H), 0.84 (dd, J=7.4, 7.4 Hz, 6H);

N-cyanomethyl-2-(3-methoxyphenyl)-4-methylpentanamide (Compound 97), $^1$H NMR (400 MHz, d$_6$-DMSO): δ 8.74 (t, J=5.1 Hz, 1H), 7.20 (t, J=7.9 Hz, 1H), 6.87–6.85 (m, 2H), 6.79 (d, J=8.0 Hz, 1H), 4.09 (d, J=5.3 Hz, 2H), 3.72 (s, 3H), 3.55 (dd, J=7.5, 7.5 Hz, 1H), 1.89–1.81 (m, 1H), 1.51–1.44 (m, 1H), 1.39–1.32 (m, 1H), 0.85 (dd, J=6.7, 6.7 Hz, 6H); MS (–ESI) m/z 259.0 (M–H)$^-$;

2-(4'-aminomethylbiphenyl-3-yl)-N-(cyanomethyl)-4-methylpentanamide (Compound 98), $^1$H NMR (400 MHz, d$_6$-acetone): δ 8.01 (br s, 1H), 7.65 (s, 1H), 7.57 (d, J=8.0 Hz, 2H), 7.51 (d, J=7.5 Hz, 1H), 7.43 (d, J=8.0 Hz, 2H), 7.38 (t, J=7.6 Hz, 1H), 7.33 (d, J=7.9 Hz, 1H), 4.46 (s, 2H), 4.17 (dd, J=27.6, 17.5 Hz, 2H), 3.76 (dd, J=8.7, 8.7 Hz, 1H), 2.10–1.94 (m, 1H), 1.70–1.63 (m., 1H), 1.53–1.46 (m, 1H), 0.91 (dd, J=6.35, 3.5 Hz, 6H); MS (–ESI) m/z 334.4 (M–H)$^-$;

N-cyanomethyl-4-methyl-2-[3-(1-methyl-1H-indol-5-yl)phenyl]pentanamide (Compound 99), $^1$H NMR (400 MHz, d$_6$-DMSO): δ 8.81 (t, J=5.4 Hz, 1H), 7.79 (s, 1H), 7.62 (s, 1H), 7.53–7.49 (m, 2H), 7.43 (d, J=8.5 Hz, 1H), 7.39–7.34 (m, 2H), 7.23 (d, J=7.5 Hz, 1H), 6.49 (d, J=2.8 Hz, 1H), 4.13 (dd, J=5.3, 2.2 Hz, 2H), 3.80 (s, 3H), 3.68 (dd, J=7.6, 7.6 Hz, 1H), 1.98–1.91 (m, 1H), 1.61–1.53 (m, 1H), 1.46–1.39 (m, 1H), 0.89 (dd, J=6.6, 6.6 Hz, 6H); MS (–ESI) m/z 359.2 (M–H)$^-$;

N-cyanomethyl-4-methyl-2-(4'-morpholin-4-ylbiphenyl-3-yl)pentanamide (Compound 100), $^1$H NMR (400 MHz, d$_6$-DMSO): δ 8.78 (t, J=5.5 Hz, 1H), 7.52–7.49 (m, 3H), 7.45 (d, J=7.9 Hz, 1H), 7.33 (t, J=7.7 Hz, 1H), 7.20 (d, J=7.7 Hz, 1H), 7.02 (d, J=8.8 Hz, 2H) 4.10 (dd, J=5.5, 1.8 Hz, 2H), 3.76–3.74 (m, 4H), 3.64 (dd, J=8.6, 6.6 Hz, 1H), 3.16–3.12 (m, 4H), 1.95–1.87 (m, 1H), 1.57–1.50 (m, 1H), 1.45–1.36 (m, 1H), 0.88 (dd, J=6.8, 6.8 Hz, 6H); MS (–ESI) m/z 390.3 (M–H)$^-$;

N-cyanomethyl-2-[3-(7-nitro-1H-indol-5-yl)phenyl]-4-methylpentanamide (Compound 101), $^1$H NMR (400 MHz, d$_6$-DMSO): δ 11.99 (s, 1H), 8.84 (t, J=5.5 Hz, 1H), 8.35 (s, 1H), 8.30 (d, J=1.3 Hz, 1H), 7.70 (s, 1H), 7.63 (d, J=7.8 Hz, 1H), 7.57 (t, J=2.7 Hz, 1H), 7.43 (d, J=7.7 Hz, 1H), 7.32 (d, J=7.7 Hz, 1H), 6.80 (dd, J=3.0, 1.8 Hz, 1H), 4.13 (dd, J=5.4, 3.4 Hz, 2H), 3.72 (dd, J=8.6, 6.6 Hz, 1H), 2.00–1.93 (m, 1H), 1.61–1.53 (m, 1H), 1.46–1.38 (m, 1H), 0.89 (dd, J=6.9, 6.9 Hz, 6H); MS (–ESI) m/z 389.0 (M–H)$^-$;

N-cyanomethyl-4-methyl-2-[3-(7-nitro-2,3-dihydro-1H-indol-5-yl)phenyl]pentanamide (Compound 102), $^1$H NMR (400 MHz, d$_6$-DMSO): δ 8.80 (t, J=5.4 Hz, 1H), 8.07 (s, 1H), 7.86 (s, 1H), 7.60 (s, 1H), 7.54 (s, 1H), 7.46 (d, J=7.7 Hz, 1H), 7.35 (t, J=7.6 Hz, 1H). 7.24 (d, J=7.6 Hz, 1H), 4.11 (dd, J=5.3, 2.9, Hz, 2H), 3.79 (t, J=8.4 Hz, 2H), 3.66 (dd, J=8.2, 6.9 Hz, 1H), 3.16 (t, J=8.3 Hz, 2H), 1.97–1.89 (m, 1H), 1.57–1.49 (m, 1H), 1.43–1.35 (m, 1H), 0.88 (dd, J=6.8, 6.8 Hz, 6H); MS (–ESI) m/z 391.3 (M–H)$^-$;

5-[3-(1-cyanomethylaminocarbonyl-3-methylbutyl) phenyl]-1H-indole-2-carboxylic acid (Compound 103), $^1$H NMR (400 MHz, d$_6$-DMSO): δ 11.79 (s, 1H), 8.80 (t, J=5.6, Hz, 1H), 7.86 (s, 1H), 7.59 (s, 1H), 7.53–7.49 (m, 3H), 7.36 (t, J=7.7 Hz, 1H), 7.25–7.11 (m, 3H), 4.11 (d, J=5.5 Hz, 2H), 3.67 (dd, J=7.5, 7.5 Hz, 1H), 1.99–1.88 (m, 1H), 1.60–1.50 (m, 1H), 1.45–1.35 (m, 1H), 0.88 (dd, J=5.9, 5.9 Hz, 6H); MS (−ESI) m/z 388.3 (M−H)$^−$;

N-cyanomethyl-4-methyl-2-(3'-morpholin-4-ylbiphenyl-3-yl)pentanamide (Compound 104), $^1$H NMR (400 MHz, d$_6$-DMSO): δ 8.78 (t, J=5.3 Hz, 1H), 7.53–7.48 (m, 2H), 7.37 (t, J=7.6, 1H), 7.33–7.26 (m, 2H), 7.10 (s, 1H), 7.03 (d, J=7.7 Hz, 1H), 6.95 (d, J=8.2 Hz, 1H), 4.11 (d, J=5.5 Hz, 2H), 3.77–3.73 (m, 4H), 3.66 (dd, J=7.3, 7.3 Hz, 1H), 3.18–3.16 (m, 4H), 1.98–1.89 (m 1H), 1.57–1.50 (m, 1H), 1.43–1.36 (m, 1H), 0.90–0.84 (m, 6H); MS (−ESI) m/z 390.4 (M−H)$^−$;

N-cyanomethyl-4-methyl-2-(2'-morpholinylbiphenyl-3-yl)pentanamide (Compound 105), $^1$H NMR (400 MHz, d$_6$-DMSO): δ 8.81 (t, J=5.6 Hz, 1H), 7.64 (s, 1H), 7.40–7.33 (m, 2H), 7.29 (t, J=7.7 Hz, 1H), 7.24 (d, J=6.9 Hz, 1H), 7.16 (d, J=7.4 Hz, 1H), 7.07 (t, J=8.2 Hz, 2H), 4.09 (d, J=5.5 Hz, 2H), 3.63 (dd, J=7.4, 7.4 Hz, 1H), 3.47 (s, 4H), 2.69 (s, 4H), 1.98–1.89 (m, 1H), 1.57–1.50 (m, 1H), 1.44–1.36 (m, 1H), 0.88 (dd, J=6.3, 6.3 Hz, 6H); MS (−ESI) m/z 390.4 (M−H)$^−$;

2-[3-(7-amino-1H-indol-5-yl)phenyl]-N-cyanomethyl-4-methylpentanamide (Compound 106); $^1$H NMR (400 MHz, d$_6$-DMSO): δ 10.69 (s, 1H), 8.80 (s, 1H), 7.53 (s, 1H), 7.42 (d, J=7.1 Hz, 1H), 7.34–7.27 (m, 2H), 7.17 (d, J=7.1 Hz, 1H), 7.03 (s, 1H), 6.60 (s, 1H), 6.36 (s, 1H), 5.16 (s, 2H), 4.11 (br s, 2H), 3.64 (dd, J=7.3, 7.3 Hz, 1H), 1.97–1.89 (m, 1H), 1.57–1.51 (m, 1H), 1.43–1.39 (m, 1H), 0.89 (dd, J=6.3, 6.3 Hz, 6H); MS (−ESI) m/z 358.8 (M−H)$^−$;

5-[3-(1-cyanomethyl)aminocarbonyl-3-methylbutyl) phenyl]-1H-indole-2-carboxamide (Compound 107), $^1$H NMR (400 MHz, d$_6$-acetone): δ 10.90 (s, 1H), 7.97 (br s, 1H), 7.88 (d, J=0.7 Hz, 1H), 7.81–7.49 (m, 5H), 7.38 (t, J=7.6 Hz, 1H), 7.35–7.29 (m, 1H), 7.23 (d, J=1.2 Hz, 1H), 6.80 (br s, 1H), 4.22–4.17 (m, 2H), 3.80–3.72 (m, 1H), 2.1–1.98 (m, 1H), 1.76–1.64 (m, 1H), 1.57–1.47 (m, 1H), 0.94–0.87 (n, 6H); MS (−ESI) m/z 387.4 (M−H)$^−$;

N-cyanomethyl-4-methyl-2-(4'-piperazin-1-ylbiphenyl-3-yl)pentanamide (Compound 108), $^1$H NMR (400 MHz, d$_6$-DMSO): δ 8.80 (t, J=5.5 Hz, 1H), 7.52–7.46 (m, 3H), 7.43 (d, J=7.8 Hz, 1H), 7.33 (t, J=7.7 Hz, 1H), 7.19 (d, J=7.6 Hz, 1H), 6.99 (d, J=8.8 Hz, 2H), 4.11 (dd, J=5.5, 2.2 Hz, 2H), 3.64 (dd, J=8.6, 6.7 Hz, 1H), 3.10–3.06 (m, 4H), 2.85–2.82 (m, 4H), 1.96–1.88 (m, 1H), 1.58–1.50 (m, 1H), 1.42–1.36 (m, 1H), 0.88 (dd, J=6.8, 6.8 Hz, 6H); MS (+ESI) m/z 391.2 (M+H)$^+$;

N-cyanomethyl-4-methyl-2-[4'-(4-methylpiperazin-1-yl) biphenyl-3-yl]pentanamide (Compound 109), $^1$H NMR (400 MHz, d$_6$-DMSO): δ 8.78 (t, J=5.6 Hz, 1H), 7.51–7.46 (m, 3H), 7.44 (d, J=7.9 Hz, 1H), 7.33 (t, J=7.7 Hz, 1H), 7.19 (d, J=7.6 Hz, 1H), 7.01 (d, J=8.8 Hz, 2H), 4.10 (dd, J=5.5, 2.1 Hz, 2H), 3.64 (dd, J=8.6, 6.7 Hz, 1H), 3.19–3.15 (m, 4H), 2.47–2.44 (m, 4H), 2.22 (m, 3H), 1.94–1.87 (m, 1H), 1.57–1.50 (m, 1H), 1.41–1.37 (m, 1H), 0.88 (dd, J=6.8, 6.8 Hz, 6H); MS (+ESI) m/z 405.1 (M+H)$^+$;

N-cyanomethyl-2-{3-[3-(dimethylaminomethyl)-1H-indol-5-yl]phenyl}-4-methylpentanamide (Compound 110), $^1$H NMR (400 MHz, d$_6$-acetone): δ 10.18 (s, 1H), 7.94 (br s, 2H), 7.66 (s, 1H), 7.53 (d, J=7.8 Hz, 1H), 7.46 (d, J=8.4 Hz, 1H), 7.40–7.34 (m, 2H), 7.30–7.26 (m, 2H), 4.19 (dd, J=11.5, 5.8 Hz, 2H), 3.76 (dd, J=7.7, 7.7 Hz, 1H), 3.63 (s, 2H), 2.21 (s, 6H), 2.08–1.97 (m, 1H), 1.73–1.65 (m, 1H), 1.55–1.48 (m, 1H), 0.96–0.91 (m, 6H); MS (+ESI) m/z 404.4 (M+H)$^+$;

N-cyanomethyl-4-methyl-2-[3-(2-oxo-2,3-dihydro-1H-pyrrolo[2,3-b]pyrid-5-yl)phenyl]pentanamide (Compound 111), $^1$H NMR (400 MHz, d$_6$-acetone): δ 9.94 (s, 1H), 8.32 (d, J=2.1 Hz, 1H), 7.96 (br s, 1H), 7.83 (s, 1H), 7.63 (s, 1H), 7.52 (d, J=1.5 Hz, 1H), 7.50–7.34 (m, 2H), 4.19 (dd, J=6.1, 6.1 Hz, 2H), 3.77 (dd, J=7.7, 7.7 Hz, 1H), 3.60 (s, 2H), 2.07–1.99 (m, 1H), 1.71–1.63 (m, 1H), 1.53–1.47 (m, 1H), 0.91 (dd, J=6.6, 3.4 Hz, 6H); MS (−ESI) m/z 361.4 (M−H)$^−$; and N-cyanomethyl-4-methyl-2-[3-(1H-pyrrolo[2,3-b]pyridi-5-yl)phenyl]pentanamide (Compound 112), $^1$H NMR (400 MHz, d$_6$-DMSO): δ 11.72 (s, 1H), 8.80 (br s, 1H), 8.48 (s, 1H), 8.17 (s, 1H), 7.63 (s, 1H), 7.56 (d, J=7.5 Hz, 1H), 7.51 (s, 1H), 7.40 (t, J=7.6 Hz, 1H), 7.28 (d, J=7.4 Hz, 1H), 6.51 (s, 1H), 4.12 (dd, J=2.4, 2.4 Hz, 2H), 3.69 (dd, J=7.5, 7.5 Hz, 1H), 1.98–1.91 (m, 1H), 1.62–1.54 (m, 1H), 1.46–1.38 (m, 1H), 0.89 (dd, J=6.8, 6.8 Hz, 6H); MS (−ESI) m/z 345.4 (M−H)$^−$;

N-cyanomethyl-4-methyl-2-(3-quinolin-3-ylphenyl) pentanamide (Compound 113);

N-cyanomethyl-2-[3-(1H-indol-5-yl)phenyl]-4-methylpentanamide (Compound 114);

N-cyanomethyl-2-(4'-acetylaminobiphenyl-3-yl)-4-methylpentanamide (Compound 115);

N-cyanomethyl-2-(4'-aminomethylbiphenyl-3-yl)-4-methylpentanamide (Compound 116);

N-cyanomethyl-4-methyl-2-[3-(1-methyl-1H-indol-5-yl)phenyl]pentanamide (Compound 117);

N-cyanomethyl-4-methyl-2-(4'-morpholin-4-ylbiphenyl-3-yl)pentanamide (Compound 118);

N-cyanomethyl-4-methyl-2-[3-(7-nitro-1H-indol-5-yl)phenyl]pentanamide (Compound 119);

N-cyanomethyl-4-methyl-2-[3-(7-nitro-2,3-dihydro-1H-indol-5-yl)phenyl]pentanamide (Compound 120);

5-{3-[1-(cyanomethylcarbamoyl)-3-methylbutyl] phenyl}-1H-indole-2-carboxylic acid (Compound 121);

N-cyanomethyl-4-methyl-2-(3'-morpholin-4-ylbiphenyl-3-yl)pentanamide (Compound 122);

N-cyanomethyl-4-methyl-2-(2'-morpholin-4-ylbiphenyl-3-yl)pentanamide (Compound 123);

N-cyanomethyl-2-[3-(7-amino-1H-indol-5-yl)phenyl]-4-methylpentanamide (Compound 124);

5-{3-[1-(cyanomethylcarbamoyl)-3-methylbutyl] phenyl}-1H-indole-2-carboxamide (Compound 125);

N-cyanomethyl-4-methyl-2-(4'-piperazin-1-ylbiphenyl-3-yl)pentanamide (Compound 126);

N-cyanomethyl-4-methyl-2-[4'-(4-methylpiperazin-1-yl) biphenyl-3-yl]pentanamide (Compound 127);

N-cyanomethyl-2-[3-(3-dimethylaminomethyl-1H-indol-5-yl)phenyl]-4-methylpentanamide (Compound 128);

N-cyanomethyl-4-methyl-2-[3-(2-oxo-2,3-dihydro-1H-indol-5-yl)phenyl]pentanamide (Compound 129);

N-cyanomethyl-2-[3-(1H-indol-5-yl)phenyl]-4-methylpentanamide (Compound 130);

N-cyanomethyl-4-methyl-2-[3-(1H-pyrrolo[2,3-b]pyrid-5-yl)phenyl]pentanamide (Compound 131);

N-cyanomethyl-4-methyl-2-[3-(2-oxo-2,3-dihydro-1H-pyrrolo[2,3-b]pyrid-5-yl)phenyl]pentanamide (Compound 132);

N-cyanomethyl-4-methyl-2-[3-(2-oxo-2,3-dihydro-1,3-benzothiazol-6-yl)phenyl]pentanamide (Compound 133);

ethyl 4-[3'-(1-{[(cyanomethyl)amino]carbonyl}-3-methylbutyl)[1,1'-biphenyl]-4-yl]-1-piperazinecarboxylate (Compound 134); and 2-{3-[3-(2-aminoethyl)-1H-indol-5-yl]phenyl}-N-(cyanomethyl)-4-methylpentanamide (Compound 135).

4-Methyl-2-[3'-(2-piperazin-1-yl-thiazol-4-yl)-biphenyl-3-yl]-pentanoic acid cyanomethyl-amide (Compound 156) $^1$H NMR (dmso-d$_6$): δ 0.92 (d, 6H), 1.21–1.51 (m, 2H), 1.98 (m, 1H), 2.81 (m, 5H), 3.80 (m, 6H), 4.21 (m, 2H), 7.10–7.60 (m, 7H), 7.61 (d, 1H), 8.01 (s, 1H), 8.81–9.10 (m, 2H). LCMS: 474.2 (M+H$^+$).

2-(4'-Hydroxy-3'-isoxazol-5-yl-biphenyl-3-yl)-4-methyl-pentanoic acid cyanomethyl-amide (Compound 157) $^1$H NMR (dmso-d$_6$): δ 0.89 (d, 6H), 1.21–1.88 (m, 3H), 3.88 (m, 1H), 4.12 (m, 2H), 6.71–7.64 (m, 6H), 7.81–8.24 (m, 3H), 8.81 (s, 1H), 9.01 (m, 1H). LCMS: 390.3 (M+H$^+$).

2-[4'-(2-Dimethylamino-thiazol-4-yl)-biphenyl-3-yl]-4-methyl-pentanoic acid cyanomethyl-amide (Compound 158) $^1$H NMR (dmso-d$_6$): δ 0.93 (d, 6H), 1.31–1.78 (m, 3H), 2.89–3.18 (m, 6H), 4.32 (m, 3H), 6.58–6.84 (m, 12H), 7.21 (s, 1H), 7.81 (m, 1H). 7.93 (m, 2H). LCMS: 433.1 (M+H$^+$).

2-[3'-(2-Guanidino-thiazol-4-yl)-biphenyl-3-yl]-4-methyl-pentanoic acid cyanomethyl-amide (Compound 159) $^1$H NMR (dmso-d$_6$): δ 0.93 (d, 6H), 1.41–1.88 (m, 3H), 3.88 (m, 1H), 4.12 (m, 2H), 7.18–7.24 (m, 6H), 7.21 (s, 1H), 7.41–7.81 (m, 5H), 8.71 (m, 1H). LCMS: 447.0 (M+H$^+$).

4-Methyl-2-{3-[5-(4-methyl-piperazine-1-sulfonyl)-thiophen-2-yl]-phenyl}-pentanoic acid cyanomethyl-amide (Compound 160) $^1$H NMR (dmso-d$_6$): δ 0.93 (d, 6H), 1.41–1.88 (m, 3H), 2.55 (m, 2H). 2.89 (s, 3H), 3.12–3.88 (m, 7H), 4.12 (m, 2H), 7.18–7.24 (m, 2H), 7.41–7.81 (m, 4H), 8.81 (s, 1H). LCMS: 475.1 (M+H$^+$).

4-Methyl-2-{3-[2-(4-methyl-piperazin-1-yl)-thiazol-4-yl]-phenyl}-pentanoic acid cyanomethyl-amide (Compound 161) $^1$H NMR (dmso-d$_6$): δ 0.93 (d, 6H), 1.41–1.88 (m, 3H), 2.81 (s, 3H), 3.12–3.80 (m, 7H), 4.12 (m, 3H), 7.10–7.24 (m, 3H), 7.61–7.81 (m, 2H), 8.81 (s, 1H). LCMS: 412.1 (M+H$^+$).

N-{3-[5-(3,5-Dichloro-2-hydroxy-phenyl)-1H-pyrazol-3-yl]-propyl}-guanidine (Compound 162) $^1$H NMR (dmso-d$_6$): δ 0.96 (d, 6H), 1.38–1.81 (m, 3H), 2.81 (m, 2H), 3.16 (m, 2H), 3.28 3.44 (m, 4H), 3.60–3.88 (m, 10H), 4.12 (m, 3H), 7.10–7.24 (m, 2H), 7.61–7.81 (m, 2H), 8.81 (s, 1H). LCMS: 505.3 (M+H$^+$).

2-{3-[2-(3,5-Dimethyl-piperazin-1-yl)-thiazol-4-yl]-phenyl}-4-methyl-pentanoic acid cyanomethyl-amide (Compound 163) $^1$H NMR (dmso-d$_6$): δ 0.93 (d, 6H), 1.11 (d, 6H), 1.21–1.88 (m, 3H), 3.01 (s, 2H), 3.62–3.80 (m, 8H), 4.12 (m, 4H), 7.14–7.24 (m, 3H), 7.81 (m, 2H), 8.71 (s, 1H). LCMS: 426.0 (M+H$^+$).

4-Methyl-2-{3-[2-(4-methyl-piperazin-1-yl)-thiazol-5-yl]-phenyl}-pentanoic acid cyanomethyl-amide (Compound 164) $^1$H NMR (dmso-d$_6$): δ0.89 (d, 6H), 1.21–1.41 (m, 2H), 1.88 (m, 1H), 2.81 (s, 3H), 3.12–3.80 (m, 7H), 4.12 (m, 4H), 6.91–7.24 (m, 4H), 7.61 (s, 1H), 8.61 (s, 1H). LCMS: 411.8 (M+H$^+$).

4-Methyl-2-[2-(4-piperazin-1-yl-phenyl)-thiazol-4-yl]-pentanoic acid cyanomethyl-amide (Compound 165) $^1$H NMR (dmso-d$_6$): δ 0.89 (d, 6H), 1.21–1.68 (m, 3H), 3.12–3.48 (m, 8H), 3.61 (m, 1H), 4.12 (m, 4H), 6.91 (m, 2H), 7.21 (s, 1H), 7.61 (d, 2H), 8.61 (s, 1H). LCMS: 397.8 (M+H$^+$).

4-Methyl-2-{3'-[2-(4-methyl-piperazin-1-yl)-thiazol-4-yl]-biphenyl-3-yl}-pentanoic acid cyanomethyl-amide (Compound 166) $^1$H NMR (dmso-d$_6$): δ 0.92 (d, 6H), 1.21–1.51 (m, 2H), 1.88 (m, 1H), 2.81 (s, 3H), 3.12–3.80 (m, 7H), 4.16 (m, 4H), 7.15–7.56 (m, 6H), 7.61 (d, 1H), 8.01 (s, 1H), 8.61 (s, 1H). LCMS: 487.8 (M+H$^+$).

4-Methyl-2-{4'-[2-(4-methyl-piperazin-1-yl)-thiazol-4-yl]-biphenyl-3-yl}-pentanoic acid cyanomethyl-amide (Compound 167): $^1$H NMR (dmso-d$_6$): δ0.98 (d, 6H), 1.26–1.61 (m, 2H), 1.88 (m, 1H), 2.88 (s, 3H), 3.12–3.80 (m, 7H), 4.20 (m, 4H), 7.15–7.56 (m, 7H), 7.81 (d, 2H), 8.81 (s, 1H). LCMS: 488.4 (M+H$^+$).

4-Methyl-2-[3'-(pyrrolidin-3-yloxy)-biphenyl-3-yl]-pentanoic acid cyanomethyl-amide (Compound 168) $^1$HNMR (dmso-d$_6$): δ 8.98 (1H, bs), 8.83 (1H, t, J: 6.3 Hz), 7.57 (1H, s), 7.53 (1H, d), 7.42 (2H, m), 7.29 (1H, m), 7.16 (1H, m), 7.00 (2H, dd, J: 8.52, 2.2 Hz), 5.25 (1H, bs), 4.11 (2H, d), 3.68 (1H, dd), 3.46 (2H, m), 3.36 (2H, m), 2.23 (2H, m), 1.90 (1H, m), 1.55 (1H, m), 1.40 (1H, m), 0.89 (6H, m). LC/MS: M+1: 392.

2-{3'-[1-(2-Hydroxy-ethyl)-piperidin-4-yloxy]-biphenyl-3-yl}-4-methyl-pentanoic acid cyanomethyl-amide (Compound 169) 1HNMR (dmso-d$_6$): δ 8.79 (1H, t), 7.56 (1H, s), 7.50 (1H, d), 7.35 (3H, m), 7.15 (2H, m), 6.98 (1H, dd), 4.48 (1H, bs), 4.11 (2H, d), 3.67 (1H, dd), 3.51 (2H, m), 2.78 (2H, m), 2.40 (2H, m), 2.30 (3H, s), 1.96 (2H, m), 1.80 (1H, m), 1.57 (1H, m), 1.40 (1H, m), 0.89 (6H, m). LC/MS: 449.4.

4-Methyl-2-[3'-(piperidin-4-yloxy)-biphenyl-3-yl]-pentanoic acid cyanomethyl-amide (Compound 170) $^1$HNMR (dmso-d$_6$): δ 8.82 (1H, t), 8.46 (2H, bs), 7.57 (1H, s), 7.51 (1H, d), 7.40 (2H, t), 7.30 (1H, d), 7.20 (2H, m), 0.35 (1H, m), 4.75 (1H, m), 4.11 (2H, d), 3.68 (1H, dd), 3.26 (2H, m), 3.10 (2H, m), 2.32 (3H, s), 2.09 (2H, m), 1.88 (3H, m), 1.55 (1H, m), 1.40 (1H, m), 0.90 (6H, m). LC/MS: M+1: 406.4.

4-Methyl-2-[4'-(piperidin-4-yloxy)-biphenyl-3-yl]-pentanoic acid cyanomethyl-amide (Compound 171) $^1$HNMR (dmso-d$_6$): δ 8.80 (1H, t), 8.45 (1H, bs), 7.57 (2H, d), 7.53 (1H, s), 7.46 (1H, d), 7.36 (1H, t), 7.25 (1H, d), 7.09 (2H, d), 4.70 (1H, m), 4.11 (2H, d), 3.65 (1H, dd), 3.26 (2H, m), 3.10 (2H, m), 2.10 (2H, m), 1.87 (3H, m), 1.53 (1H, m), 1.40 (1H, m), 0.88 (6H, m). LC/MS: M+1: 405.8.

2-{4'-[1-(2-Hydroxy-ethyl)-piperidin-4-yloxy]-biphenyl-3-yl}-4-methyl-pentanoic acid cyanomethyl-amide (Compound 172) $^1$HNMR (dmso-d$_6$): δ 8.79 (1H, t), 7.53 (3H, d), 7.45 (1H, d), 7.35 (1H, t), 7.23 (1H, d), 7.03 (2H, d), 4.42 (1H, bs), 4.11 (2H, d), 3.65 (1H, dd), 3.50 (2H, m), 2.75 (2H, bs), 2.30 (2H, m), 1.92 (2H, m), 1.65 (1H, m), 1.54 (1H, m), 1.40 (1H, m), 0.88 (6H, m). LC/MS: M+1: 449.6.

4-Methyl-2-[4'-pyrrolidin-3-yloxy)-biphenyl-3-yl]-pentanoic acid cyanomethyl-amide (Compound 173) $^1$HNMR (dmso-d$_6$): δ 9.00 (1H, bs), 8.81 (1H, t), 7.59 (2H, d), 7.54 (1H, s), 7.48 (1H, d), 7.37 (1H, t), 7.25 (1H, d), 7.07 (2H, d), 5.20 (1H, bs), 4.11 (2H, d), 3.67 (1H, dd), 3.41 (4H, m), 2.20 (2H, m), 1.90 (1H, m), 1.53 (1H, m), 1.40 (1H, m), 0.89 (6H, m). LC/MS: M+1: 391.6.

2-[3'-(2-Dimethylamino-ethoxy)-biphenyl-3-yl]-4-methyl-pentanoic acid cyanomethyl-amide (Compound 174) $^1$HNMR (dmso-d$_6$): δ 8.79 (1H, t), 7.57 (1H, s), 7.52 (1H, d), 7.38 (2H, m), 7.28 (1H, m), 7.15 (1H, m), 6.94 (2H, m), 4.11 (2H, d), 4.03 (2H, t), 2.65 (2H, t), 2.24 (6H, s), 2.22 (3H, s), 1.92 (1H, m), 1.55 (1H, m), 1.41 (1H, m), 0.89 (6H, m). LC/MS: M+1: 394.0.

4-{3'-[1-(Cyanomethyl-carbamoyl)-3-methyl-butyl]-biphenyl-4-yloxy}-piperidine-1-carboxylic acid tert-butyl ester (Compound 175) $^1$HNMR (dmso-d$_6$): δ 8.79 (1H, t), 7.54 (2H, d), 7.52 (1H, s), 7.46 (1H, d), 7.36 (1H, t), 7.23 (1H, d), 7.07 (2H, d), 4.61 (1H, m), 4.11 (2H, d), 3.65 (3H, m), 3.20 (2H, m), 1.92 (4H, m), 1.55 (2H, m), 1.40 (10H, m), 0.88 (6H, m).

4-{3'-[1-(Cyanomethyl-carbamoyl)-3-methyl-butyl]-biphenyl-3-yloxy}-piperidine-1-carboxylic acid tert-butyl ester (Compound 176) $^1$HNMR (dmso-d$_6$): δ 8.78 (1H, t), 7.56 (1H, s), 7.51 (1H, d), 7.37 (2H, m), 7.29 (1H, d), 7.18 (2H, m), 7.00 (1H, m), 4.65 (1H, m), 4.11 (2H, d), 3.67 (3H, m), 3.20 (2H, m), 1.93 (3H, m), 1.55 (3H, m), 1.40 (10H, m), 0.90 (6H, m).

3-{3'-[1-(Cyanomethyl-carbamoyl)-3-methyl-butyl]-biphenyl-3-yloxy}-pyrrolidine-1-carboxylic acid tert-butyl ester (Compound 177) 1HNMR (dmso-d$_6$): δ8.78 (1H t), 7.57 (1H, s), 7.51 (1H, d), 7.39 (2H, m), 7.25 (2H, m), 7.14 (1H, s), 7.00 (1H, m), 5.10 (1H, bs), 4.11 (2H, s), 3.66 (1H, m), 3.43 (4H, m), 2.11 (2H, m), 1.93 (1H, m), 1.55 (1H, m), 1.40 (10H, m), 0.89 (6H, m).

3-{3'-[1-(Cyanomethyl-carbamoyl)-3-methyl-butyl]-biphenyl-4-yloxy}-pyrrolidine-1-carboxylic acid tert-butyl ester (Compound 178) $^1$HNMR (dmso-d$_6$): δ 8.78 (1H, t), 7.56 (2H, d), 7.53 (1H, s), 7.46 (1H, d), 7.36 (1H, t), 7.24 (1H, d), 7.04 (2H, d), 5.06 (1H, m), 4.11 (2H, d), 3.65 (1H, m), 3.40 (4H, m), 2.10 (2H, m), 1.91 (1H, m), 1.54 (1H, m), 1.40 (10H, m), 0.88 (6H, m). LC/MS: M+1: 492.

2-[5'-Fluoro-2'-(pyrrolidin-3-yloxy)-biphenyl-3-yl]-4-methyl-pentanoic acid cyanomethyl-amide (Compound 179) $^1$HNMR (dmso-d$_6$): δ 8.87 (2H, m), 7.55 (1H, s), 7.25 (6H, m), 4.98 (1H, bs), 4.13 (2H, t), 3.67 (1H, dd), 3.30 (4H, m), 2.31 (3H, s), 2.12 (2H, m), 1.91 (1H, m), 1.53 (1H m), 1.40 (1H, m), 0.88 (6H, m). LC/MS: M+1: 410.

3-{3'-[1-(Cyanomethyl-carbamoyl)-3-methyl-butyl]-biphenyl-3-yloxy}-pyrrolidine-1-carboxylic acid tert-butyl ester (Compound 180) $^1$HNMR (dmso-d$_6$): δ 8.77 (1H, t), 7.58 (1H, s), 7.50 (1H, d), 7.36 (2H, t), 7.28 (1H, d), 7.20 (1H, d), 7.12 (1H, s), 6.95 (1H, m), 5.10 (1H, bs), 4.10 (2H, d), 3.65 (1H, dd), 3.42 (4H, m), 2.10 (2H, m), 1.901H, m), 1.55 (1H, m), 1.38 (10H, m), 0.89 (6H, m).

4-Methyl-2-[3'-(pyrrolidin-3-yloxy)-biphenyl-3-yl]-pentanoic acid cyanomethyl-amide (Compound 181) $^1$HNMR (dmso-d$_6$): δ 9.00 (1H, bs), 8.80 (1H, t), 7.58 (1H, s), 7.52 (1H, d), 7.40 (2H, m), 7.25 (2H, m), 7.15 (1H, s), 6.98 (1H, dd), 5.25 (1H, bs), 4.10 (2H, d), 3.68 (1H, dd), 3.40 (4H, m), 2.30 (3H, s), 2.20 (2H, m), 1.55(1H, m), 1.38 (1H, m), 0.88 (6H, m).

4-Methyl-2-[3-(2-piperazin-1-ylmethyl-thiazol-4-yl)-phenyl]-pentanoic acid cyanomethyl-amide (Compound 182) $^1$HNMR (dmso-d$_6$): δ 8.84 (1H, t), 8.54 (1H, bs), 8.05 (1H, s), 7.90 (1H, s), 7.78 (1H, d), 7.37 (1H, t), 7.29 (1H, d), 4.10 (2H, d), 3.99 (2H, s), 3.66 (1H, dd), 3.12 (4H, m), 2.74 (4H, m), 2.32 (6H, s), 1.92 (1H, m), 1.53 (1H, m), 1.39 (1H, m), 0.88 (6H, m). LC/MS: M+1: 412.

4-(4-{3-[1-(Cyanomethyl-carbamoyl)-3-methyl-butyl]-phenyl}-thiazol-2-ylmethyl)-piperazine-1-carboxylic acid tert-butyl ester (Compound 183) $^1$HNMR (dmso-d$_6$): δ8.82 (1H, m), 8.02 (1H, s), 7.90 (1H, s), 7.77 (1H, d), 7.37 (1H, t), 7.28 (1H, d), 4.11 (2H, s), 3.91 (2H, s), 3.36 (8H, m), 1.92 (1H, m), 1.52 (1H, m), 1.39 (10H, m), 0.88 (6H, m).

3-{3'-[1-(Cyanomethyl-carbamoyl)-3-methyl-butyl]-5-fluoro-biphenyl-2-yloxy}-pyrrolidine-1-carboxylic acid tert-butyl ester (Compound 184) $^1$HNMR (dmso-d$_6$): δ8.77 (1H, m), 7.47 (1H, m), 7.29 (3H, m), 7.15 (3H, m), 4.92 (1H, bs), 4.09 (2H, m), 3.60 (1H, m), 3.30 (6H, m), 2.00 (3H, m), 1.40 (11H, m), 0.88 (6H, m).

4-Methyl-2-[3'-(pyrrolidin-3-yloxy)-biphenyl-3-yl]-pentanoic acid cyanomethyl-amide (Compound 185) $^1$HNMR (dmso-d$_6$): δ8.98 (1H, bs), 8.82 (3H, t), 7.57 (1H, s), 7.52 (1H, d), 7.41 (2H, m), 7.28 (2H, m), 7.16 (1H, s), 6.99 (1H, m), 5.25 (1H, bs), 4.11 (2H, d), 3.67 (1H, dd), 3.40 (4H, m), 2.21 (2H, m), 1.92 (1H, m), 1.54 (1H, m), 1.39 (1H, m), 0.88 (6H, m).

2-(3-Isoquinolin-4-yl-phenyl)-4-methyl-pentanoic acid cyanomethyl-amide (Compound 186) 1HNMR (dmso-d$_6$): δ9.35 (1H, s), 8.83 (1H, t), 8.43 (1H, s), 8.23 (1H, d), 7.80 (3H, m), 7.47 (4H, m), 4.12 (2H, d), 3.72 (1H, dd), 1.90 (1H, m), 1.58 (1H, m), 1.43 (1H, m), 0.89 (6H, m).

4-Methyl-2-[4'-(toluene-3-sulfonylamino)-biphenyl-3-yl]-pentanoic acid cyanomethyl-amide (Compound 187) $^1$HNMR (dmso-d$_6$): δ 10.37 (1H, s), 8.76 (1H, t), 7.60 (2H, m), 7.48 (6H, m), 7.32 (1H, t), 7.20 (3H, m), 4.09 (2H, d), 3.63 (1H, m), 1.90 (1H, m), 1.52 (1H, m), 1.37 (1H, m), 0.87 (6H, m). LC/MS: M+1: 476.

4-Methyl-2-(4'-nitro-biphenyl-3-yl)-pentanoic acid cyanomethyl-amide (Compound 189) $^1$HNMR (dmso-d$_6$): δ 8.83 (1H, m), 8.33 (2H, d), 7.93 (2H, d), 7.70 (1H, s), 7.66 (1H, m), 7.48 (1H, t), 7.40 (1H, m), 4.11 (2H, d), 3.71 (1H, dd), 1.94 (1H, m), 1.57 (1H, m), 1.41 (1H, m), 0.90 (6H, m). LC/MS: M+1: 352.

2-(2',4'-Dimethoxy-biphenyl-3-yl)-4-methyl-pentanoic acid cyanomethyl-amide (Compound 190) $^1$HNMR (dmso-d$_6$): δ 8.75 (1H, s), 7.32 (2H, d), 7.28 (1H, s), 7.18 (2H, m), 6.60 (2H, m), 4.09 (2H, m), 3.78 (3H, s), 3.73 (3H, s), 3.60 (1H, m), 1.85 (1H, m), 1.53 (1H, m), 1.38 (1H, m), 0.86 (6H, m). LC/MS: M+1: 367.

2-(4'-Methoxy-biphenyl-3-yl)-4-methyl-pentanoic acid cyanomethyl-amide (Compound 191) $^1$HNMR (dmso-d$_6$): δ8.79 (1H, t), 7.57 (2H, d), 7.53 (1H, s), 7.46 (1H, d), 7.36 (1H, t), 7.23 (1H, d), 7.04 (2H, d), 5.22 (2H, s), 4.11 (2H, d), 3.79 (3H, s), 3.65 (1H, dd), 1.92 (1H, m), 1.55 (1H, m), 1.40 (1H, m), 0.88 (6H, m). LC/MS: M+1: 337.

2-(4'-Amino-biphenyl-3-yl)-4-methyl-pentanoic acid cyanomethyl-amide (Compound 192) $^1$HNMR (dmso-d$_6$): δ8.75 (1H, t), 7.45 (1H, s), 7.36 4H, m), 0.81 (1H, d), 6.63 (2H, d), 4.10 (2H, d), 3.61 (1H, dd), 1.89 (1H, m), 1.53 (1H, m), 1.39 (1H, m), 0.88 (6H, m). LC/MS: M+1: 322.

2-(3'-Amino-biphenyl-3-yl)-4-methyl-pentanoic acid cyanomethyl-amide (Compound 193) $^1$HNMR (dmso-d$_6$): δ 8.80 (1H, t), 7.49 (1H, s), 7.36 (2H, m), 7.25 (1H, d), 7.09 (1H, t), 6.80 (1H, t), 6.73 (1H, d), 6.55 (1H, m), 5.15 (2H, s), 4.11 (2H, m), 3.65 (1H, dd), 1.91 (1H, m), 1.54 (1H, m), 1.42 (1H, m), 0.88 (6H, m). LC/MS: M+1: 322.

4-Methyl-2-(3'-nitro-biphenyl-3-yl)-pentanoic acid cyanomethyl-amide (Compound 194) 1HNMR (dmso-d$_6$): δ 8.83 (1H, t), 8.41 (1H, t), 8.24 (1H, m), 8.13 (1H, m), 7.78 (1H, t), 7.69 (1H, s), 7.66 (1H, m), 7.48 (1H, t), 7.39 (1H, d), 4.12 (2H, m), 3.72 (1H, dd), 1.95 (1H, m), 1.57 (1H, m), 1.41 (1H, m), 0.89 (6H, 6H). LC/MS: M+1: 352.

4-Methyl-2-(4'-sulfamoyl-biphenyl-3-yl)-pentanoic acid cyanomethyl-amide (Compound 195) $^1$HNMR (dmso-d$_6$): δ 7.86 (4H, dd), 7.64 (1H, s), 7.60 (1H, d), 1.42 (3H, m), 4.12 (2H, s), 3.70 (1H, dd), 1.92 (1H, m), 1.56 (1H, m), 1.41 (1H, m), 0.89 (6H, m). LC/MS: M: 385.9.

2-(5'-Acetyl-2'-morpholin-4-yl-biphenyl-3-yl)-4-methyl-pentanoic acid cyanomethyl-amide (Compound 196) $^1$HNMR (dmso-d$_6$): δ8.83 (1H, t), 7.90 (1H, m), 7.69 (1H, s), 7.63 (1H, s), 7.43 (3H, m), 7.30 (1H, m), 7.13 (1H, d), 4.10 (2H, d), 3.65 (1H, m), 3.49 (4H, bs), 2.81 (4H, bs), 2.53 (3H, s), 1.95 (1H, m), 1.56 (1H, m), 1.43 (1H, m), 0.89 (6H, m). LC/MS: M+1: 434.

N-(cyanomethyl)-4-methyl-2-[3-(2-methyl-6-quinolinyl)phenyl]pentanamide (Compound 197) $^1$H NMR (400 MHz, d$_6$-DMSO): δ 8.82 (t, J=5.1 Hz, 1H), 8.32 (d, J=8.3 Hz, 1H), 8.17 (s, 1H), 8.00 (s, 2H), 7.73 (s, 1H), 6.67 (d, J=7.6 Hz, 1H), 7.47–7.43 (m, 2H), 7.34 (d, J=7.5 Hz, 1H), 4.12 (d, J=5.2 Hz, 2H), 3.71 (dd, J=7.5, 7.5 Hz, 1H), 2.66 (s, 3H). 2.01–1.93 (m, 1H), 1.62–1.54 (m, 1H), 1.44–1.39 (m, 1H), 0.90 (dd, J=6.7, 6.7 Hz, 6H); MS (−ESI) m/z 370.4 (M−H)$^-$.

N-(cyanomethyl)-4-methyl-2-[3-(3-quinolinyl)phenyl]pentanamide (Compound 198) ¹H NMR (400 MHz, d₆-DMSO): δ 9.22 (s, 1H), 8.84 (t, J=5.1 Hz, 1H), 8.61 (s, 1H), 8.07 (t, J=6.7 Hz, 2H), 7.79–7.73 (m, 3H), 7.65 (t, J=7.3 Hz, 1H), 7.50 (t, 7.6 Hz, 1H), 7.40 (d, J=7.6 Hz, 1H), 4.13 (d, J=4.8 Hz, 2H), 3.74 (dd, J=7.5, 7.5 Hz, 1H), 2.02–1.94 (m, 1H), 1.63–1.56 (m, 1H), 1.47–1.40 (m, 1H), 0.90 (dd, J=7.0 Hz, 6H); MS (−ESI) m/z 306.0 (M−H)⁻

N-(cyanomethyl)-2-[3-(1H-indol-5-yl)phenyl]-4-methylpentanamide (Compound 199) ¹H NMR (400 MHz, d₆-DMSO): δ 11.15 (s, 1H), 8.80 (t, J=6.4 Hz, 1H), 7.77 (s, 1H), 7.59 (s, 1H), 7.51–7.45 (m, 2H), 7.36–7.34 (m, 3H), 7.21 (d, J=7.8 Hz, 1H), 6.48 (s, 1H), 4.11 (d, J=3.2 Hz, 2H), 3.67 (dd, J=7.4, 7.4 Hz, 1H), 1.95–1.90 (m, 1H), 1.59–1.52 (m, 1H), 1.44–1.39 (m, 1H), 0.89 (dd, J=6.6, 6.6 Hz, 6H); MS (−ESI) m/z 344.3 (M−H)⁻.

4-[(tert-butoxycarbonyl)amino]-3'-(1-{[(cyanomethyl)amino]carbonyl}-3-methylbutyl)-1,1'-biphenyl (Compound 200) ¹H NMR (400 MHz, d₆-DMSO): δ 8.80 (t, J=5.1 Hz, 1H), 7.69 (d, J=8.0 Hz, 1H), 7.60 (s, 1H), 7.55 (d, J=7.6 Hz, 1H), 7.44–7.37 (m, 3H), 7.31 (d, J=7.8 Hz, 1H), 4.12 (d, J=3.6 Hz, 2H), 3.69 (dd, J=7.4, 7.4 Hz, 1H), 1.96–1.90 (m, 1H), 1.59–1.52 (m, 1H), 1.43–1.37 (m, 10H), 0.88 (dd, J=6.8, 6.8 Hz, 6H); MS (−ESI) m/z 420.1 (M−H)⁻.

4-{[(tert-butoxycarbonyl)amino]methyl}-3'-(1-{[(cyanomethyl)amino]carbonyl}-3-methylbutyl)-1,1'-biphenyl (Compound 201) ¹H NMR (400 MHz, d₆-DMSO): δ8.79 (br s, 1H), 7.58–7.26 (m, 9H), 4.16 (d, J=5.2 Hz, 2H), 4.11 (br s, 2H), 3.67 (dd, J=7.2, 7.2 Hz, 1H), 1.95–1.91 (m, 1H), 1.57–1.53 (m, 1H), 1.40–1.33 (m, 10H), 0.88 (dd, J=6.7, 6.7 Hz, 6H); MS (−ESI) m/z 434.6 (M−H)⁻.

2-[4'-(aminomethyl)[1,1'-biphenyl]-3-yl]-N-(cyanomethyl)-4-methylpentanamide (Compound 202) ¹H NMR (400 MHz, d₆-acetone): δ8.01 (br s, 1H), 7.65 (s, 1H), 7.57 (d, J=8.0 Hz, 2H), 7.51 (d, J=7.5 Hz, 1H), 7.43 (d, J=8.0 Hz, 2H), 7.38 (t, J=7.6 Hz, 1H), 7.33 (d, J=7.9 Hz, 1H), 4.46 (s, 2H), 4.17 (dd, J=27.6, 17.5 Hz, 2H), 3.76 (dd, J=8.7, 8.7 Hz, 1H), 2.10–1.94 (m, 1H), 1.70–1.63 (m, 1H), 1.53–1.46 (m, 1H), 0.91 (dd, J=6.35, 3.5 Hz, 6H); MS (−ESI) m/z 334.4 (M−H)⁻.

N-(cyanomethyl)-4-methyl-2-[3-(1-methyl-1H-indol-5-yl)phenyl]pentanamide (Compound 203) ¹H NMR (400 MHz, d₆-DMSO): δ 8.81 (t, J=5.4 Hz, 1H), 7.79 (s, 1H), 7.62 (s, 1H), 7.53–7.49 (m, 2H), 7.43 (d, J=8.5 Hz, 1H), 7.39–7.34 (m, 2H), 7.23 (d, J=7.5 Hz, 1H), 6.49 (d, J=2.8 Hz, 1H), 4.13 (dd, J=5.3, 2.2 Hz, 2H), 3.80 (s, 3H), 3.68 (dd, J=7.6, 7.6 Hz, 1H), 1.98–1.91 (m, 1H), 1.61–1.53 (m, 1H), 1.46–1.39 (m, 1H), 0.89 (dd, J=6.6, 6.6 Hz, 6H); MS (−ESI) m/z 359.2 (M−H)⁻.

2-[3-(7-nitro-1H-indol-5-yl)phenyl]-N-(cyanomethyl)-4-methylpentanamide (Compound 204) ¹H NMR (400 MHz, d₆-DMSO): δ11.99 (s, 1H), 8.84 (t, J=5.5 Hz, 1H), 8.35 (s, 1H), 8.30 (d, J=1.3 Hz, 1H), 7.70 (s, 1H), 7.63 (d, J=7.8 Hz, 1H), 7.57 (t, J=2.7 Hz, 1H), 7.43 (d, J=7.7 Hz, 1H), 7.32 (d, J=7.7 Hz, 1H), 6.80 (dd, J=3.0, 1.8 Hz, 1H), 4.13 (dd, J=5.4, 3.4 Hz, 2H), 3.72 (dd, J=8.6, 6.6 Hz, 1H), 2.00–1.93 (m, 1H), 1.61–1.53 (m, 1H), 1.46–1.38 (m, 1H), 0.89 (dd, J=6.9, 6.9 Hz, 6H); MS (−ESI) m/z 389.0 (M−H)⁻.

N-(cyanomethyl)-4-methyl-2-[3-(7-nitro-2,3-dihydro-1H-indol-5-yl)phenyl]pentanamide (Compound 205) ¹H NMR (400 MHz, d₆-DMSO): δ 8.80 (t, J=5.4 Hz, 1H), 8.07 (s, 1H), 7.86 (s, 1H), 7.60 (s, 1H), 7.54 (s, 1H), 7.46 (d, J=7.7 Hz, 1H), 7.35 (t, J=7.6 Hz, 1H), 7.24 (d, J=7.6 Hz, 1H), 4.11 (dd, J=5.3, 2.9 Hz, 2H), 3.79 (t, J=8.4 Hz, 2H), 3.66 (dd, J=8.2, 6.9 Hz, 1H), 3.16 (t, J=8.3 Hz, 2H), 1.97–1.89 (m, 1H), 1.57–1.49 (m, 1H), 1.43–1.35 (m, 1H), 0.88 (dd, J=6.8, 6.8 Hz, 6H); MS (−ESI) m/z 391.3 (M−H)⁻

2-[3-(7-amino-1H-indol-5-yl)phenyl]-N-(cyanomethyl)-4-methylpentanamide (Compound 206) ¹H NMR (400 MHz, d₆-DMSO): δ 10.69 (s, 1H), 8.80 (s, 1H), 7.53 (s, 1H), 7.42 (d, J=7.1 Hz, 1H), 7.34–7.27 (m, 2H), 7.17 (d, J=7.1 Hz, 1H), 7.03 (s, 1H), 6.60 (s, 1H), 6.36 (s, 1H), 5.16 (s, 2H), 4.11 (br s, 2H), 3.64 (dd, J=7.3, 7.3 Hz, 1H), 1.97–1.89 (m, 1H), 1.57–1.51 (m, 1H), 1.43–1.39 (m, 1H), 0.89 (dd, J=6.3, 6.3 Hz, 6H); MS (−ESI) m/z 358.8 (M−H)⁻.

N-(cyanomethyl)-2-(3-{3-[(dimethylamino)methyl]-1H-indol-5-yl}phenyl)-4-methylpentanamide (Compound 207) ¹H NMR (400 MHz, d₆-acetone): δ 10.18 (s, 1H), 7.94 (br s, 2H), 7.66 (s, 1H), 7.53 (d, J=7.8 Hz, 1H), 7.46 (d, J=8.4 Hz, 1H), 7.40–7.34 (m, 2H), 7.30–7.26 (m, 2H), 4.19 (dd, J=11.5, 5.8 Hz, 2H), 3.76 (dd, J=7.7, 7.7 Hz, 1H), 3.63 (s, 2H), 2.21 (s, 6H), 2.08–1.97 (m, 1H), 1.73–1.65 (m, 1H), 1.55–1.48 (m, 1H), 0.96–0.91 (m, 6H); MS (+ESI) m/z 404.4 (M+H)⁺.

N-(cyanomethyl)-4-methyl-2-[3-(1-H-pyrrolo[2,3-b]pyridin-5-yl)phenyl]pentanamide (Compound 208) ¹H NMR (400 MHz, d₆-DMSO): δ 11.72 (s, 1H), 8.80 (br s, 1H), 8.48 (s, 1H), 8.17 (s, 1H), 7.63 (s, 1H), 7.56 (d, J=7.5 Hz, 1H), 7.51 (s, 1H), 7.40 (t, J=7.6 Hz, 1H), 7.28 (d, J=7.4 Hz, 1H), 6.51 (s, 1H), 4.12 (dd, J=2.4, 2.4 Hz, 2H), 3.69 (dd, J=7.5, 7.5 Hz, 1H), 1.98–1.91 (m, 1H), 1.62–1.54 (m, 1H), 1.46–1.38 (m, 1H), 0.89 (dd, J=6.8, 6.8 Hz, 6H); MS (−ESI) m/z 345.4 (M−H)⁻.

2-{3-[3-(2-aminoethyl)-1H-indol-5-yl]phenyl}-N-(cyanomethyl)-4-methylpentanamide (Compound 209) ¹H NMR (400 MHz, d₆-Me₂CO): δ 10.16 (σ, 1H), 8.05 (s, 1H), 7.86 (s, 1H), 7.70 (s, 1H), 7.56 (d, J=7.2 Hz, 1H), 7.45 (d, J=8.4 Hz, 1H), 7.40–7.34 (m, 2H), 7.29 (d, J=7.4 Hz, 1H), 7.19 (s, 1H), 4.18 (dd, J=12.0, 5.5 Hz, 2H), 3.77 (dd, J=7.5, 7.5 Hz, 1H), 3.57–3.53 (m, 2H), 3.07–3.03 (m, 2H), 2.04–2.00 (m, 1H), 1.72–1.65 (m, 1H), 1.55–1.49 (m, 1H), 0.92 (dd, J=6.3, 2.9 Hz, 6H) ppm; MS (+ESI) m/z 411.3 (M+Na)⁺.

(2R)-N-(cyanomethyl)-4-methyl-2-[4'-(4-methyl-1-piperazinyl)[1,1'-biphenyl]-3-yl]pentanamide (Compound 210) ¹H NMR (400 MHz, d₆-DMSO): δ 8.78 (t, J=5.6 Hz, 1H), 7.51–7.46 (m, 3H), 7.44 (d, J=7.9 Hz, 1H), 7.33 (t, J=7.7 Hz, 1H), 7.19 (d, J=7.6 Hz, 1H), 7.01 (d, J=8.8 Hz, 2H), 4.10 (dd, J=5.5, 2.1 Hz, 2H), 3.64 (dd, J=8.6, 6.7 Hz, 1H), 3.19–3.15 (m, 4H), 2.47–2.44 (m, 4H), 2.22 (m, 3H), 1.94–1.87 (m, 1H), 1.57–1.50 (m, 1H), 1.41–1.37 (m, 1H), 0.88 (dd, J=6.8, 6.8 Hz, 6H); MS (+ESI) m/z 405.1 (M+H)⁺.

(2R)-N-(cyanomethyl)-4-methyl-2-[4'-(1-piperazinyl)[1,1'-biphenyl]-3-yl]pentanamide (Compound 211) ¹H NMR (400 MHz, d₆-DMSO): δ 8.80 (t, J=5.5 Hz, 1H), 7.52–7.46 (m, 3H), 7.43 (d, J=7.8 Hz, 1H), 7.33 (t, J=7.7 Hz, 1H), 7.19 (d, J=7.6 Hz, 1H), 6.99 (d, J=8.8 Hz, 2H), 4.11 (dd, J=5.5, 2.2 Hz, 2H), 3.64 (dd, J=8.6, 6.7 Hz, 1H), 3.10–3.06 (m, 4H), 2.85–2.82 (m, 4H), 1.96–1.88 (m, 1H), 1.58–1.50 (m, 1H), 1.42–1.36 (m, 1H), 0.88 (dd, J=6.8, 6.8 Hz, 6H); MS (+ESI) m/z 391.2 (M+H)⁺.

N-(cyanomethyl)-4-methyl-2-[3-(6-quinolinyl)phenyl]pentanamide (Compound 212) ¹H NMR (400 MHz, d₆-Me₂CO): δ 8.90 (dd, J=4.1, 1.7 Hz, 1H), 8.38 (d, J=8.6 Hz, 1H), 8.20 (d, J=1.8 Hz, 1H), 8.12 (d, J=8.8 Hz, 1H), 8.06 (dd, J=8.8, 2.0 Hz, 1H), 7.95 (s, 1H), 7.83 (s, 1H), 7.70 (dd, J=8.2, 1.4 Hz, 1H), 7.52 (dd, J=8.3, 4.2 Hz, 1H), 7.47 (t, J=7.6 Hz, 1H), 7.42 (d, J=7.6 Hz, 1H), 4.21 (dd, J=6.0, 6.0 Hz, 2H), 3.82 (dd, J=7.7, 7.7 Hz, 1H), 2.11–2.04 (m, 1H), 1.74–1.66 (m, 1H), 1.55–1.49 (m, 1H), 0.93 (dd, J=6.6, 3.2 Hz, 6H) ppm. MS (+ESI) m/z 358.1 (M+H)⁺.

N-(cyanomethyl)-3-cyclopropyl-2-[4'-(4-methyl-1-piperazinyl)[1,1'-biphenyl]-3-yl]propanamide (Compound 213) 1H NMR (400 MHz, d$_6$-Me$_2$CO): δ 7.98 (t, J=5.4 Hz, 1H), 7.60 (s, 1H), 7.51 (d, J=8.8 Hz, 2H), 7.45–7.47 (m, 1H), 7.33 (t, J=7.6 Hz, 1H), 7.26 (d, J=7.6 Hz, 1H), 7.00 (d, J=8.8 Hz, 2H), 4.19 (dq, J=5.9, 17.4 Hz, 2H), 3.73 (dd, J=6.4, 8.6 Hz, 1H), 3.19–3.31 (m, 4H), 2.47–2.49 (m, 4H), 2.24 (s, 3H), 1.96–2.05 (m, 1H), 1.64–1.70 (m, 1H), 0.64–0.70 (m, 1H), 0.34–0.43 (m, 2H), 0.03–0.15 (m, 2H) ppm; MS (+ESI) m/z 404.2 (M+H)$^+$.

N-(cyanomethyl)-4-methyl-2-[4'-(1,2,3,6-tetrahydro-4-pyridinyl)[1,1'-biphenyl]-3-yl]pentanamide (Compound 214) $^1$H NMR (400 MHz, d$_6$-Me$_2$CO): δ 8.06 (s, 1H), 7.68 (s, 1H), 7.60 (d, J=8.4 Hz, 2H), 7.55–7.51 (m, 3H), 7.41–7.33 (m, 2H), 6.25 (d, J=1.4 Hz, 1H), 4.18 (dd, J=10.6, 5.8 Hz, 2H), 3.78 (dd, J=7.7, 7.7 Hz, 1H), 3.46–3.45 (m, 2H), 3.03–3.00 (2H), 2.42–2.41 (m, 2H), 2.08–2.01 (m, 1H), 1.71–1.64 (m, 1H), 1.54–1.47 (m, 1H), 0.92 (dd, J=6.6, 3.2 Hz, 6H) ppm; MS (+ESI) m/z 388.2 (M+H)$^+$.

(4S)-N-(cyanomethyl)-4-methyl-2-[4'-(4-methyl-1-piperazinyl)[1,1'-biphenyl]-3-yl]hexanamide (Compound 215) $^1$H NMR (400 MHz, d$_6$-Me$_2$CO): δ8.75, 8.68 (t, t, J=5.4, 5.0, 1H), 7.63 (s, 1H), 7.51 (d, J=8.7 Hz, 2H), 7.43–7.45 (m, 1H), 7.28–7.35 (m, 2H), 7.01 (d, J=8.7 Hz, 2H), 4.06–4.21 (m, 2H), 3.79–3.85 (m, 1H), 3.20–3.23 (m, 4H), 2.48–2.51 (m, 4H), 2.25 (s, 3H), 2.18–2.22 (m, 0.5H), 1.14–1.52 (m, 4.5H), 0.81–0.93 (m, 6H) ppm.

(2R)-N-(cyanomethyl)-2-{4'-[4-(2-hydroxyethyl)-1-piperazinyl][1,1'-biphenyl]-3-yl}-4-methylpentanamide (Compound 216) $^1$H NMR (400 MHz, d$_6$Me$_2$CO): δ 7.91 (t, J=5.4 Hz, 1H), 7.60 (s, 1H), 7.52 (d, J=1.9 Hz, 1H), 7.51 (d, J=2.0 Hz, 1H), 7.46 (m, 1H), 7.34 (t, J=7.7 Hz, 1H), 7.26 (d, J=7.7Hz, 1H), 7.02 (d, J=8.8 Hz, 2H), 4.18 (dd, J=10.4, 5.8 Hz, 2H), 3.74 (dd, J=7.7, 7.7 Hz, 1H), 3.63 (t, J=5.8 Hz, 2H), 3.25–3.21 (m, 4H), 2.65–2.62 (m, 4H), 2.53 (t, J=5.8 Hz, 2H), 2.06–1.98 (m, 1H), 1.70–1.62 (m, 1H), 1.53–1.46 (m, 1H), 0.91 (dd, J=6.6, 3.0 Hz, 6H) ppm; MS (+ESI) m/z 435.1 (M+H)$^+$.

N-(cyanomethyl)-4-methyl-2-[2'-(1-piperazinyl)[1,1'-biphenyl]-3-yl]pentanamide (Compound 217) $^1$H NMR (400 MHz, d$_6$-DMSO): δ8.79 (t, J=5.6 Hz, 1H), 7.62 (s, 1H), 7.39–7.20 (m 4H), 7.14 (d, J=6.4 Hz, 1H), 7.06–7.01 (m, 2H), 4.09 (dd, J=5.2, 5.2 Hz, 2H), 3.62 (dd, J=7.7, 7.7 Hz, 1H), 2.50 (br. s, 4H), 2.49 (br. s, 4H), 1.95–1.87 (m, 1H), 1.57–1.50 (m, 1H), 1.43–1.36 (m, 1H), 0.88 (dd, J=5.9, 5.9 Hz, 6H) ppm; MS (+ESI) m/z 391.1 (M+H)$^+$.

(2R)-N-(cyanomethyl)-4-methyl-2-{3-[6-(1-piperazinyl)-3-pyridinyl]phenyl}pentanamide (Compound 218) $^1$H NMR (400 MHz, d$_6$-Me$_2$CO): δ8.41 (d, J=2.4 Hz, 1H), 7.91 (s, 1H), 7.78 (dd, J=8.9, 2.6 Hz, 1H), 7.59 (s, 1H), 7.46 (d, J=7.7 Hz, 1H), 7.36 (t, J=7.6 Hz, 1H), 7.29 (d, J=7.6 Hz, 1H), 7.23 (d, J=7.3 Hz, 1H), 6.84 (d, J=8.9 Hz, 1H), 4.19 (dd, J=5.5, 3.2 Hz, 2H), 3.74 (dd, J=7.7, 7.7 Hz, 1H), 3.54–3.50 (m, 4H), 2.90–2.87 (m, 4H), 2.08–1.98 (m, 1H), 1.70–1.62 (m, 1H), 1.53–1.46 (m, 1H), 0.91 (dd, J=6.6, 3.5 Hz, 6H) ppm; MS (+ESI) m/z 393.1 (M+H)$^+$.

(2R)-N-(cyanomethyl)-4-methyl-2-[4'-(4-pyridinyl)[1,1'-biphenyl]-3-yl]pentanamide (Compound 219) $^1$H NMR (400 MHz, d$_6$-Me$_2$CO): δ8.64 (dd, J=4.5, 1.6 Hz, 2H), 8.02 (s, 1H), 7.88 (d, J=8.3 Hz, 2H), 7.79 (d, J=8.3 Hz, 2H), 7.74 (s, 1H), 6.70 (dd, J=4.6, 1.6 Hz, 2H), 7.62–7.68 (m, 1H), 7.46–7.39 (m, 2H), 4.20 (dd, J=7.5, 5.9 Hz, 2H), 3.81 (dd, J=7.7, 7.7 Hz, 1H), 2.10–2.02 (m, 1H), 1.73–1.66 (m, 1H), 1.55–1.48 (m, 1H), 0.93 (dd, J=6.6, 3.5 Hz, 6H) ppm; MS (+ESI) m/z 384.0 (M+H)$^+$.

(2R)-N-(cyanomethyl)-2-{4'-[4-(2-hydroxy-2-methylpropyl)-1-piperazinyl][1,1'-biphenyl]-3-yl}-4-methylpentanamide (Compound 220) $^1$H NMR (400 MHz, d$_6$-Me$_2$CO): δ 7.91 (s, 1H), 7.60 (s, 1H), 7.51 (d, J=8.7 Hz, 1H), 7.46 (d, J=7.7 Hz, 1H), 7.34 (t, J=7.6 Hz, 1H), 7.26 (d, J=7.6 Hz, 1H), 7.01 (d, J=8.7 Hz, 2H), 4.17 (dd, J=11.5, 5.8 Hz, 2H), 3.74 (dd, J=7.7, 7.7 Hz, 1H), 3.24–3.21 (m, 4H), 2.77–2.74 (m, 4H), 2.34 (s, 2H), 2.07–1.99 (m, 1H), 1.70–1.63 (m, 1H), 1.53–1.46 (m, 1H), 1.17 (s, 6H), 0.91 (dd, J=6.6, 2.9 Hz, 6H) ppm; MS (+ESI) m/z 384.0 (M+H)$^+$.

N-(cyanomethyl)-4-methyl-2-[4'-(4-piperidinyl)[1,1'-biphenyl]-3-yl]pentanamide (Compound 221) $^1$H NMR (400 MHz, d$_6$-DMSO): δ 8.82 (t, J=5.1 Hz, 1H), 7.55–7.52 (m, 3H), 7.48 (d, J=7.4 Hz, 1H), 7.37 (t, J=7.5 Hz, 1H), 7.31 (d, J=7.6 Hz, 2H), 7.26 (d, J=7.3 Hz, 1H), 4.10 (d, J=3.0, 3.0 Hz, 2H), 3.66 (dd, J=7.4, 7.4 Hz, 1H), 3.06–3.02 (m, 2H), 2.63–2.57 (m, 3H), 1.96–1.88 (m, 1H), 1.72–1.69 (m, 2H), 1.58–1.49 (m, 3H), 1.43–1.36 (m, 1H), 0.88 (dd, J=6.8, 6.8 Hz, 6H) ppm; MS (+ESI) m/z 390.9 (M+H)$^+$.

4-Methyl-2-[4'-(4-methyl-piperazin-1-yl)-biphenyl-3-yl]-pentanoic acid cyanomethyl-amide (Compound 222): $^1$H NMR (DMSO): δ 0.82–0.87 ppm (m, 6H), δ 1.32–1.41 ppm (m. 1H), δ1.46–1.55 ppm (m, 1H), δ1.83–1.94 ppm (m, 1H), δ2.2 ppm (s, 3H), δ2.4 ppm (s, 4H), δ3.15 ppm (s, 4H), δ3.58–3.63 ppm (t, 1H), δ4.08–4.09 ppm (d,m, 2H), δ6.98–7.00 ppm (d,m, 2H), δ7.15–7.17 ppm (d, 1H), δ7.28–7.33 ppm (t,m, 1H), δ7.40–7.47 ppm (m, 4H), δ8.75–8.78 ppm (t,m, 1H). LC/MS (405.2 M+H$^+$).

2-{4'-[4-(2-Hydroxy-ethyl)-piperazin-1-yl]-biphenyl-3-yl}-4-methyl-pentanoic acid (1-cyano-cyclopropyl)-amide (Compound 223): $^1$H NMR (DMSO): δ0.83–0.86 ppm (m, 6H), δ 0.93–1.05 ppm (m. 2H), δ 1.31–1.54 ppm (m, 4H), δ 1.81–1.91 ppm (m, 1H), δ 2.41–2.55 ppm (m, 12H), δ 3.15 ppm (s, 4H), δ 3.47–3.55 ppm (m, 4H), δ 6.97–7.00 ppm (d,m, 2H), δ 7.13–7.15 ppm (d, 1H), δ 7.28–7.33 ppm (t,m, 1H), δ 8.98 ppm (s, 1H). LC/MS (460.8 M+H$^+$).

4-Methyl-2-[3'-(4-methyl-piperazin-1-yl)-biphenyl-3-yl]-pentanoic acid cyanomethyl-amide (Compound 224): $^1$H NMR (DMSO): δ 0.83–0.88 ppm (m, 6H), δ 1.33–1.42 ppm (m. 1H), δ 1.47–1.56 ppm (m, 1H), δ 1.85–1.95 ppm (m, 1H), δ 2.2 ppm (s, 3H), δ 2.44 ppm (s, 4H), δ 3.17 ppm (s, 4H), δ 3.62–3.66 ppm (t, 1H), δ4.08–4.09 ppm (d,m, 2H), δ 6.90–6.93 ppm (d, 1H), δ 6.96–6.99 ppm (d, 1H), δ 7.06 ppm (s, 1H), δ 7.23–7.29 ppm (m, 2H), δ 7.31–7.37 ppm (t,d, 1H), δ 7.45–7.5 ppm (m, 2H), δ8.75–8.79 ppm (m, 1H). LC/MS (404.8 M+H$^+$).

2-(3-{2-[4-(2-Hydroxy-ethyl)-piperazin-1-yl]-thiazol-4-yl}-phenyl)-4-methyl-pentanoic acid (1-cyano-cyclopropyl)-amide (Compound 225): $^1$H NMR (DMSO): δ0.82–0.86 ppm (m, 6H), δ 0.94–1.05 ppm (m. 2H), δ 1.3–1.51 ppm (m, 4H), δ 1.82–1.91 ppm (m, 1H), δ 3.23–3.27 ppm (m, 4H), δ 3.4–3.76 ppm (m, 14H), δ 4.03–4.08 ppm (d, 2H), δ 7.18–7.2 ppm (d, 1H), δ 7.28–7.03 ppm (d, 1H), δ 7.33 ppm (s, 1H), δ 7.67–7.70 ppm (d, 1H), δ 7.73 ppm (s, 1H), δ 9.01 ppm (s, 1H). LC/MS (468.2 M+H$^+$).

2-Biphenyl-3-yl-4-methyl-pentanoic acid (cyano-methyl)-amide (Compound 226) $^1$H NMR (DMSO): δ 0.85–0.9 ppm (t, 6H), δ 1.32–1.34 ppm (d. 2H), δ 1.34–1.44 ppm (m, 2H), δ 1.49–1.58 ppm (m, 1H), δ 1.87–1.96 ppm (m, 1H), δ3.6–3.65 ppm (t, 1H), δ 4.59–4.69 ppm (m, 1H), δ 7.25–7.60 ppm (m, 9H), δ 8.84–8.87 ppm (d, 1H). LC/MS (321 M+H$^+$).

2-Biphenyl-3-yl-4-methyl-pentanoic acid (1-cyano-3-methylsulfanyl-propyl)-amide (Compound 227) $^1$H NMR (DMSO): δ 0.86–0.9 ppm (t, 6H), δ 1.34–1.49 ppm (m. 1H), δ 1.5–1.6 ppm (m, 1H), δ 1.86–2.03 ppm (m, 6H), δ 2.28–2.33 ppm (t, 2H), δ 3.61–3.66 ppm (t, 1H), δ 4.72–4.79 ppm (m, 1H), δ 7.25–7.60 ppm (m, 9H), δ8.85–8.87 ppm (d, 1H). LC/MS (381.2 M+H$^+$).

[5-(2-Biphenyl-3-yl-4-methyl-pentanoylamino)-5-cyano-pentyl]-carbamic acid benzyl ester (Compound 228): $^1$H NMR (DMSO): δ 0.84–0.89 ppm (m, 6H), δ1.12–1.74 ppm (m, 8H), δ 1.86–1.96 ppm (m, 1H), δ 2.81–2.85 ppm (m, 1H), δ 2.9–22.96 ppm (m, 1H), δ 3.62–3.67 ppm (m, 1H), δ 4.57–4.69 ppm (m, 1H), δ 4.93–4.97 ppm (m, 2H), δ 7.16–7.59 ppm (m, 14H), δ 8.8–8.84 ppm (m, 1H). LC/MS (512.2 M+H$^+$).

4-Methyl-2-[3-(4-methyl-piperazin-1-yl)-phenyl]-pentanoic acid cyanomethylamide (Compound 229): $^1$H NMR (DMSO): δ 0.81–0.85 ppm (t,m, 6H), δ 1.27–1.47 ppm (m, 2H), δ 1.78–1.87 ppm (m, 1H), δ 2.18 ppm (s, 3H), δ 2.41 ppm (m, 4H), δ3.04–3.08 ppm (m, 4H), δ 3.45–3.50 ppm (t, 1H), δ 4.05–4.07 ppm (d, 2H), δ 6.66–6.68 ppm (d, 1H), δ 6.73–6.76 ppm (d, 1H), δ 6.82 ppm (s, 1H), δ 7.06–7.11 ppm (t, 1H), δ 8.64–8.68 ppm (t, 1H). LC/MS (329.4 M+H$^+$).

2-Biphenyl-3-yl-4-methyl-pentanoic acid (1-cyano-pentyl)-amide (Compound 230): $^1$H NMR (DMSO): δ 0.81–0.89 ppm (m, 12H), δ 1.09–1.32 ppm (m, 12H), δ1.68–1.95 ppm (m, 5H), δ 3.62–3.67 ppm (t, 1H), δ 4.6–4.72 ppm (m, 1H), δ 4.82–4.87 ppm (t, 1H), δ 7.24–7.61 ppm (m, 9H), δ 8.8–8.86 ppm (t, 1H). LC/MS (363 M+H$^+$)

4-Methyl-2-(3'-piperazin-1-yl-biphenyl-3-yl)-pentanoic acid cyanomethylamide (Compound 231): $^1$H NMR (DMSO): δ 0.84–0.87 ppm (m, 6H), δ 1.03–1.08 ppm (t, 1H), δ 1.33–1.41 ppm (m, 1H), δ1.46–1.55 ppm (m, 1H), δ 1.84–1.93 ppm (m, 1H), δ 2.3 ppm (s, 8H), δ 3.23 ppm (m, 4H), δ 3.39 ppm (m, 4H), δ 3.55 ppm (m, 1H), δ 3.62–3.72 ppm (1H), δ 4.08–4.95 ppm (m, 1H), δ 6.96–6.99 ppm (d, 1H), δ 7.06–7.09 ppm (d, 1H), δ 7.13 ppm (s, 1H), δ 7.25–7.39 ppm (m, 3H), δ 7.44–7.57 ppm (m, 2H), δ 8.78–8.82 ppm (t, 1H). LC/MS (391.07 M+H$^+$).

4-{3'-[1-(Cyanomethyl-carbamoyl)-3-methyl-butyl]-biphenyl-3-yl}-piperazine-1-carboxylic acid tert-butyl ester (Compound 232): $^1$H NMR (DMSO): δ0.84–0.88 ppm (t,m, 6H), δ 1.03 ppm (m, 2H), δ 1.17 ppm (t,m, 1H), δ 1.4 ppm (s, 10H), δ 1.45–1.56 ppm (m, 1H), δ1.86–1.96 ppm (m, 1H), δ 3.13 ppm (m, 4H), δ 3.29 ppm (m, 1H), δ 3.45 ppm (m, 1H), δ 3.67 ppm (t, 1H), δ 4.08–4.10 ppm (m, 2H), δ 6.92–6.95 ppm (d, 1H), δ 7–7.03 ppm (d, 1H), δ 7.09 ppm (s, 1H), δ7.24–7.29 ppm (t, 1H), δ 7.32–7.37 ppm (t, 1H), δ 7.46–7.5 ppm (m, 2H), δ 8.77 ppm (m, 1H). LC/MS (490.4 M+H$^+$).

2-(5-{4-[4-(2-Hydroxy-ethyl)-piperazin-1-yl]-phenyl}-pyridin-3-yl)-4-methylpentanoic acid cyanomethyl-amide (Compound 233) $^1$H NMR (DMSO): δ 0.84–0.89 ppm (t, 6H), δ 1.32–1.43 ppm (m, 1H), δ1.51–1.60 ppm (m, 1H), δ 1.87–1.97 ppm (m, 1H), δ 2.4–2.5 ppm (m, 6H), δ 3.17 ppm (s, 4H), δ 3.49–3.53 ppm (t, 2H), δ3.65–3.70 ppm (t, 1H), δ 4.09–4.11 ppm (d, 2H), δ 7–7.03 ppm (d, 2H), δ 7.51–7.54 ppm (d, 2H), δ 7.85 ppm (s, 1H), δ 8.35 ppm (s, 1H), δ 8.67 ppm (s, 1H), δ 8.85–8.88 ppm (t, 1H). LC/MS (436.2 M+H$^+$).

2-{5-[4-(4-Formyl-piperazin-1-yl)-phenyl]-pyridin-3-yl}-4-methyl-pentanoic acid cyanomethyl-amide (Compound 234) $^1$H NMR (DMSO): δ0.87 ppm (m, 6H), δ1.32–1.43 ppm (m, 1H), δ 1.51–1.60 ppm (m, 1H), δ1.87–1.97 ppm (m, 1H), δ 3.16–3.22 ppm (m, 4H), δ 3.5 ppm (s, 4H), δ 3.65–3.7 ppm (t, 1H), δ 4.09–4.11 ppm (m, 2H), δ 7.05–7.08 ppm (d, 2H), δ 7.54–7.57 ppm (d, 2H), δ 7.85 ppm (s, 1H), δ 8.06 ppm (s, 1H), δ 8.36 ppm (s, 1H), δ 8.67 ppm (s, 1H), δ 8.85–8.88 ppm (t, 1H). LC/MS (420.2 M+H$^+$).

4-Methyl-2-[5-(4-piperazin-1-yl-phenyl)-pyridin-3-yl]-pentanoic acid cyanomethyl-amide (Compound 235) $^1$H NMR (DMSO): δ 0.84–0.89 ppm (t, 6H), δ1.3–1.41 ppm (m, 1H), δ 1.55–1.64 ppm (m, 1H), δ1.88–1.98 ppm (m, 1H), δ 3.23 ppm (m, 4H), δ 3.41 ppm (m, 4H), δ 3.72–3.78 ppm (t, 1H), δ 4.1–4.11 ppm (d,m, 2H), δ 7.09–7.12 ppm (d, 2H), δ 7.61–7.65 ppm (d, 2H), δ 8.06 ppm (s, 1H), δ 8.45 ppm (s, 1H), δ 8.79 ppm (s, 1H), δ 8.9–8.95 ppm (t, 1H). LC/MS (392.4 M+H$^+$).

3'-[1-(Cyanomethyl-carbamoyl)-3-methyl-butyl]-biphenyl-2-carboxylic acid methyl ester (Compound 236) (CDCl$_3$) $^1$H NMR δ 7.95 (d, 1H), δ 7.61–7.18 (m, 8H), δ 6.30 (s, 1H), δ 4.08(d, 2H), δ 3.74 (s, 3H), δ 3.59 (t, 1H), δ 2.01 (m, 1H), δ1.84 (s, br, 1H), δ 1.71 (s, 1H), δ 1.47 (m, 1H), δ 1.24 (s, 1H), δ 0.89 (m, 6H). M+H$^+$=365.2

2-[3-(2,3-Dihydro-benzo[1,4]dioxin-6-yl)-phenyl]-4-methyl-pentanoic acid cyanomethyl-amide (Compound 237) (CD$_2$Cl$_2$) $^1$H NMR δ 7.50–6.90 (m, 7H), δ4.30 (m, 4H), δ 4.25–3.97 (m, 2H), δ 4.35(t, 1H), δ 2.05 (m, 1H), δ 1.86–1.19 (dd, 4H), δ 0.89 (d, 6H). M+H$^+$=365.2

2-[4'-(1-Hydroxy-ethyl)-biphenyl-3-yl]-4-methyl-pentanoic acid cyanomethylamide (Compound 238) (DMSO) $^1$H NMR δ 8.78 (t, 1H), δ 7.62–7.23 (m, 8H), δ4.73 (m, 1H), δ 4.08 (d, 2H), δ 4.07 (m, 2H), δ 3.64 (t, 1H), δ 1.90 (s, br, 1H), δ1.52(m, 1H), δ 1.44–1.18 (m, 4H), δ 0.85 (m, 6H). M+H$^+$=351.1.

2-(3',5'-Bis-trifluoromethyl-biphenyl-3-yl)-4-methyl-pentanoic acid cyanomethyl-amide (Compound 239) (DMSO) $^1$H NMR δ 8.78 (m, 1H), δ 8.25 (s, 2H), δ 8.09 (s. 1H), δ 7.70 (m, 1H), δ 7.50–7.37 (m, 2H), δ 4.01 (m, 2H), δ 3.70 (m, 1H), δ 1.94(s, 1H), δ 1.53 (m, 1H), δ 1.39 (m, 1H), δ 0.87 (m, 6H).

2-(4'-Cyano-2'-methyl-biphenyl-3-yl)-4-methyl-pentanoic acid cyanomethylamide (Compound 240) (DMSO) $^1$H NMR δ 8.78 (m, 1H), δ 7.78 (s, 1H), δ 7.71 (d, 1H), δ 7.45–7.18 (m, 5H), δ 7.50–7.37 (m, 2H), δ 4.01 (m, 2H), δ 3.70 (m, 1H), δ1.94(s, 1H), δ 1.53 (m, 1H), δ 1.39 (m, 1H), δ 0.87 (m, 6H).

N-[1-(Cyanomethyl-carbamoyl)-2-(2-fluoro-3-methylphenylmethanesulfonyl)-ethyl]-benzamide (Compound 241) (DMSO) $^1$H NMR δ8.74 (m, 1H), δ 7.40–6.97 (m, 7H), δ 4.07 (m, 2H), δ 3.60 (m, 1H), δ 2.18(m, 4H), δ1.78 (m, 1H), δ 1.55 (m, 1H), δ 1.32 (m, 1H), δ 1.19 (m, 1H), δ 0.97–0.79 (m, 12H).

N-[1-(Cyanomethyl-carbamoyl)-2-(2,5-difluoro-phenylmethanesulfonyl)ethyl]-benzamide (Compound 242) (DMSO) $^1$H NMR δ 8.79 (m, 1H), δ 8.26 (m, 1H), δ 8.05 (m, 1H), δ 7.46–7.27 (m, 5H), δ 4.07 (m, 2H), δ 3.88 (s, 3H), δ 3.64(m, 1H), δ 1.95 (m, 1H), δ 1.85 (m, 1H), δ 1.53 (m, 1H), δ 1.37 (m, 1H), δ 1.19–1.0 (m, 2H), δ 0.85 (m, 6H). M+H$^+$=382.2.

2-{3'-[4-(2-Hydroxy-ethyl)-piperazine-1-sulfonyl]-4'-methoxy-biphenyl-3-yl}-4-methyl-pentanoic acid cyanomethyl-amide (Compound 243) (DMSO) $^1$H NMR δ9.58 (s, br, 1H), δ 8.84 (m, 1H), δ 7.92 (m, 2H), δ 7.55–7.24 (m, 5H), δ 5.38 (m, 1H), δ 4.08 (m, 2H), δ 3.70 (m, 4H), δ 3.71 (d, 4H), δ 3.13 (m, 4H), δ 1.90 (m, 1H), δ1.51 (m, 1H), δ 1.36 (m, 1H), δ 0.85 (m, 6H). M+H$^+$=529.2.

3'-[1-(Cyanomethyl-carbamoyl)-3-methyl-butyl]-biphenyl-4-carboxylic acid (2-morpholin-4-yl-ethyl)-amide (Compound 244) (DMSO) $^1$H NMR δ 8.80 (s, br, 1H), δ 7.94 (d, 2H), δ 7.74 (d, 2H), δ 7.68–7.54 (m, 2H), δ 7.45–7.28 (m, 2H), δ4.08 (m, 2H), δ 4.0–2.98 (m, 8H), δ 2.47 (m, 4H), δ 1.90 (m, 1H), δ 1.51 (m, 1H), δ1.36 (m, 1H), δ 0.85 (m, 6H). M+H$^+$=463.2.

3'-[1-(Cyanomethyl-carbamoyl)-3-methyl-butyl]-biphenyl-3-carboxylic acid (2-morpholin-4-yl-ethyl)-amide (Compound 245) (DMSO) ¹H NMR δ 9.85 (s, br, 1H), δ 8.86 (d, 2H), δ 8.08(s, 1H), δ 7.82 (dd, 2H), δ 7.60 (s, 1H), δ 7.56 (d, 2H), δ7.42 (t, 1H), δ 7.31 (d, 1H), δ 4.08 (m, 2H), δ 3.98 (m, 2H), δ 3.73–3.47 (m, 8H), δ3.13 (m, 2H), δ 2.47 (m, 4H), δ 1.92 (m, 1H), δ 1.52 (m, 1H), δ 1.36 (m, 1H), δ 0.85 (m, 6H). M+H$^+$=463.2.

4-Methyl-2-[3'-(2-morpholin-4-yl-ethylsulfamoyl)-biphenyl-3-yl]-pentanoic acid cyanomethyl-amide (Compound 246) (DMSO) ¹H NMR δ 8.81 (m, 1H), δ7.87 (d, 2H), δ 7.77(d, 1H), δ 7.70–7.50 (m, 4H), δ 7.45 (t, 1H), δ 7.33 (d, 2H), δ7.42 (t, 1H), δ 7.31 (d, 1H), δ 4.08 (m, 2H), δ 3.67 (m, 2H), δ 3.47 (m, 4H), δ 2.88 (m, 2H), δ 2.31–2.15 (m, 6H), δ 1.92 (m, 1H), δ 1.52 (m, 1H), δ 1.36 (m, 1H), δ 0.85 (m, 6H). M+H$^+$=499.2.

3'-[1-(Cyanomethyl-carbamoyl)-3-methyl-butyl]-biphenyl-2-carboxylic acid (2-morpholin-4-yl-ethyl)-amide (Compound 247) (DMSO) ¹H NMR δ 8.91 (m, 1H), δ 8.44(m, 1H), δ 7.91(d, 2H), δ 7.55–7.15 (m, 8H), δ 4.92 (s, br, 8H), δ 4.00–3.4 (m, 11H), δ 3.0 (m, 4H), δ 1.85 (m, 1H), δ 1.41 (m, 1H), δ 1.26 (m, 1H), δ 0.85 (m, 6H). M+H$^+$=463.2.

3'-[1-(Cyanomethyl-carbamoyl)-3-methyl-butyl]-biphenyl-4-carboxylic acid (2-dimethylamino-ethyl)-methyl-amide (Compound 248) (DMSO) ¹H NMR δ 8.79 (m, 1H), δ 7.66 (d, 2H), δ 7.59(s, 1H), δ 7.53(d, 1H), δ 7.43 (d, br, 8H), δ 7.39 (t, 1H), δ 7.30 (d, 1H), δ 4.00 (d, 2H)), δ 3.65 (t, 1H), δ 3.52 (s, 1H), δ 3.34–3.24 (d, 4H), δ2.94 (d, 4H), δ 2.38–1.84 (m, 9H), δ 1.51 (m, 1H), δ 1.36 (m, 1H), δ 0.85 (m, 6H). M+H$^+$=434.6.

3'-[1-(Cyanomethyl-carbamoyl)-3-methyl-butyl]-biphenyl-4-carboxylic acid (2-dimethylamino-ethyl)-amide (Compound 249) (DMSO) ¹H NMR δ 8.79 (m, 1H), δ 8.43 (d, 1H), δ 7.90(d, 2H), δ 7.69(d, 2H), δ 7.60 (s, 1H), δ 7.55 (d, 1H), δ 7.40 (t, 1H), δ 7.30 (d, 1H), δ 4.00 (d, 2H)), δ 3.65 (t, 1H), δ 2.39 (s, 4H), δ 2.16 (s, 6H), δ1.92 (m, 9H), δ 1.51 (m, 1H), δ 1.36 (m, 1H), δ 0.85 (m, 6H). M+H$^+$=420.8.

3'-[1-(Cyanomethyl-carbamoyl)-3-methyl-butyl]-biphenyl-4-carboxylic acid methyl-(2-morpholin-4-yl-ethyl)-amide (Compound 250) (CDCl₃) ¹H NMR δ 8.78 (s, 1H), δ 7.70–7.26 (m, 8H), δ 4.08(d, 2H), δ 3.74–3.22 (m, 9H), δ 2.94 (s, 3H), δ2.27 (d, 4H), δ 1.91 (s, br, 1H), δ 1.54 (s, 1H), δ 1.38 (m, 1H), δ 0.89 (m, 6H). M+H$^+$=476.4.

2-(3'-Fluoro-biphenyl-3-yl)-4-methyl-pentanoic acid cyanomethyl-amide (Compound 251) (CDCl₃) ¹H NMR δ 7.5–7.23 (m, 7H), δ 7.04 (m, 1H), δ 6.12(t, 1H), δ 4.14 (dd, 1H), δ 4.0 (dd, 1H), δ 3.56(t, 1H), δ 2.0 (m, 1H), δ 1.76 (m, 1H), δ1.45(m, 1H), δ 0.89(m, 6H).

2-[3-(6-Bromo-pyridin-2-yl)-phenyl]-4-methyl-pentanoic acid cyanomethylamide (Compound 252) (CDCl₃) ¹H NMR δ 7.81–7.74 (m, 2H), δ 7.66–7.53 (m, 2H), δ 7.43–7.31 (m, 3H), δ 6.64(t, 1H), δ 4.12 (dd, 1H), δ 3.93 (dd, 1H), δ 3.54(t, 1H), δ 2.0 (m, 1H), δ 1.76 (m, 1H), δ 1.40 (m, 1H), δ 0.89 (m, 6H).

2-(2'-Cyano-biphenyl-3-yl)-4-methyl-pentanoic acid cyanomethyl-amide (Compound 253) M+H$^+$=332.04.

2-(3'-Cyano-biphenyl-3-yl)-4-methyl-pentanoic acid cyanomethyl-amide (Compound 254) M+H$^+$=331.99.

2-(4'-Cyano-biphenyl-3-yl)-4-methyl-pentanoic acid cyanomethyl-amide (Compound 255) M+H$^+$=332.00.

4-Methyl-2-(3-quinolin-8-yl-phenyl)-pentanoic acid cyanomethyl-amide (Compound 256) (CDCl₃) ¹H NMR δ 8.88 (m, 1H), δ 8.30–7.20 (m, 8H), δ 6.90 (m, 1H), δ 4.05 (dd, 1H), δ 3.85 (dd, 1H), δ 3.45(t, 1H), δ 2.77 (s, br, 1H), δ 2.0 (m, 1H), δ 1.80 (m, 1H), δ 1.45 (m, 1H), δ 0.89 (m, 6H). M+H$^+$=358.01.

4-Methyl-2-(3-quinolin-3-yl-phenyl)-pentanoic acid cyanomethyl-amide (Compound 257) (CDCl₃) ¹H NMR δ 8.95 (s, br, 1H), δ 8.14 (d, 1H), δ 8.05 (d, 1H), δ 7.86–7.22 (m, 8H), δ 4.14 (m, 2H), δ 3.61(t, 1H), δ 2.38 (s, br, 1H), δ 2.0 (m, 1H), δ 1.74 (m, 1H), δ 1.48 (m, 1H), δ 1.22 (m, 1H), δ 0.89 (m, 6H).

4-Methyl-2-(4'-trifluoromethoxy-biphenyl-3-yl)-pentanoic acid cyanomethylamide (Compound 258) M+H$^+$=391.0.

4-Methyl-2-[3-(5-nitro-thiazol-2-yl)-phenyl]-pentanoic acid cyanomethylamide (Compound 259) (CDCl₃) ¹H NMR δ 8.51 (s, 1H), δ 7.87 (s, 1H), δ 7.79 (dt, 1H), δ 7.50–7.40 (m, 2H), δ 5.84 (t, 1H), δ 4.15 (dd, 1H), δ 4.03 (dd, 1H), δ 3.48(t, 1H), δ 1.99 (dt, 1H), δ 1.70 (m, 1H), δ 1.74 (m, 1H), δ 1.41 (m, 1H), δ 0.89 (m, 6H).

2-(4'-Acetylamino-biphenyl-3-yl)-4-methyl-pentanoic acid cyanomethylamide (Compound 260) (CDCl₃) ¹H NMR δ 7.85 (s, 1H), δ 7.55–7.28 (m, 8H), δ6.75 (s, 1H), δ 4.14–3.85 (m, 2H), δ 3.58(t, 1H), δ 2.15 (s, 3H), δ 2.05–1.60 (m, 3H), δ 1.55 (m, 1H), δ 0.89 (m, 6H).

4-Methyl-2-[4'-(4-methyl-piperazine-1-sulfonyl)-biphenyl-3-yl]-pentanoic acid cyanomethyl-amide (Compound 261) ¹H NMR (DMSO) δ 8.88 (t, 1H), δ 7.86 (d, 2H), δ 7.78 (d, 2H), δ 7.63 (s, 1H), δ 7.59 (d, 1H), δ 7.44 (t, 1H), δ 7.35 (d, 1H), δ4.08 (d, 2H), δ 3.70(t, 1H), δ 2.88 (s, br, 4H), δ 2.34 (s, 4H), δ 2.10 (s, 3H), δ 1.94–1.86 (m, 1H), δ 1.58–1.49 (m, 1H), δ1.39–1.32 (m, 1H), δ 0.86 (m, 6H). MS M+H$^+$=469.2

4-Methyl-2-[3'-(4-methyl-piperazine-1-sulfonyl)-biphenyl-3-yl]-pentanoic acid cyanomethyl-amide (Compound 262) ¹H NMR (DMSO) δ 8.77 (t, 1H), δ7.97 (d, 1H), δ 7.67 (t, 1H), δ 7.58 (t, 1H), δ 7.35–7.19 (m, 5H), δ 4.07 (d, 2H), δ3.61 (t, 2H), δ 2.47 (s, br, 4H), δ 2.05 (s, 8H), δ 1.94–1.81 (m, 1H), δ 1.58–1.49 (m, 1H), δ 1.39–1.32 (m, 1H), δ 0.86 (m, 6H). MS M+H$^+$=469.2

4-Methyl-2-[4'-(piperazine-1-sulfonyl)-biphenyl-3-yl]-pentanoic acid cyanomethyl-amide (Compound 263) ¹H NMR (DMSO) δ 8.82 (t, 1H), δ 7.89 (d, 2H), δ 7.79 (d, 2H), δ 7.65 (s, 1H), δ 7.60 (d, 1H), δ 7.46 (t, 1H), δ 7.36 (d, 1H), δ4.11 (m, 2H), δ 3.69 (dd, 1H), δ 2.80 (m, 4H), δ 2.72 (s, 4H), δ 1.94 (m, 1H), δ 1.58 (m,1H), δ 1.39 (m, 1H), δ 0.88 (m, 6H). MS M+H$^+$=454.6

2-{4'-[4-(2-Hydroxy-ethyl)-piperazine-1-carbonyl]-biphenyl-3-yl}-4-methylpentanoic acid cyanomethyl-amide (Compound 264) ¹H NMR (DMSO) δ 8.80 (t, 1H), δ 7.68 (d, 2H), δ 7.62 (s, 1H), δ 7.55 (d, 1H), δ 7.50–7.31 (m, 5H), δ 4.11 (d, 2H), δ 3.69–3.30 (m, 9H), δ 2.50–2.42 (m, 4H), δ 1.94 (m, 1H), δ 1.58 (m, 1H), δ1.41 (m, 1H), δ 0.89 (m, 6H). MS M+H$^+$=463.2

2-{3'-[4-(2-Hydroxy-ethyl)-piperazine-1-carbonyl]-biphenyl-3-yl}-4-methylpentanoic acid cyanomethyl-amide (Compound 265) ¹H NMR (in DMSO) δ 8.80 (t, 1H), δ 7.68–7.31 (m, 8H), δ 4.11 (d, 2H), δ 3.75–3.20 (m, 9H), δ 2.50–2.30 (m, 4H), δ 1.94 (m, 1H), δ 1.58 (m, 1H), δ 1.41 (m, 1H), δ 0.89 (m, 6H). MS M+H$^+$=463.2

4-Methyl-2-[4'-(2-morpholin-4-yl-ethylsulfamoyl)-biphenyl-3-yl]-pentanoic acid cyanomethyl-amide (Compound 266) ¹H NMR (DMSO) δ 8.80 (t, 1H), δ 7.88 (d, 2H), δ 7.83 (d, 2H), δ 7.63 (s, 1H), δ 7.58 (d, 1H), δ 7.44 (t, 1H), δ 7.35 (d, 1H), δ4.10 (d, 2H), δ 3.68 (dd, 1H), δ 3.48 (t, 4H), δ 2.88 (t, 2H), δ 2.30–2.23 (m, 6H), δ1.91 (m, 1H), δ 1.58 (m, 1H), δ 1.41 (m, 1H), δ 0.89 (m, 6H). MS M+H$^+$=499.4

2-(4'-{2-[Bis-(2-hydroxy-ethyl)-amino]-ethylsulfamoyl}-biphenyl-3-yl)-4-methyl-pentanoic acid cyanomethyl-amide (Compound 267) ¹H NMR (in DMSO) δ 8.82 (t, 1H), δ 7.92–7.82 (m, 4H), δ 7.65 (s, 1H), δ 7.60 (d, 1H), δ 7.45 (t, 1H), δ7.36 (d, 1H), δ 4.33 (t, 1H), δ 4.12 (d, 2H), δ 3.72 (t, 1H), δ 3.56 (t, 1H), δ 3.34 (s, 4H), δ 2.91–2.80 (m, 2H), δ 2.45 (m, 6H), δ 1.95 (m, 1H), δ 1.58 (m, 1H), δ 1.41 (m, 1H), δ 0.89 (m, 6H). MS M+H⁺=517.2

4-Methyl-2-[4'-(3-morpholin-4-yl-propylsulfamoyl)-biphenyl-3-yl]-pentanoic acid cyanomethyl-amide (Compound 268) ¹H NMR (in DMSO) δ 8.19 (t, 1H), δ7.89–7.82 (m, 4H), δ 7.64 (s, 1H), δ 7.59 (d, 1H), δ 7.45 (t, 1H), δ 7.36 (d, 1H), δ4.10 (d, 2H), δ 3.70 (dd, 1H), δ 3.49 (t, 4H), δ 2.81 (t, 2H), δ 2.22 (m, 6H), δ 1.95 (m, 1H), δ 1.54 (m, 1H), δ 1.43 (m, 1H), δ 0.89 (m, 6H). MS M+H⁺=513.4

4-Methyl-2-[4'-(3-morpholin-4-yl-propylsulfamoyl)-biphenyl-3-yl]-pentanoic acid cyanomethyl-amide (Compound 269) ¹H NMR (DMSO) δ 8.19 (t, 1H), δ 7.89–7.82 (m, 4H), δ 7.64 (s, 1H), δ 7.59 (d, 1H), δ 7.45 (t, 1H), δ 7.36 (d, 1H), δ 4.10 (d, 2H), δ 3.70 (dd, 1H), δ 3.49 (t, 4H), δ 2.81 (t, 2H), δ 2.22 (m, 6H), δ 1.95 (m, 1H), δ1.54 (m, 1H), δ 1.43 (m, 1H), δ 0.89 (m, 6H). MS M+H⁺=513.4

2-[4'-(2-Dimethylamino-1-methyl-ethylsulfamoyl)-biphenyl-3-yl]-4-methylpentanoic acid cyanomethyl-amide (Compound 270) MS M+H⁺=471.2

2-[4'-(2-Hydroxy-ethylsulfamoyl)-biphenyl-3-yl]-4-methyl-pentanoic acid cyanomethyl-amide (Compound 271) MS M+H⁺=430.2

2-[4'-(2-Hydroxy-ethylsulfamoyl)-biphenyl-3-yl]-4-methyl-pentanoic acid cyanomethyl-amide (Compound 272) APC-014358 MS M+H⁺=477.0

2-[4'-(3-Dimethylamino-pyrrolidine-1-sulfonyl)-biphenyl-3-yl]-4-methylpentanoic acid cyanomethyl-amide (Compound 273) ¹H NMR (in DMSO) δ 8.73 (t, 1H), δ 7.80 (s, 4H), δ 7.58 (s, 1H), δ 7.37 (d, 1H), δ 7.29 (d, 1H), δ 4.02 (d, 2H), δ3.62 (dd, 1H), δ 3.33–3.21 (m, 6H), δ 3.05 (m, 1H), δ 2.78 (t, 1H), δ 1.95 (s, 6H), δ1.85 (m, 1H), δ 1.48 (m, 1H), δ 1.34 (m, 1H), δ 0.89 (m, 6H). MS M+H⁺=482.4

4-Methyl-2-{4'-[methyl-(1-methyl-pyrrolidin-3-yl)-sulfamoyl]-biphenyl-3-yl)}-pentanoic acid cyanomethyl-amide (Compound 274) ¹H NMR (in DMSO) δ8.81 (t, 1H), δ 7.86 (s, 4H), δ 7.67 (s, 1H), δ 7.62 (d, 1H), δ 7.45 (t, 1H), δ 7.36 (t, 1H), δ 4.52 (m, 1H), δ 4.11 (d, 2H), δ 3.70 (dd, 1H), δ 2.72 (s, 3H), δ 2.59 (m, 1H), δ2.36–2.25 (m, 2H), δ 2.12–1.87 (m, 6H), δ 1.58–1.41 (m, 3H), δ 0.89 (m, 6H). MS M+H⁺=483.0

2-[4'-(4-Formyl-piperazine-1-sulfonyl)-biphenyl-3-yl]-4-methyl-pentanoic acid cyanomethyl-amide (Compound 275) ¹H NMR (in DMSO) δ 8.81 (t, 1H), δ7.92 (s, 1H), δ 7.88 (d, 2H), δ 7.80 (d, 2H), δ 7.65 (s, 1H), δ 7.61 (d, 1H), ), δ 7.46 (t, 1H), ), δ 7.36 (d, 1H), δ 4.10 (m, 1H), δ 4.11 (d, 2H), δ 3.45 (t, 1H), δ 3.40 (m, 4H), δ 2.96 (m, 4H), δ 1.94 (m, 1H), δ 1.58 (m, 1H), δ 1.39 (m, 1H), δ 0.89 (m, 6H). MS M+H⁺=483.2.

4-Methyl-2-[4'-(2-piperazin-1-yl-thiazol-4-yl)-biphenyl-3-yl]-pentanoic acid (1-cyano-cyclopropyl)-amide (Compound 276): ¹H NMR (DMSO-d₆, ppm): δ 0.91 (d, 6H), 1.42 (m, 3H), 3.51 (m, 4H), 3.81 (m, 4H), 4.01 (m, 2H), 4.81 (m, 1H), 7.12–7.78 (m, 9H), 8.81 (m, 2H). ES-Ms: 500.1 (M+H⁺).

4-Methyl-2-[4'-(2-piperazin-1-yl-thiazol-4-yl)-biphenyl-3-yl]-pentanoic acid cyanomethyl-amide (Compound 277): ¹H NMR (DMSO-d₆, ppm): δ 0.91 (d, 6H), 1.22–1.42 (m, 2H), 1.81 (m, 1H), 3.31 (m, 4H), 3.81 (m, 4H), 4.11 (m, 2H), 7.12–7.78 (m, 7H), 8.01 (m, 2H), 8.81 (m, 2H). ES-Ms: 474.3 (M+H⁺).

4-Methyl-2-[3'-(2-piperazin-1-yl-thiazol-4-yl)-biphenyl-3-yl]-pentanoic acid (1-cyano-cyclopropyl)-amide (Compound 278): ¹H NMR (DMSO-d₆, ppm): δ 0.91–1.07 (m, 8H), 1.22–1.42 (m, 4H), 1.81 (m, 1H), 3.41 (m, 4H), 3.81 (m, 2H), 3.91 (m, 4H), 7.12–7.78 (m, 9H), 8.81 (m, 2H). ES-Ms: 500.3 (M+H⁺).

The following named compounds of Formula I are provided by the methods described in this Application:

N-cyanomethyl-4-methyl-2-(3-pyrid-2-ylphenyl)pentanamide; N-cyanomethyl-4-methyl-2-(3-pyrid-3-ylphenyl)pentanamide; N-cyanomethyl-4-methyl-2-(3-pyrid-4-ylphenyl)pentanamide; 2-[3-(6-aminopyrid-3-yl)phenyl]-N-cyanomethyl-4-methylpentanamide; N-cyanomethyl-2-[3-(4,6-dimethylpyrid-2-yl)phenyl]-4-methylpentanamide; N-cyanomethyl-4-methyl-2-(3-thien-2-ylphenyl)pentanamide; N-cyanomethyl-4-methyl-2-(3-thiazol-2-ylphenyl)pentanamide; N-cyanomethyl-4-methyl-2-(4'-sulfamoylbiphenyl-3-yl)pentanamide; N-cyanomethyl-2-(2',6'-dimethoxybiphenyl-3-yl)-4-methylpentanamide; N-cyanomethyl-2-(3'-fluorobiphenyl-3-yl)-4-methylpentanamide; 2-[4'-(2-aminothiazol-4-yl)biphenyl-3-yl]-N-cyanomethyl-4-methylpentanamide; N-cyanomethyl-4-methyl-2-(4'-pyrrol-1-ylbiphenyl-3-yl)pentanamide; N-cyanomethyl-4-methyl-2-[4'-(2H-tetrazol-5-yl)biphenyl-3-yl]pentanamide; N-cyanomethyl-2-[3-(6-bromopyrid-3-yl)phenyl]-4-methylpentanamide; N-cyanomethyl-2-[3-(6-bromopyrid-2-yl)phenyl]-4-methylpentanamide; N-cyanomethyl-2-(4'-[1,3]dioxolan-2-ylbiphenyl-3-yl)-4-methylpentanamide; N-cyanomethyl-2-[3-(2,3-dihydrobenzo[1,4]dioxin-6-yl)phenyl]-4-methylpentanamide; N-cyanomethyl-2-(3-benzo[1,3]dioxol-5-ylphenyl)-4-methylpentanamide; N-cyanomethyl-2-[4'-(1-hydroxyethyl)biphenyl-3-yl]-4-methylpentanamide; methyl 3'-[1-(cyanomethylcarbamoyl)-3-methylbutyl]biphenyl-2-carboxylate; N-cyanomethyl-2-(4'-dimethylaminobiphenyl-3-yl)-4-methylpentanamide; N-cyanomethyl-2-(4'-cyano-2'-methylbiphenyl-3-yl)-4-methylpentanamide; N-cyanomethyl-4-methyl-2-(3-quinolin-6-ylphenyl)pentanamide; N-cyanomethyl-4-methyl-2-(3-quinolin-7-ylphenyl)pentanamide; N-cyanomethyl-4-methyl-2-(3-quinolin-8-ylphenyl)pentanamide; 2-(2'-cyanobiphenyl-3-yl)-N-cyanomethyl-4-methylpentanamide; N-cyanomethyl-2-[3-(1H-indol-5-yl)phenyl]-4-methylpentanamide; N-cyanomethyl-2-(3',5'-bis-trifluoromethylbiphenyl-3-yl)-4-methylpentanamide; 2-(2'-chloro-5'-hydroxybiphenyl-3-yl)-N-cyanomethyl-4-methylpentanamide; N-cyanomethyl-2-[4'-(4-hydroxypiperidin-4-yl)biphenyl-3-yl]-4-methylpentanamide; N-cyanomethyl-4-methyl-2-[3-(1-oxoindan-5-yl)phenyl]pentanamide; 2-(4'-acetylaminobiphenyl-3-yl)-N-cyanomethyl-4-methylpentanamide; N-cyanomethyl-4-methyl-2-[3-(5-nitrothiazol-2-yl)phenyl]pentanamide; N-cyanomethyl-4-methyl-2-[3'-(4-methylpiperazin-1-ylcarbonyl)biphenyl-3-yl]pentanamide; N-cyanomethyl-4-methyl-2-(3'-morpholin-4-ylbiphenyl-3-yl)pentanamide; N-cyanomethyl-4-methyl-2-[3'-(4-methylpiperazin-1-yl)biphenyl-3-yl]pentanamide; 2-[3-(3-bromo-5-sulfamoylthien-2-yl)phenyl]-N-cyanomethyl-4-methylpentanamide; N-cyanomethyl-4-methyl-2-(4'-morpholin-4-ylcarbonylbiphenyl-3-yl)pentanamide; N-cyanomethyl-4-methyl-2-(4'-morpholin-4-ylsulfonylbiphenyl-3-yl)pentanamide; N-cyanomethyl-4- methyl-2-(3-morpholin-4-ylphenyl)pentanamide; N-cyanomethyl-4-methyl-2-(3'-methylsulfanylbiphenyl-3-yl)pentanamide; 1-biphenyl-3-yl-N-cyanomethylcyclohexanecarboxamide; 3-cyanomethyl-1-isobutyl-1-(3'-morpholin-4-ylbiphenyl-3-yl)urea; 1-biphenyl-3-yl-3-cyanomethyl-1-isobutylurea; N-(2-benzyloxy-1-cyanoethyl)-2-biphenyl-3-yl-4-methylpentanamide; 2-biphenyl-3-yl-N-(1-cyano-2-oxazol-2-ylethyl)-4-methylpentanamide; and N-(1-cyano-4-phenylbutyl)-2-biphenyl-3-yl-4-methylpentanamide.

Non-limiting examples of the instant invention include the following:

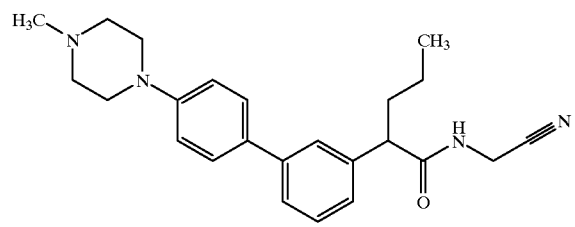

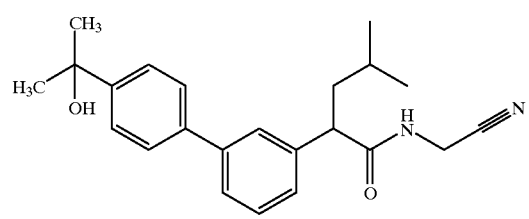

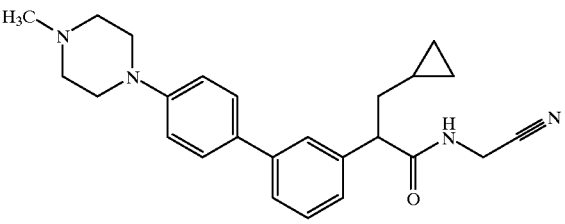

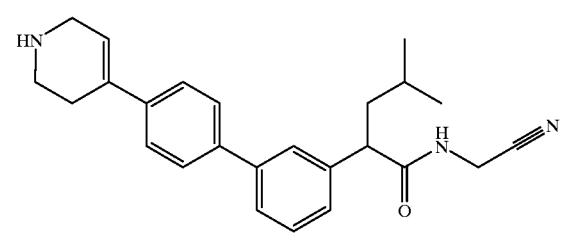

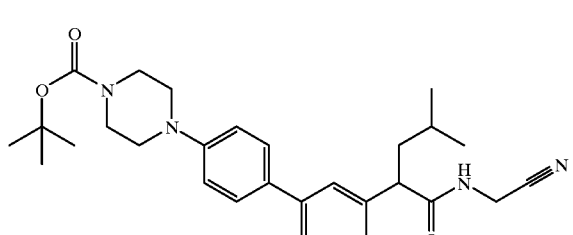

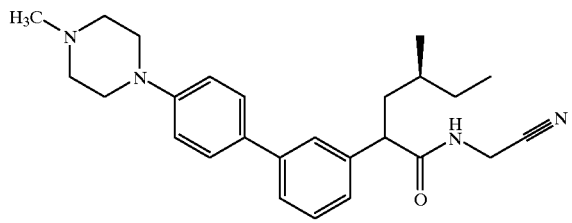

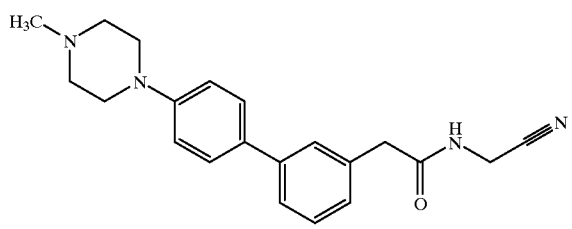

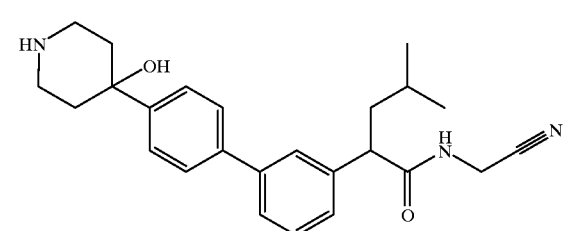

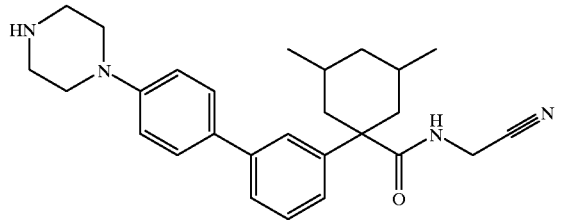

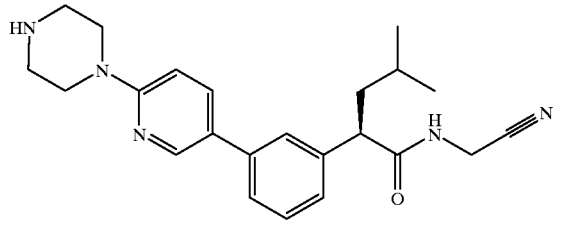

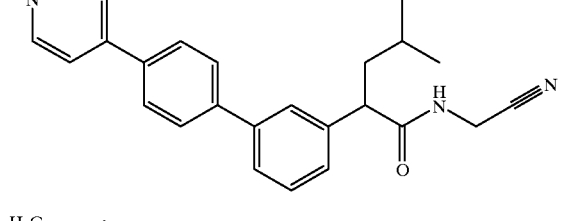

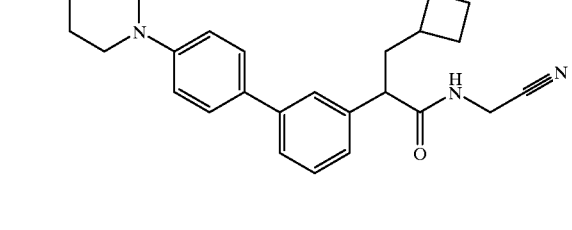

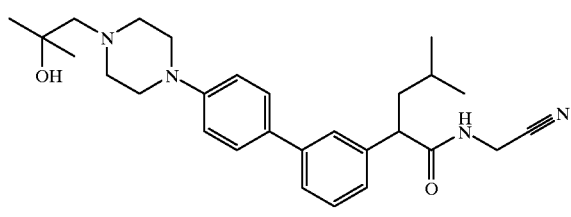
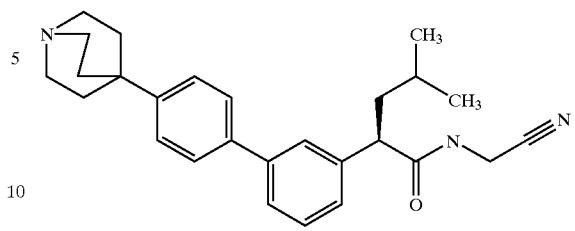
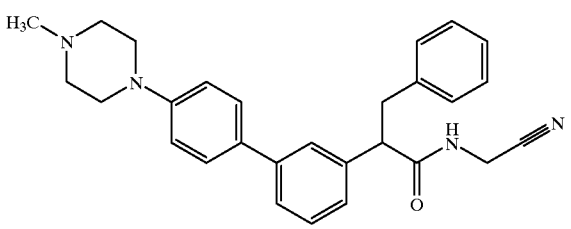
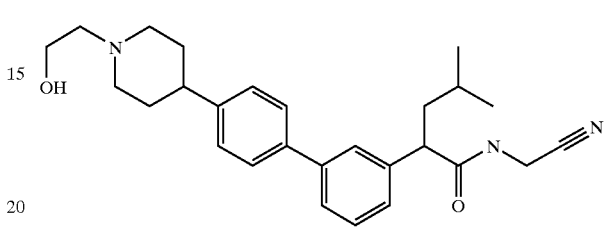
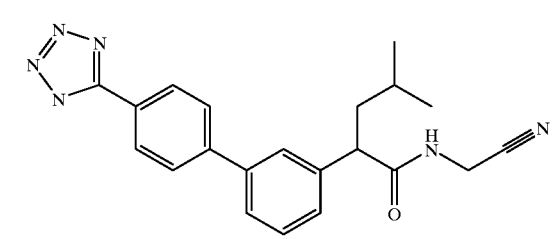
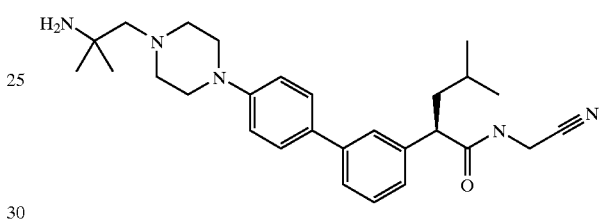
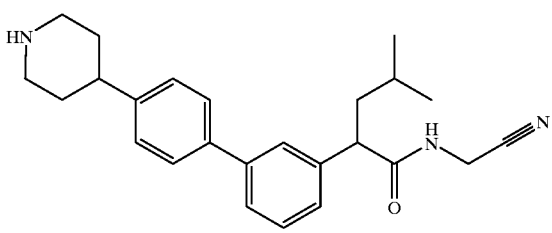
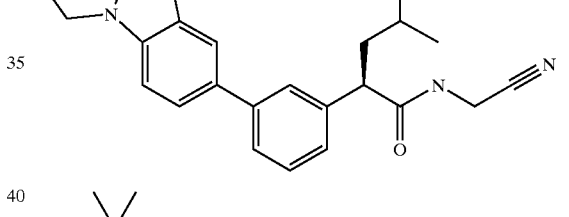
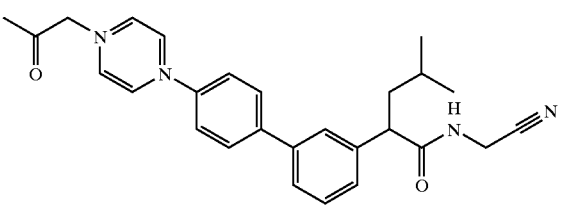
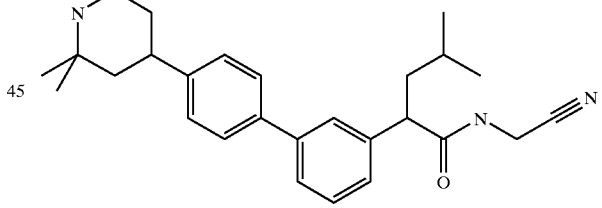
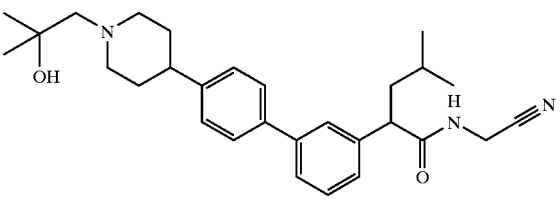
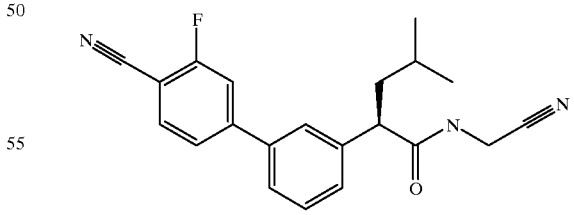
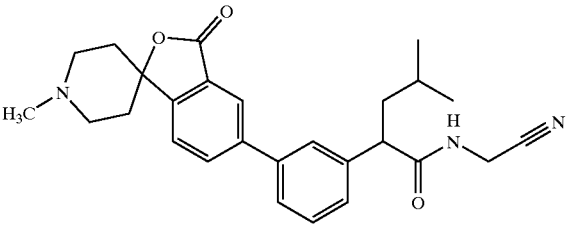
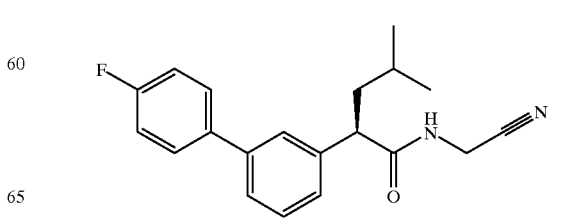

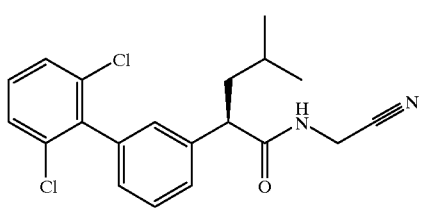
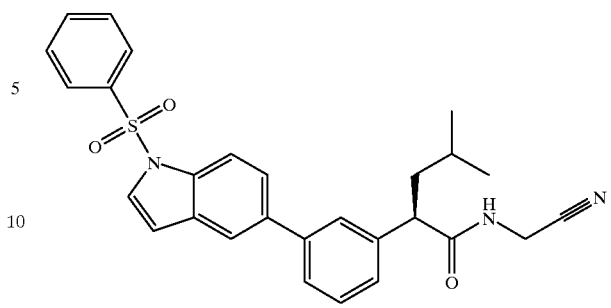
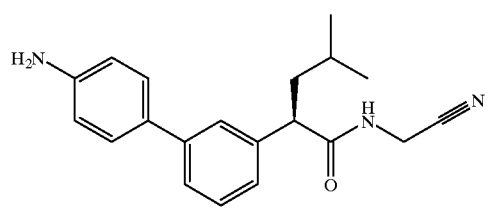
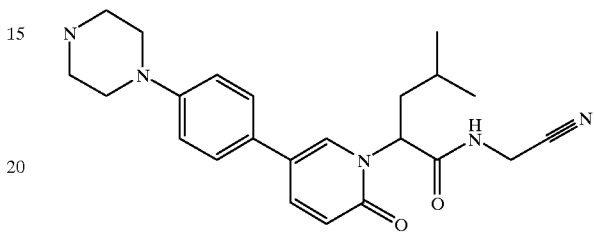
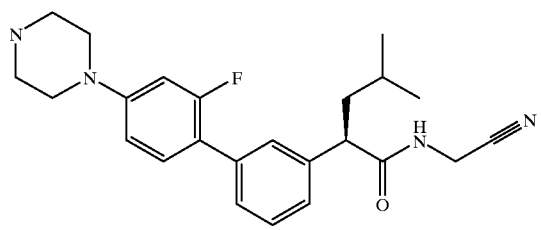
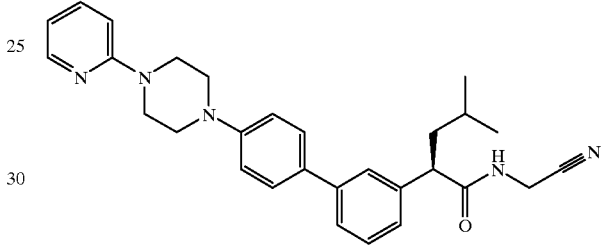
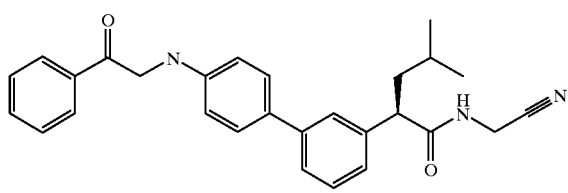
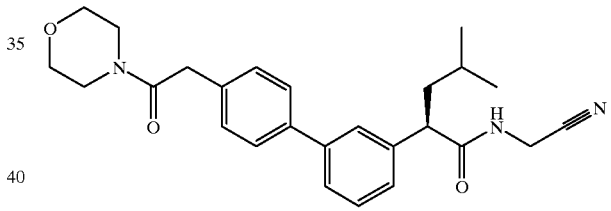
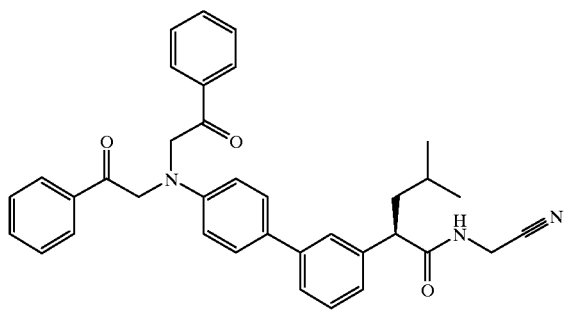
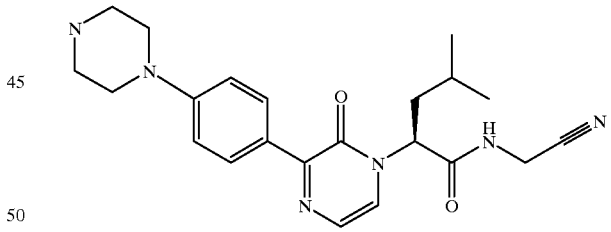
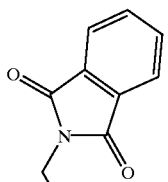
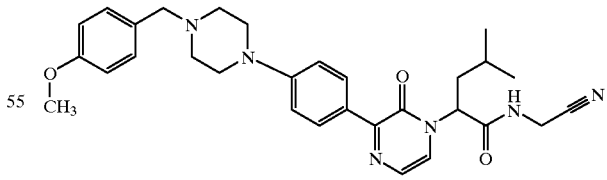
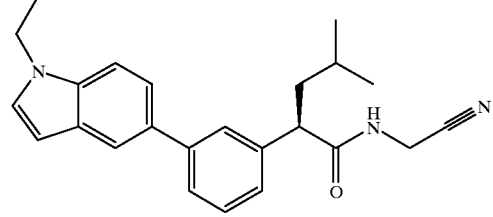
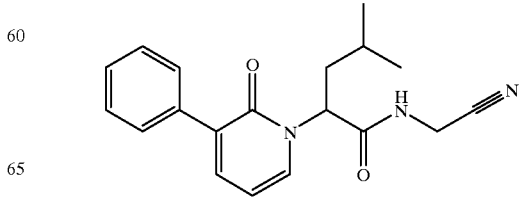

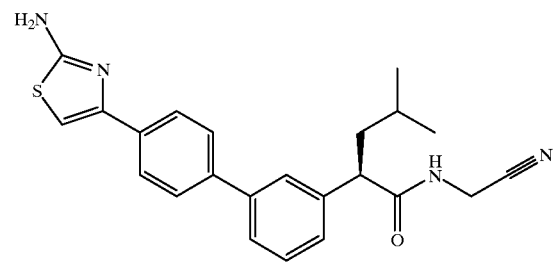
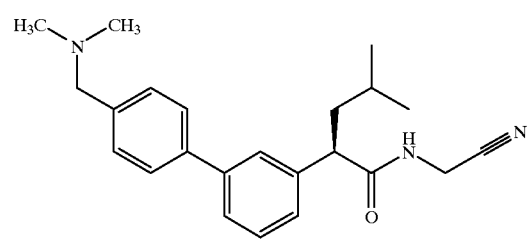
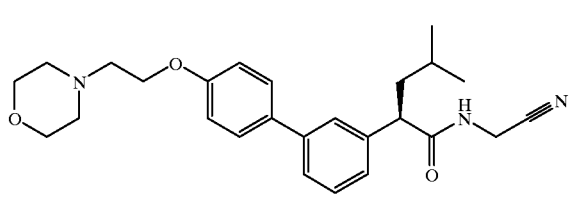
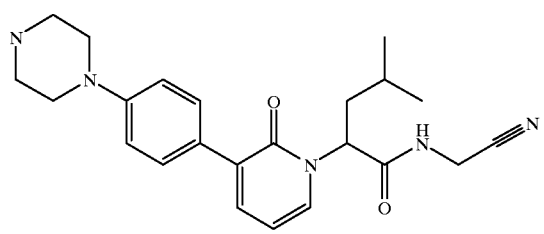
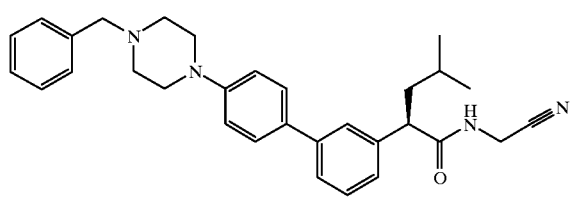
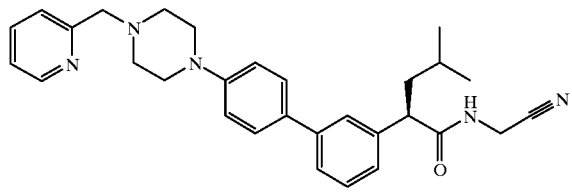
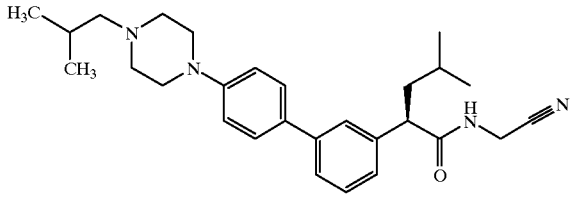
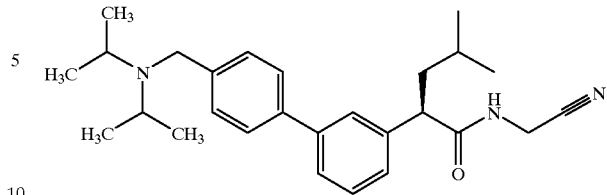
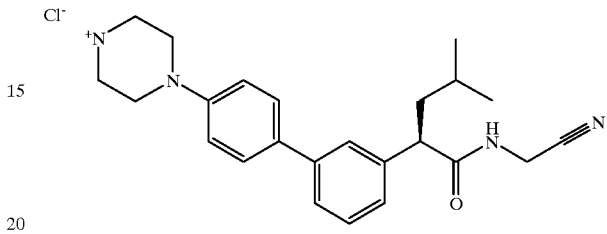
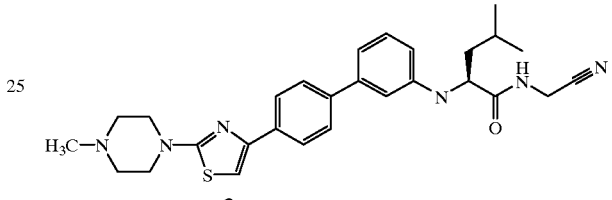
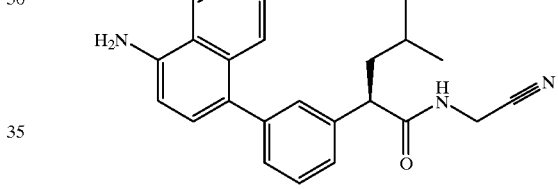
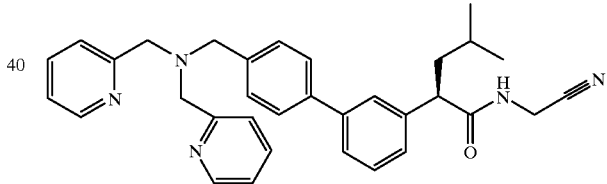
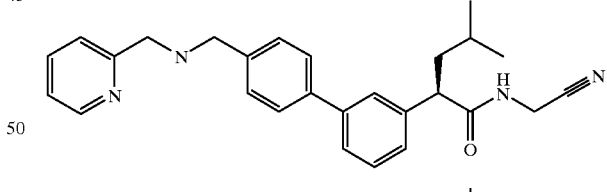
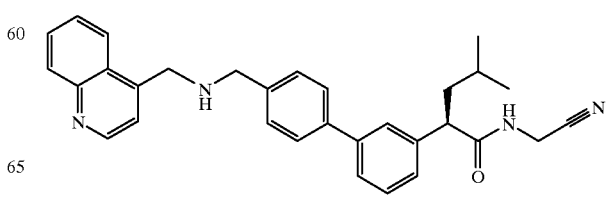

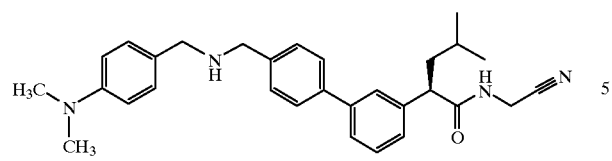
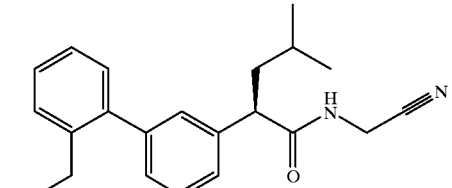
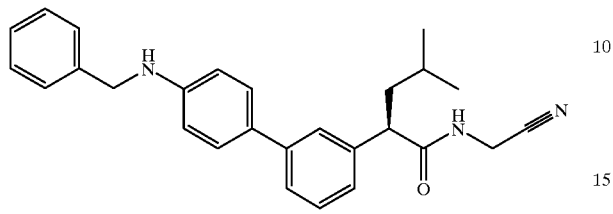
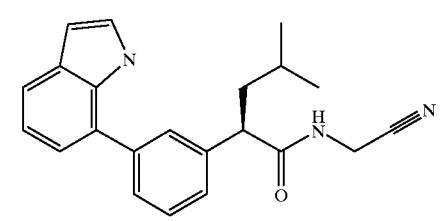
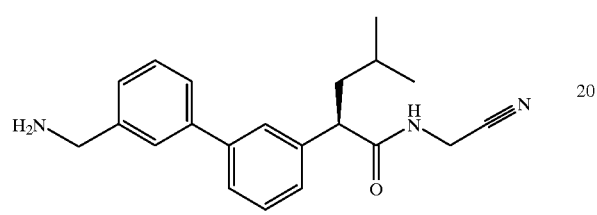
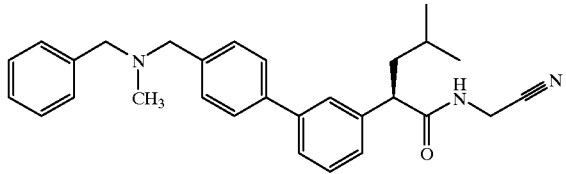
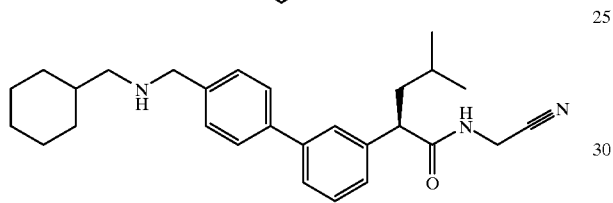
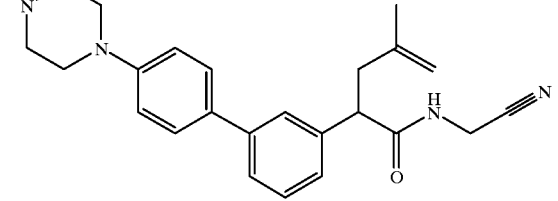
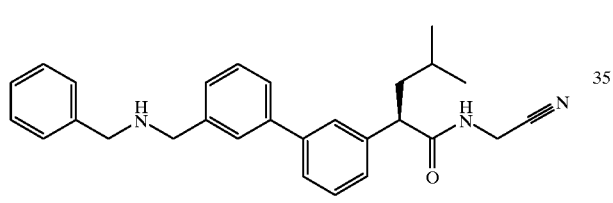
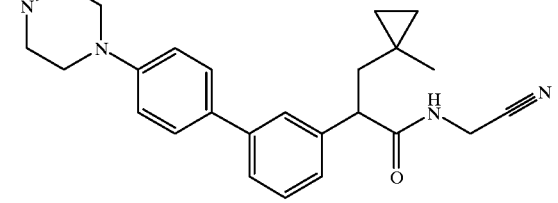
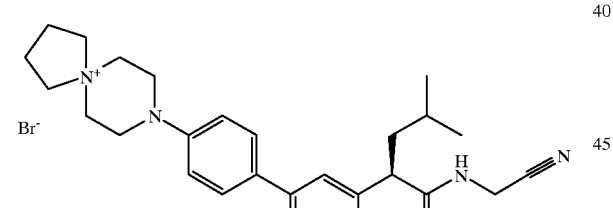
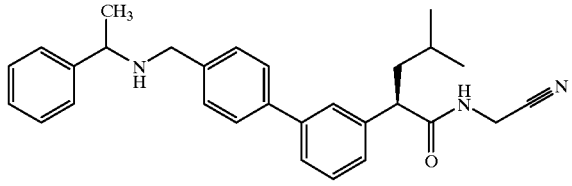
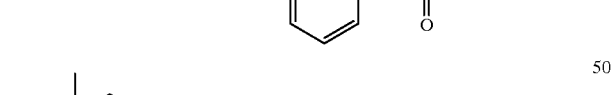
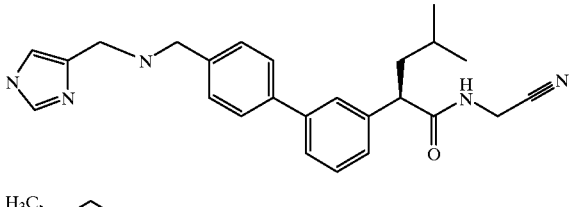
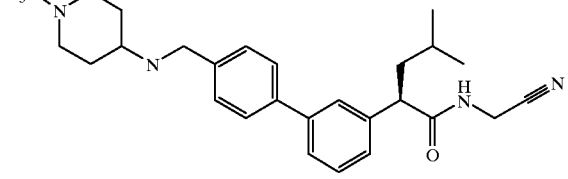
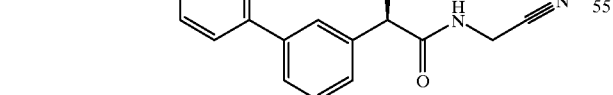
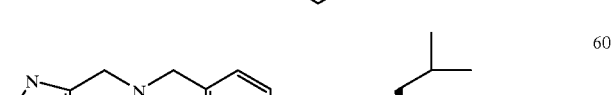
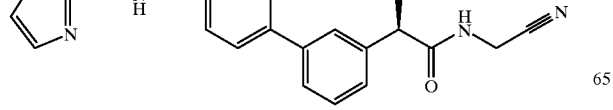

-continued

The following additional compounds of Formula I that can be prepared by the methods described in this Application.

Formula I

Table A lists the different A substituents:

A1, A2, A3, A4, A5, A6, A7, A8, A9, A10

-continued
Table A lists the different A substituents:
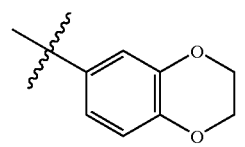 A11
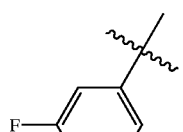 A12
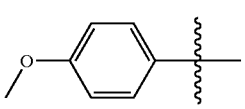 A13
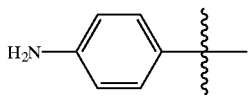 A14
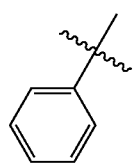 A15
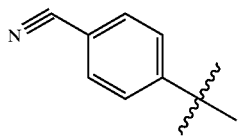 A16
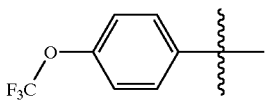 A17
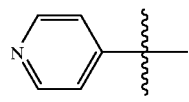 A18
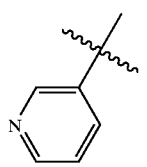 A19
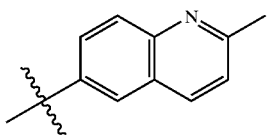 A20
-continued
Table A lists the different A substituents:
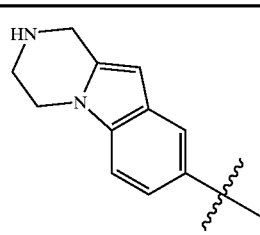 A21
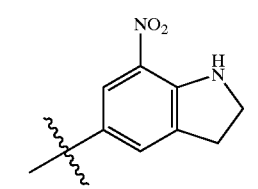 A22
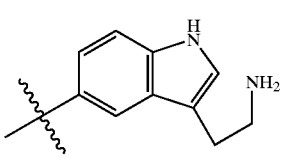 A23
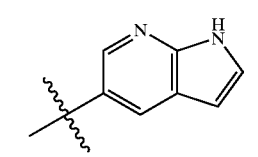 A24
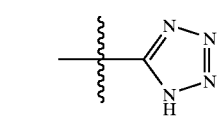 A25
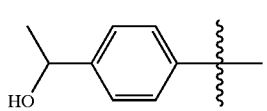 A26
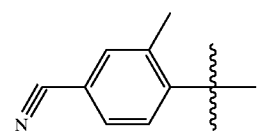 A27
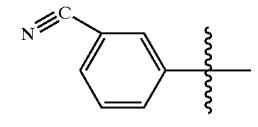 A28
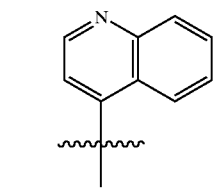 A29

-continued
Table A lists the different A substituents:
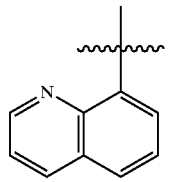 A30
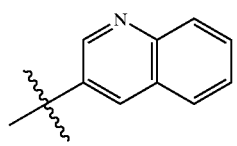 A31
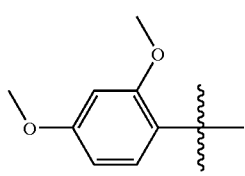 A32
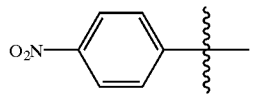 A33
The following additional compounds of Formula I that can be prepared by the methods described in this Application.
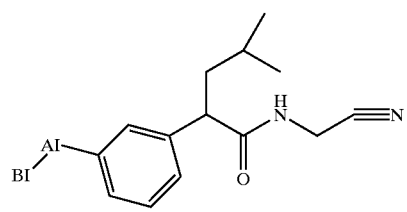
Table A lists the different A substituents:
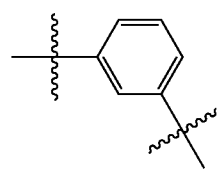 AI1
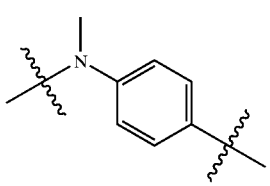 AI2
-continued
Table A lists the different A substituents:
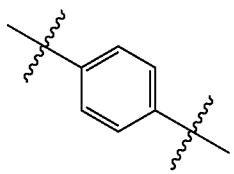 AI3
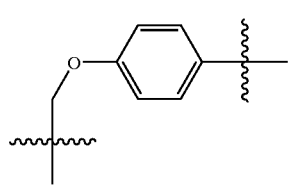 AI4
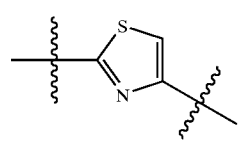 AI5
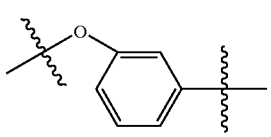 AI6
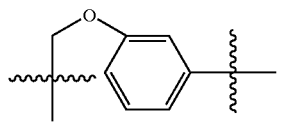 AI7
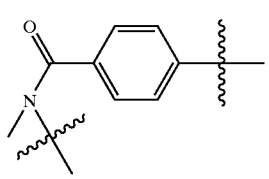 AI8
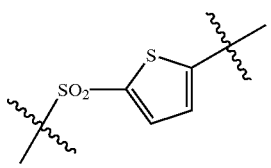 AI9
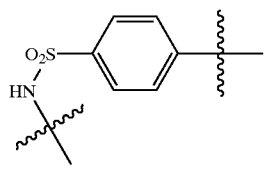 AI10
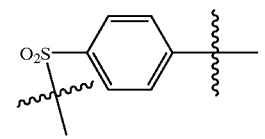 AI11

-continued

Table A lists the different A substituents:

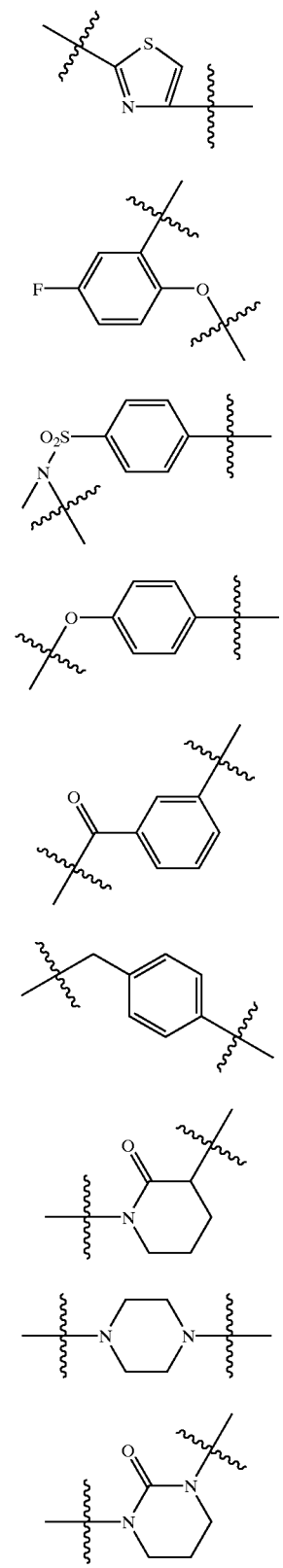

| | |
|---|---|
| AI12 | (thiazole structure) |
| AI13 | (fluoro-phenoxy structure) |
| AI14 | (sulfonamide-phenyl structure) |
| AI15 | (phenoxy structure) |
| AI16 | (benzoyl structure) |
| AI17 | (benzyl structure) |
| AI18 | (piperidinone structure) |
| AI19 | (piperazine structure) |
| AI20 | (cyclic urea structure) |

-continued

Table A lists the different A substituents:

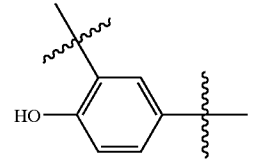

AI21

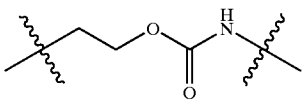

AI22

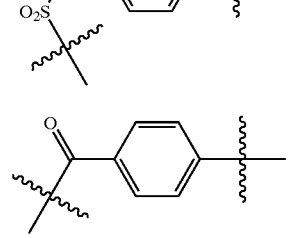

AI23

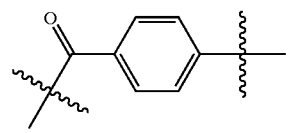

AI24

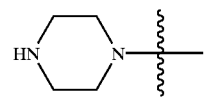

AI25

Table BI lists the different BI substituents:

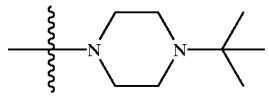

BI1

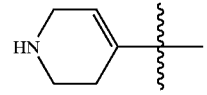

BI2

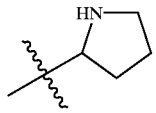

BI3

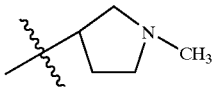

BI4

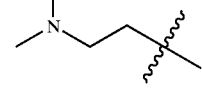

BI5

BI6

-continued
Table BI lists the different BI substituents:
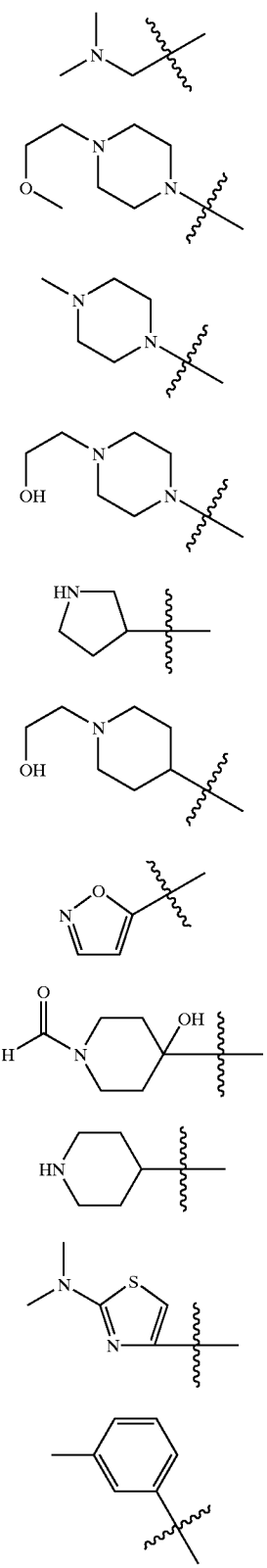
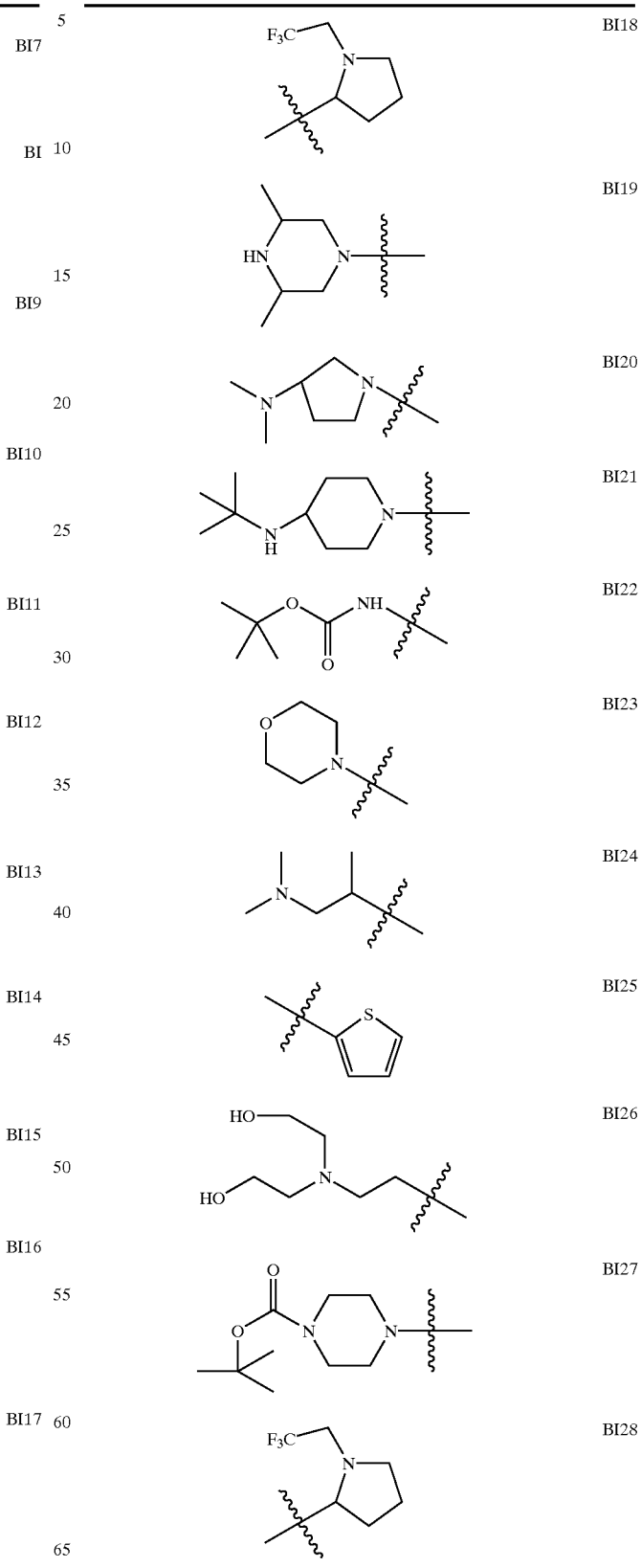

The following additional compounds of Formula I that can be prepared by the methods described in this Application.
Formula I
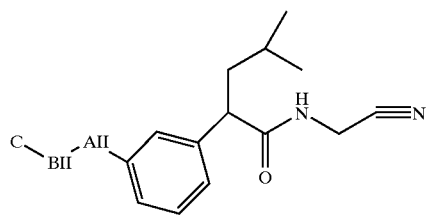
Table AII lists the different AII substituents:
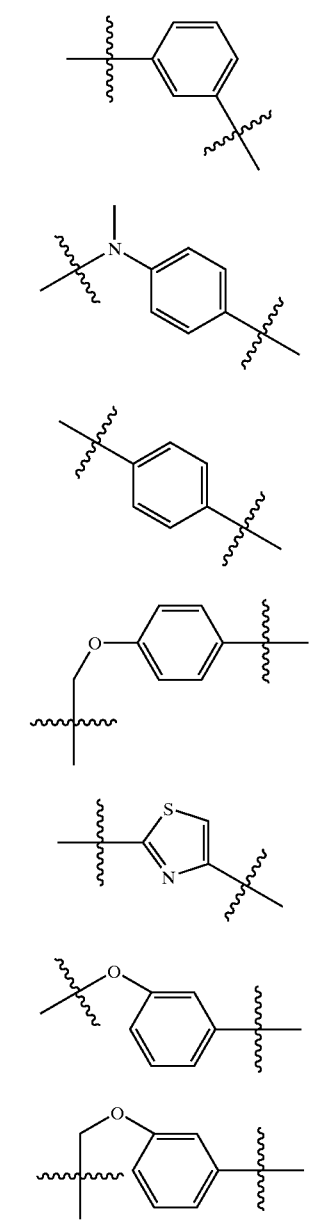
AII1
AII2
AI3
AII4
AII5
AI6
AII7
-continued
Table AII lists the different AII substituents:
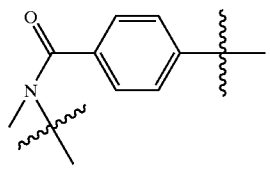
AII8
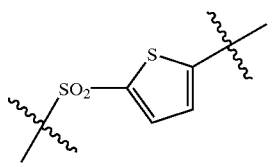
AI9
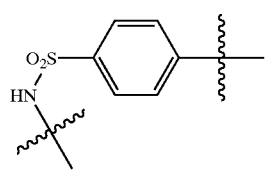
AII10
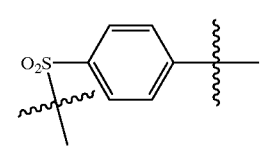
AII11
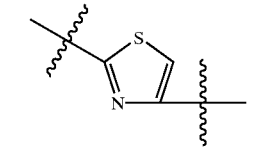
AI12
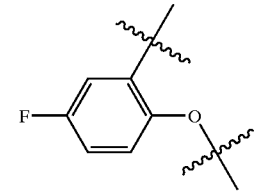
AII13
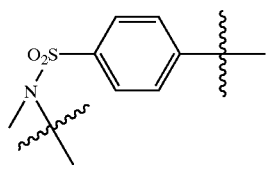
AII14
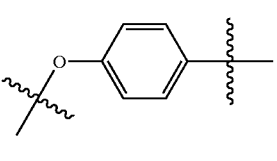
AI15
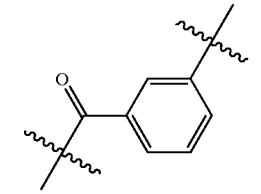
AII16

-continued
Table AII lists the different AII substituents:
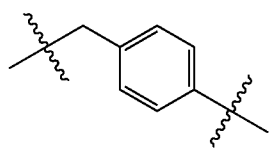 AII17
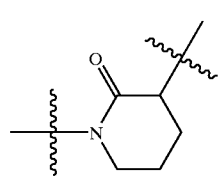 AI18
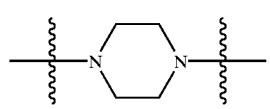 AII19
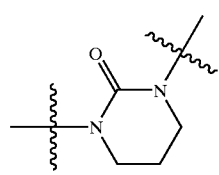 AII20
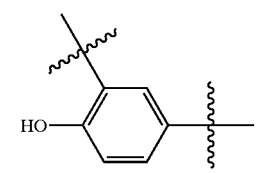 AI21
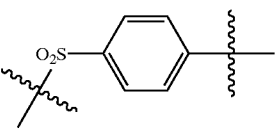 AII22
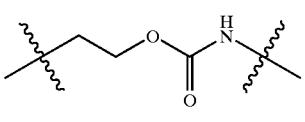 AII23
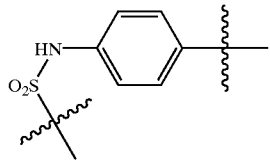 AI24
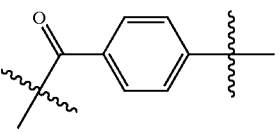 AII25
Table BII lists the different BII substituents:
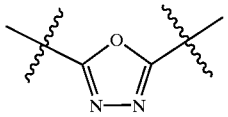 BII1
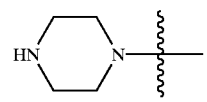 BII2
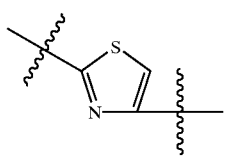 BII3
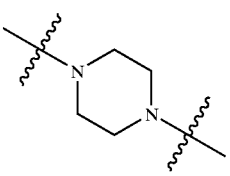 BII4
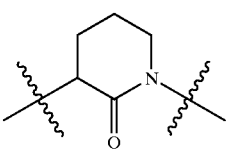 BII5
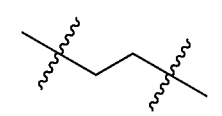 BII6
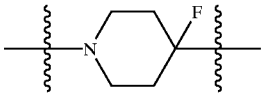 BII15
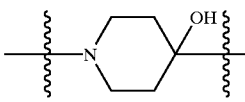 BII16
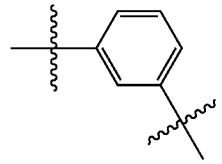 BII17
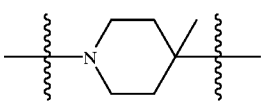 BII21

Table BII lists the different BII substituents:

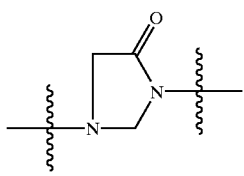
BII22

Table C lists different C substituents.

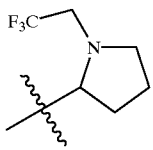
C1

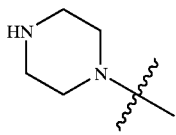
C2

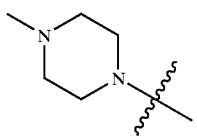
C3

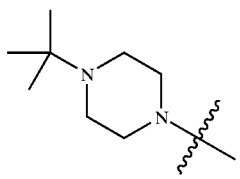
C4

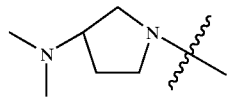
C5

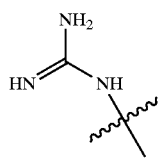
C6

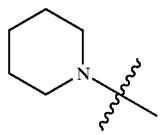
C7

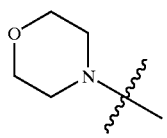
C8

Example 11
Cathepsin B Assay

Solutions of test compounds in varying concentrations were prepared in 10 μL of dimethyl sulfoxide (DMSO) and then diluted into assay buffer (40 μL, comprising: N,N-bis(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 Moles in 25 μL of assay buffer) was added to the dilutions. The assay solutions were mixed for 5–10 seconds on a shaker plate, covered and incubated for 30 minutes at room temperature. Z-FR-AMC (20 nMoles in 25 μL of assay buffer) was added to the assay solutions and hydrolysis was followed spectrophotometrically at (460 nm) for 5 minutes. Apparent inhibition constants ($K_i$) were calculated from the enzyme progress curves using standard mathematical models.

Compounds of the invention were tested by the above-described assay and observed to exhibit cathepsin B inhibitory activity.

Example 12
Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at room temperature. Z-Phe-Arg-AMC (4 nMoles in 25 μL of assay buffer) was added to the assay solutions and hydrolysis was followed spectrophotometrically at (460 nm) for 5 minutes. Apparent inhibition constants ($K_i$) were calculated from the enzyme progress curves using standard mathematical models.

Compounds of the invention were tested by the above-described assay and observed to exhibit cathepsin K inhibitory activity.

Example 13
Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at room temperature. Z-Phe-Arg-AMC (1 nMoles in 25 μL of assay buffer) was added to the assay solutions and hydrolysis was followed spectrophotometrically at (460 nm) for 5 minutes. Apparent inhibition constants ($K_i$) were calculated from the enzyme progress curves using standard mathematical models.

Compounds of the invention were tested by the above-described assay and observed to exhibit cathepsin L inhibitory activity.

Example 14
Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5–10 seconds on a shaker plate, covered and incubated for 30 minutes at room temperature. Z-Val-Val-Arg-AMC (9 nMoles in 25 µL of assay buffer) was added to the assay solutions and hydrolysis was followed spectrophotometrically at (460 nm) for 5 minutes. Apparent inhibition constants ($K_i$) were calculated from the enzyme progress curves using standard mathematical models.

Compounds of the invention were tested by the above-described assay and observed to exhibit cathepsin S inhibitory activity.

Example 15
Representative Pharmaceutical Formulations Containing a Compound of Formula I:

| ORAL FORMULATION | |
|---|---|
| Compound of Formula I | 10–100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of Formula I | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of Formula I | 1% |
| Microcrystalline Cellulose | 73% |
| Stearic Acid | 25% |
| Colloidal Silica | 1% |

The resulting tablets are useful for administration in accordance with the methods of this invention for treating or preventing a cathepsin mediated disease state, such as osteoporosis.

We claim:

1. The compound of formula I in which:

$X^1$ is —$CR^4R^5$— or —$CHR^7$—;

$R^4$ and $R^5$ along with the carbon atom to which they are attached represents wherein $R^{31}$ and $R^{32}$ independently represent hydrogen or hydroxy, alternatively $R^{31}$ and $R^{32}$ can be taken together to represent an oxo (═O) group;

$R^7$ is ($C_{4-8}$) branched alkyl or —$CH_2$-cyclopropyl;

$R^1$ is hydrogen;

$R^2$ is hydrogen or $R^{2a}$; alternatively, $R^1$ and $R^2$ together represent —$CH_2$—$CH_2$— or —$CH_2$—$NR^8$—$CH_2$—;

$R^{2a}$ represents ($C_{2-4}$) alkyl optionally substituted with a group selected from —$NR^8C(O)OR^{35}$, —$OR^{35}$, —$SR^{35}$, —$S(O)R^{35}$, —$S(O)_2R^{35}$, —$C(O)R^{35}$, —$SO_2NR^8R^{52}$ and —$OP(O)(OR^8)OR^{35}$;

$R^3$ is ($C_{6-10}$)aryl or hetero($C_{5-10}$)aryl, wherein $R^3$ may be substituted further by a radical selected from a group consisting of —$X^3NR^8R^{21}$, —$X^3NR^8C(O)R^{21}$, —$X^3NR^8C(O)OR^{21}$, —$X^3NR^8C(O)NR^8R^{21}$, —$X^3OR^{21}$, —$X^3SR^{21}$, —$X^3C(O)R^{21}$, —$X^3C(O)OR^{21}$, —$X^3OC(O)R^{21}$, —$X^3C(O)NR^8R^{21}$, —$X^3OR^{52}$, —$X^3CONR^8R^{52}$ and —$R^{21}$, wherein:

$X^3$ is a bond or ($C_{1-6}$)alkylene, $R^8$ at each occurrence independently is hydrogen or ($C_{1-6}$)alkyl and $R^{21}$ is ($C_{1-8}$)alkyl or —$X^3R^{22}$, wherein $X^3$ is as defined above;

$R^{22}$ is selected from a group consisting of hetero($C_{5-10}$)cycloalkyl, ($C_{6-10}$)aryl, hetero($C_{5-10}$)aryl and hetero($C_{8-10}$)bicycloaryl, wherein $R^{22}$ may be substituted further by a radical selected from a group consisting of ($C_{1-4}$)alkyl, —$X^3NR^8R^{23}$, —$X^3C(O)NR^8R^{52}$, —$X^3OR^{23}$, —$X^3NR^8C(O)R^{23}$, —$X^3SO_2NR^8R^{52}$, —$X^3C(O)NR^8R^{23}$, —$X^3SO_2NR^8R^{23}$, —$X^3COR^{23}$, —$X^3OR^{52}$, —$X^3S(O)_2R^{23}$, $X^3N(R^8)_2$ and —$R^{23}$, wherein $X^3$ is a bond or ($C_{1-6}$)alkylene, $R^{52}$ represents —$CH_2CH_2$—$N(CH_2CH_2OH)_2$, —$CH(CH_3)CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{23}$ is ($C_{1-8}$)alkyl or —$X^3R^{24}$, wherein $X^3$ is as defined above;

$R^{24}$ is selected from a group consisting of hetero($C_{5-10}$)cycloalkyl and hetero($C_{5-10}$)aryl, wherein $R^{24}$ may be substituted further with $R^{25}$, —$X^3OR^{52}$, —$X^3NR^8R^{25}$, —$X^3COOR^{25}$ and —$X^3SO_2NR^8R^{52}$; wherein $X^3$ is a bond or ($C_{1-6}$) alkylene, $R^{52}$ represents —$CH_2CH_2$—$N(CH_2CH_2OH)_2$, —$CH(CH_3)CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{25}$ is ($C_{1-8}$)alkyl or —$X^3R^{26}$, wherein $X^3$ is as defined above;

$R^{26}$ is hetero($C_{5-10}$)cycloalkyl; and wherein any of the ($C_{3-10}$)cycloalkyl, hetero($C_{5-10}$)cycloalkyl, ($C_{6-10}$)aryl, hetero($C_{5-10}$)aryl, ($C_{9-10}$)bicycloaryl and hetero($C_{8-10}$)bicycloaryl contained within $R^3$, $R^{22}$, $R^{24}$ and $R^{26}$ may be substituted further with up to five substituents selected from a group consisting of ($C_{1-6}$)alkyl, cyano, halo, nitro, halo-substituted ($C_{1-3}$)alkyl, —$X^3NR^{16}R^{16}$, —$X^3OR^{52}$ and —$X^3C(O)R^{16}$, wherein:

$X^3$ is a bond or ($C_{1-6}$)alkylene, $R^{52}$ represents —$CH_2CH_2$—$N(CH_2CH_2OH)_2$, —$CH(CH_3)CH_2N(CH_3)_2$, —$CH_2CH_2OH$, —$CH_2CH_2N(CH_3)_2$ or —$CH_2CN$, $R^{16}$ at each occurrence independently is selected from a group consisting of hydrogen, ($C_{1-3}$)alkyl or halo-substituted ($C_{1-3}$)alkyl and $R^{17}$ is —($C_{1-3}$)alkyl or halo-substituted ($C_{1-3}$)alkyl; and the N-oxide compounds, prodrug derivatives, protected derivatives, individual stereo isomers and mixtures of stereo isomers, or pharmaceutically acceptable salts thereof, with the proviso that only one of $R^3$, $R^{22}$, $R^{24}$ and $R^{26}$ represents a fused bicyclic ring structure.

2. A compound of claim 1 wherein:

$X^1$ is —$CHR^7$—;

$R^7$ is i-propyl;

$R^2$ is hydrogen or $R^{2a}$;

$R^{2a}$ represents ($C_4$) alkyl optionally substituted with a group selected from —$NR^8C(O)OR^{35}$ or —$SR^{35}$;

R³ is phenyl or hetero($C_{5-6}$)aryl, wherein R³ may be substituted further by a radical selected from a group consisting of —$X^3NR^8R^{21}$, —$X^3NR^8C(O)R^{21}$, —$X^3NR^8C(O)OR^{21}$ and —$R^{21}$;

$R^{21}$ is —$X^3R^{22}$;

$R^{22}$ is selected from a group consisting of hetero($C_{5-6}$)cycloalkyl, ($C_6$)aryl, hetero($C_{5-10}$)aryl and hetero($C_{8-9}$)bicycloaryl, wherein $R^{22}$ can be optionally substituted further by a radical selected from a group consisting of ($C_{1-4}$)alkyl, —$X^3OR^{23}$, —$X^3NR^8R^{23}$, —$X^3C(O)NR^8R^{23}$, —$X^3C(O)NR^8R^{52}$, —$X^3SO_2NR^8R^{23}$ and $R^{23}$; wherein $X^3$ is a bond or ($C_{1-6}$)alkylene, $R^{52}$ represents —$CH_2CH_2$—$N(CH_2CH_2OH)_2$, —CH($CH_3$)$CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{23}$ is ($C_{1-8}$)alkyl or —$X^3R^{24}$, wherein $X^3$ is as defined above;

$R^{24}$ is selected from a group consisting of hetero($C_{5-6}$)cycloalkyl and hetero($C_{5-6}$)aryl, wherein $R^{24}$ may be substituted further with $R^{25}$, —$X^3OR^{52}$, —$X^3NR^8R^{25}$, —$X^3COOR^{25}$ and —$X^3SO_2NR^8R^{52}$; wherein $X^3$ is a bond or ($C_{1-6}$)alkylene, $R^{52}$ represents —$CH_2CH_2$—N($CH_2CH_2OH)_2$, —CH($CH_3$)$CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{25}$ is ($C_{1-4}$)alkyl or —$X^3R^{26}$, wherein $X^3$ is as defined above;

$R^{26}$ is hetero($C_{5-10}$)cycloalkyl; and wherein the ($C_{3-10}$)cycloalkyl contained within $R^{26}$ may be substituted further with up to three groups selected from a group consisting of ($C_{1-2}$)alkyl.

3. A compound of claim 2 wherein:

$R^2$ is hydrogen;

$R^3$ is phenyl or hetero($C_{5-6}$)aryl, wherein $R^3$ is substituted by —$R^{21}$;

$R^{21}$ is —$X^3R^{22}$;

$X^3$ is a bond;

$R^{22}$ is hetero($C_6$)aryl and hetero($C_{5-6}$)aryl; wherein $R^{22}$ is substituted further by $R^{23}$;

$R^{23}$ is —$X^3R^{24}$, wherein $X^3$ is a bond;

$R^{24}$ is hetero($C_{5-6}$)aryl, wherein $R^{24}$ may be substituted further with $R^{25}$, —$X^3OR^{52}$, —$X^3NR^8R^{25}$, —$X^3COOR^{25}$ or —$X^3SO_2NR^8R^{52}$; wherein $X^3$ is a bond or ($C_{1-6}$)alkylene, $R^{52}$ represents —$CH_2CH_2$—N($CH_2CH_2OH)_2$, —CH($CH_3$)$CH_2N(CH_3)_2$, —$CH_2CH_2OH$, —$CH_2CN$ or —$CH_2CH_2N(CH_3)_2$, $R^8$ at each occurrence independently is hydrogen or ($C_{1-6}$)alkyl and $R^{25}$ is —$X^3R^{26}$, wherein $X^3$ is a bond; and $R^{26}$ is hetero($C_{5-6}$)cycloalkyl substituted with up to two (0–2) groups selected from a group consisting of ($C_{1-2}$)alkyl.

4. A compound of formula I

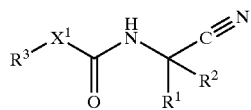

wherein:

$X^1$ is selected from a group consisting of —$CR^4R^5$—, —$CR^6R^7$— and —$NR^7$—, wherein:

$R^4$ and $R^5$ along with the carbon atom to which they are attached represents

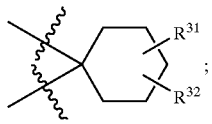

where $R^{31}$ and $R^{32}$ independently represent hydrogen or hydroxy, alternatively $R^{31}$ and $R^{32}$ can be taken together to represent an oxo (=O) group;

$R^6$ is hydrogen or ($C_{1-6}$)alkyl; and $R^7$ is ($C_{1-8}$)alkyl or ($CH_2$)$_{1-3}$ cyclopropyl;

$R^1$ and $R^2$ is hydrogen;

$R^3$ is phenyl or hetero($C_{5-6}$)aryl, wherein $R^3$ is substituted by —$R^{21}$;

$R^{21}$ is —$X^3R^{22}$;

—$X^3$ is a bond;

$R^{22}$ is hetero($C_{5-6}$)aryl; wherein $R^{22}$ is substituted by —$R^{23}$;

$R^{23}$ is —$X^3R^{24}$, wherein $X^3$ is a bond;

$R^{24}$ is hetero($C_{5-6}$)aryl substituted by $R^{25}$;

$R^{25}$ is —$X^3R^{26}$, wherein $X^3$ is a bond; and $R^{26}$ is hetero($C_{5-6}$)cycloalkyl substituted with up to two (0–2) groups selected from a group consisting of ($C_{1-2}$)alkyl.

5. A compound selected from:

4-Methyl-2-[3'-(2-piperazin-1-yl-thiazol-4-yl)-biphenyl-3-yl]-pentanoic acid cyanomethyl-amide;

4-Methyl-2-{3'-[2-(4-methyl-piperazin-1-yl)-thiazol-4-yl]-biphenyl-3-yl}-pentanoic acid cyanomethyl-amide;

2-{3'-[2-(4-tert-Butyl-piperazin-1-yl)-thiazol-4-yl]-biphenyl-3-yl}-4-methyl-pentanoic acid cyanomethyl-amide;

2-{3'-[2-(3-Dimethylamino-pyrrolidin-1-yl)-thiazol-4-yl]-biphenyl-3-yl}-4-methyl-pentanoic acid cyanomethyl-amide;

4-Methyl-2-[4'-(2-piperazin-1-yl-thiazol-4-yl)-biphenyl-3-yl]-pentanoic acid cyanomethyl-amide;

4-Methyl-2-{4'-[2-(4-methyl-piperazin-1-yl)-thiazol-4-yl]-biphenyl-3-yl}-pentanoic acid cyanomethyl-amide;

4-Methyl-2-{3'-[2-(4-methyl-piperazin-1-yl)-thiazol-4-yl]-biphenyl-3-yl}-pentanoic acid (1-cyano-cyclopropyl)-amide;

4-Methyl-2-[3'-(2-piperazin-1-ylmethyl-thiazol-4-yl)-biphenyl-3-yl]-pentanoic acid cyanomethyl-amide;

4-Methyl-2-{4'-[2-(4-methyl-piperazin-1-yl)-thiazol-4-yl]-biphenyl-3-yl}-pentanoic acid (1-cyano-cyclopropyl)-amide;

4-Methyl-2-{3'-[2-(4-methyl-piperazin-1-yl)-thiazol-4-yl]-biphenyl-3-yl}-pentanoic acid cyanomethyl-amide;

4-Methyl-2-{3'-[2-(4-methyl-piperazin-1-yl)-thiazol-4-yl]-biphenyl-3-yl}-pentanoic acid cyanomethyl-amide;

2-{3'-[2-(4-tert-Butyl-piperazin-1-yl)-thiazol-4-yl]-biphenyl-3-yl}-4-methyl-pentanoic acid cyanomethyl-amide;

4-Methyl-2-[4'-(2-piperazin-1-yl-thiazol-4-yl)-biphenyl-3-yl]-pentanoic acid (1-cyano-cyclopropyl)-amide;

4-Methyl-2-{4'-[2-(4-methyl-piperazin-1-yl)-thiazol-4-yl]-biphenyl-3-yl}-pentanoic acid (1-cyano-cyclopropyl)-amide;

4-Methyl-2-(4'-piperazin-1-yl-biphenyl-3-yl)-pentanoic acid (1-cyano-cyclopropyl)-amide;

4-Methyl-2-[3'-(pyrrolidin-2-ylmethoxy)-biphenyl-3-yl]-pentanoic acid cyanomethyl-amide;

2-[4'-(4-tert-Butyl-piperazin-1-yl)-biphenyl-3-yl]-4-methyl-pentanoic acid cyanomethyl-amide;

4-Methyl-2-(4'-piperazin-1-yl-biphenyl-3-yl)-pentanoic acid cyanomethyl-amide;

4-Methyl-2-[4'-(1,2,3,6-tetrahydro-pyridin-4-yl)-biphenyl-3-yl]-pentanoic acid cyanomethyl-amide;
4-Methyl-2-[4'-(4-methyl-piperazin-1-yl)-biphenyl-3-yl]-pentanoic acid cyanomethyl-amide;
2-[4'-(4-tert-Butyl-piperazin-1-yl)-biphenyl-3-yl]-4-methyl-pentanoic acid (1-cyano-cyclopropyl)-amide;
4-Methyl-2-{4'-[methyl-(1-methyl-pyrrolidin-3-yl)-amino]-biphenyl-3-yl}-pentanoic acid cyanomethyl-amide;
4-Methyl-2-[3'-(pyrrolidin-2-ylmethoxy)-biphenyl-3-yl]-pentanoic acid cyanomethyl-amide;
4-Methyl-2-[4'-(pyrrolidin-2-ylmethoxy)-biphenyl-3-yl]-pentanoic acid cyanomethyl-amide;
4-Methyl-2-[4'-(pyrrolidin-2-ylmethoxy)-biphenyl-3-yl]-pentanoic acid cyanomethyl-amide;
4-Methyl-2-[3'-(1-methyl-pyrrolidin-3-ylmethyl)-biphenyl-3-yl]-pentanoic acid cyanomethyl-amide;
2-{4'-[4-(2-Hydroxy-ethyl)-piperazin-1-yl]-biphenyl-3-yl}-4-methyl-pentanoic acid (1-cyano-cyclopropyl)-amide;
3'-[1-(Cyanomethyl-carbamoyl)-3-methyl-butyl]-biphenyl-4-carboxylic acid methyl-(1-methyl-pyrrolidin-3-yl)-amide;
4-Methyl-2-[3'-(pyrrolidin-3-yloxy)-biphenyl-3-yl]-pentanoic acid cyanomethyl-amide;
4-Methyl-2-(4'-piperazin-1-yl-biphenyl-3-yl)-pentanoic acid cyanomethyl-amide;
3'-[1-(Cyanomethyl-carbamoyl)-3-methyl-butyl]-biphenyl-4-carboxylic acid (2-dimethylamino-ethyl)-amide;
4-Methyl-2-[3'-(pyrrolidin-3-yloxy)-biphenyl-3-yl]-pentanoic acid cyanomethyl-amide;
4-Methyl-2-[3-(7-nitro-1H-indol-4-yl)-phenyl]-pentanoic acid cyanomethyl-amide;
4-Methyl-2-[3'-(pyrrolidin-3-yloxy)-biphenyl-3-yl]-pentanoic acid cyanomethyl-amide;
3'-[1-(Cyanomethyl-carbamoyl)-3-methyl-butyl]-biphenyl-4-carboxylic acid (2-morpholin-4-yl-ethyl)-amide;
2-{3'-[1-(2-Hydroxy-ethyl)-piperidin-4-ylmethyl]-biphenyl-3-yl}-4-methyl-pentanoic acid cyanomethyl-amide;
2-(3-{5-[4-(2-Hydroxy-ethyl)-piperazine-1-sulfonyl]-thiophen-2-yl}-phenyl)-4-methyl-pentanoic acid cyanomethyl-amide;
4-Methyl-2-{3-[2-(4-methyl-piperazin-1-yl)-thiazol-5-yl]-phenyl}-pentanoic acid cyanomethyl-amide;
3'-[1-(Cyanomethyl-carbamoyl)-3-methyl-butyl]-biphenyl-4-carboxylic acid (2-dimethylamino-ethyl)-methyl-amide;
4-Methyl-2-[4'-(piperidin-4-yloxy)-biphenyl-3-yl]-pentanoic acid cyanomethyl-amide;
4-Methyl-2-{3-[5-(4-methyl-piperazine-1-sulfonyl)-thiophen-2-yl]-phenyl}-pentanoic acid cyanomethyl-amide;
2-{3-[3-(2-Amino-ethyl)-1H-indol-5-yl]-phenyl}-4-methyl-pentanoic acid cyanomethyl-amide;
4-Methyl-2-[4'-(pyrrolidin-3-yloxy)-biphenyl-3-yl]-pentanoic acid cyanomethyl-amide; and
2-[3'-(2-Dimethylamino-thiazol-4-yl)-biphenyl-3-yl]-4-methyl-pentanoic acid cyanomethyl-amide.

6. A compound selected from:
4-Methyl-2-[3'-(2-piperazin-1-yl-thiazol-4-yl)-biphenyl-3-yl]-pentanoic acid cyanomethyl-amide;
2-(4'-Hydroxy-3'-isoxazol-5-yl-biphenyl-3-yl)-4-methyl-pentanoic acid cyanomethyl-amide;
2-[4'-(2-Dimethylamino-thiazol-4-yl)-biphenyl-3-yl]-4-methyl-pentanoic acid cyanomethyl-amide;
2-[3'-(2-Guanidino-thiazol-4-yl)-biphenyl-3-yl]-4-methyl-pentanoic acid cyanomethyl-amide;
4-Methyl-2-{3-[5-(4-methyl-piperazine-1-sulfonyl)-thiophen-2-yl]-phenyl}-pentanoic acid cyanomethyl-amide;
4-Methyl-2-{3-[2-(4-methyl-piperazin-1-yl)-thiazol-4-yl]-phenyl}-pentanoic acid cyanomethyl-amide;
2-{3-[2-(3,5-Dimethyl-piperazin-1-yl)-thiazol-4-yl]-phenyl}-4-methyl-pentanoic acid cyanomethyl-amide;
4-Methyl-2-{3-[2-(4-methyl-piperazin-1-yl)-thiazol-5-yl]-phenyl}-pentanoic acid cyanomethyl-amide;
4-Methyl-2-[2-(4-piperazin-1-yl-phenyl)-thiazol-4-yl]-pentanoic acid cyanomethyl-amide;
4-Methyl-2-{3'-[2-(4-methyl-piperazin-1-yl)-thiazol-4-yl]-biphenyl-3-yl}-pentanoic acid cyanomethyl-amide;
4-Methyl-2-{4'-[2-(4-methyl-piperazin-1-yl)-thiazol-4-yl]-biphenyl-3-yl}-pentanoic acid cyanomethyl-amide;
4-Methyl-2-[3'-(pyrrolidin-3-yloxy)-biphenyl-3-yl]-pentanoic acid cyanomethyl-amide;
2-{3'-[1-(2-Hydroxy-ethyl)-piperidin-4-yloxy]-biphenyl-3-yl}-4-methyl-pentanoic acid cyanomethyl-amide;
4-Methyl-2-[3'-(piperidin-4-yloxy)-biphenyl-3-yl]-pentanoic acid cyanomethyl-amide;
4-Methyl-2-[4'-(piperidin-4-yloxy)-biphenyl-3-yl]-pentanoic acid cyanomethyl-amide;
2-{4'-[1-(2-Hydroxy-ethyl)-piperidin-4-yloxy]-biphenyl-3-yl}-4-methyl-pentanoic acid cyanomethyl-amide;
4-Methyl-2-[4'-(pyrrolidin-3-yloxy)-biphenyl-3-yl]-pentanoic acid cyanomethyl-amide;
2-[3'-(2-Dimethylamino-ethoxy)-biphenyl-3-yl]-4-methyl-pentanoic acid cyanomethyl-amide;
4-{3'-[1-(Cyanomethyl-carbamoyl)-3-methyl-butyl]-biphenyl-4-yloxy}-piperidine-1-carboxylic acid tert-butyl ester;
4-{3'-[1-(Cyanomethyl-carbamoyl)-3-methyl-butyl]-biphenyl-3-yloxy}-piperidine-1-carboxylic acid tert-butyl ester;
3-{3'-[1-(Cyanomethyl-carbamoyl)-3-methyl-butyl]-biphenyl-3-yloxy}-pyrrolidine-1-carboxylic acid tert-butyl ester;
3-{3'-[1-(Cyanomethyl-carbamoyl)-3-methyl-butyl]-biphenyl-4-yloxy}-pyrrolidine-1-carboxylic acid tert-butyl ester;
2-[5'-Fluoro-2'-(pyrrolidin-3-yloxy)-biphenyl-3-yl]-4-methyl-pentanoic acid cyanomethyl-amide;
3-{3'-[1-(Cyanomethyl-carbamoyl)-3-methyl-butyl]-biphenyl-3-yloxy}-pyrrolidine-1-carboxylic acid tert-butyl ester;
4-Methyl-2-[3'-(pyrrolidin-3-yloxy)-biphenyl-3-yl]-pentanoic acid cyanomethyl-amide;
4-Methyl-2-[3-(2-piperazin-1-ylmethyl-thiazol-4-yl)-phenyl]-pentanoic acid cyanomethyl-amide;
4-(4-{3-[1-(Cyanomethyl-carbamoyl)-3-methyl-butyl]-phenyl}-thiazol-2-ylmethyl)-piperazine-1-carboxylic acid tert-butyl ester;
3-{3'-[1-(Cyanomethyl-carbamoyl)-3-methyl-butyl]-5-fluoro-biphenyl-2-yloxy}-pyrrolidine-1-carboxylic acid tert-butyl ester;
4-Methyl-2-[3'-(pyrrolidin-3-yloxy)-biphenyl-3-yl]-pentanoic acid cyanomethyl-amide;
2-(3-Isoquinolin-4-yl-phenyl)-4-methyl-pentanoic acid cyanomethyl-amide;
4-Methyl-2-[4'-(toluene-3-sulfonylamino)-biphenyl-3-yl]-pentanoic acid cyanomethyl-amide;
4-Methyl-2-(4'-nitro-biphenyl-3-yl)-pentanoic acid cyanomethyl-amide;
2-(2',4'-Dimethoxy-biphenyl-3-yl)-4-methyl-pentanoic acid cyanomethyl-amide;
2-(4'-Methoxy-biphenyl-3-yl)-4-methyl-pentanoic acid cyanomethyl-amide;
2-(4'-Amino-biphenyl-3-yl)-4-methyl-pentanoic acid cyanomethyl-amide;

2-(3'-Amino-biphenyl-3-yl)-4-methyl-pentanoic acid cyanomethyl-amide;
4-Methyl-2-(3'-nitro-biphenyl-3-yl)-pentanoic acid cyanomethyl-amide;
4-Methyl-2-(4'-sulfamoyl-biphenyl-3-yl)-pentanoic acid cyanomethyl-amide;
2-(5'-Acetyl-2'-morpholin-4-yl-biphenyl-3-yl)-4-methyl-pentanoic acid cyanomethyl-amide;
N-(cyanomethyl)-4-methyl-2-[3-(2-methyl-6-quinolinyl)phenyl]pentanamide;
N-(cyanomethyl)-4-methyl-2-[3-(3-quinolinyl)phenyl]pentanamide;
N-(cyanomethyl)-2-[3-(1H-indol-5-yl)phenyl]-4-methylpentanamide;
4-[(tert-butoxycarbonyl)amino]-3'-(1-{[(cyanomethyl)amino]carbonyl}-3-methylbutyl)-1,1'-biphenyl;
4-{[(tert-butoxycarbonyl)amino]methyl}-3'-(1-{[(cyanomethyl)amino]carbonyl}-3-methylbutyl)-1,1'-biphenyl;
2-[4'-(aminomethyl)[1,1'-biphenyl]-3-yl]-N-(cyanomethyl)-4-methylpentanamide;
N-(cyanomethyl)-4-methyl-2-[3-(1-methyl-1H-indol-5-yl)phenyl]pentanamide;
2-[3-(7-nitro-1H-indol-5-yl)phenyl]-N-(cyanomethyl)-4-methylpentanamide;
N-(cyanomethyl)-4-methyl-2-[3-(7-nitro-2,3-dihydro-1H-indol-5-yl)phenyl]pentanamide;
2-[3-(7-amino-1H-indol-5-yl)phenyl]-N-(cyanomethyl)-4-methylpentanamide;
N-(cyanomethyl)-2-(3-{3-[(dimethylamino)methyl]-1H-indol-5-yl}phenyl)-4-methylpentanamide;
N-(cyanomethyl)-4-methyl-2-[3-(1H-pyrrolo[2,3-b]pyridin-5-yl)phenyl]pentanamide;
2-{3-[3-(2-aminoethyl)-1H-indol-5-yl]phenyl}-N-(cyanomethyl)-4-methylpentanamide;
(2R)-N-(cyanomethyl)-4-methyl-2-[4'-(4-methyl-1-piperazinyl)[1,1'-biphenyl]-3-yl]pentanamide;
(2R)-N-(cyanomethyl)-4-methyl-2-[4'-(1-piperazinyl)[1,1'-biphenyl]-3-yl]pentanamide;
N-(cyanomethyl)-4-methyl-2-[3-(6-quinolinyl)phenyl]pentanamide;
N-(cyanomethyl)-3-cyclopropyl-2-[4'-(4-methyl-1-piperazinyl)[1,1'-biphenyl]-3-yl]propanamide;
N-(cyanomethyl)-4-methyl-2-[4'-(1,2,3,6-tetrahydro-4-pyridinyl)[1,1'-biphenyl]-3-yl]pentanamide;
(4S)-N-(cyanomethyl)-4-methyl-2-[4'-(4-methyl-1-piperazinyl)[1,1'-biphenyl]-3-yl]hexanamide;
(2R)-N-(cyanomethyl)-2-{4'-[4-(2-hydroxyethyl)-1-piperazinyl][1,1'-biphenyl]-3-yl}-4-methylpentanamide;
N-(cyanomethyl)-4-methyl-2-[2'-(1-piperazinyl)[1,1'-biphenyl]-3-yl]pentanamide;
(2R)-N-(cyanomethyl)-4-methyl-2-{3-[6-(1-piperazinyl)-3-pyridinyl]phenyl}pentanamide;
(2R)-N-(cyanomethyl)-4-methyl-2-[4'-(4-pyridinyl)[1,1'-biphenyl]-3-yl]pentanamide;
(2R)-N-(cyanomethyl)-2-{4'-[4-(2-hydroxy-2-methylpropyl)-1-piperazinyl][1,1'-biphenyl]-3-yl}-4-methylpentanamide;
N-(cyanomethyl)-4-methyl-2-[4'-(4-piperidinyl)[1,1'-biphenyl]-3-yl]pentanamide;
4-Methyl-2-[4'-(4-methyl-piperazin-1-yl)-biphenyl-3-yl]-pentanoic acid cyanomethyl-amide;
2-{4'-[4-(2-Hydroxy-ethyl)-piperazin-1-yl]-biphenyl-3-yl}-4-methyl-pentanoic acid (1-cyano-cyclopropyl)-amide;
4-Methyl-2-[3'-(4-methyl-piperazin-1-yl)-biphenyl-3-yl]-pentanoic acid cyanomethyl-amide;
2-(3-{2-[4-(2-Hydroxy-ethyl)-piperazin-1-yl]-thiazol-4-yl}-phenyl)-4-methyl-pentanoic acid (1-cyano-cyclopropyl)-amide;
2-Biphenyl-3-yl-4-methyl-pentanoic acid (cyano-methyl-methyl)-amide;
2-Biphenyl-3-yl-4-methyl-pentanoic acid (1-cyano-3-methylsulfanyl-propyl)-amide;
[5-(2-Biphenyl-3-yl-4-methyl-pentanoylamino)-5-cyano-pentyl]-carbamic acid benzyl ester;
4-Methyl-2-[3-(4-methyl-piperazin-1-yl)-phenyl]-pentanoic acid cyanomethyl-amide;
2-Biphenyl-3-yl-4-methyl-pentanoic acid (1-cyano-pentyl)-amide;
4-Methyl-2-(3'-piperazin-1-yl-biphenyl-3-yl)-pentanoic acid cyanomethyl-amide;
4-{3'-[1-(Cyanomethyl-carbamoyl)-3-methyl-butyl]-biphenyl-3-yl}-piperazine-1-carboxylic acid tert-butyl ester;
2-(5-{4-[4-(2-Hydroxy-ethyl)-piperazin-1-yl]-phenyl}-pyridin-3-yl)-4-methyl-pentanoic acid cyanomethyl-amide;
2-{5-[4-(4-Formyl-piperazin-1-yl)-phenyl]-pyridin-3-yl}-4-methyl-pentanoic acid cyanomethyl-amide;
4-Methyl-2-[5-(4-piperazin-1-yl-phenyl)-pyridin-3-yl]-pentanoic acid cyanomethyl-amide;
3'-[1-(Cyanomethyl-carbamoyl)-3-methyl-butyl]-biphenyl-2-carboxylic acid methyl ester;
2-[3-(2,3-Dihydro-benzo[1,4]dioxin-6-yl)-phenyl]-4-methyl-pentanoic acid cyanomethyl-amide;
2-[4'-(1-Hydroxy-ethyl)-biphenyl-3-yl]-4-methyl-pentanoic acid cyanomethyl-amide;
2-(3',5'-Bis-trifluoromethyl-biphenyl-3-yl)-4-methyl-pentanoic acid cyanomethyl-amide;
2-(4'-Cyano-2'-methyl-biphenyl-3-yl)-4-methyl-pentanoic acid cyanomethyl-amide;
N-[1-(Cyanomethyl-carbamoyl)-2-(2-fluoro-3-methyl-phenylmethanesulfonyl)-ethyl]-benzamide;
N-[1-(Cyanomethyl-carbamoyl)-2-(2,5-difluoro-phenylmethanesulfonyl)-ethyl]-benzamide;
2-{3'-[4-(2-Hydroxy-ethyl)-piperazine-1-sulfonyl]-4'-methoxy-biphenyl-3-yl}-4-methyl-pentanoic acid cyanomethyl-amide;
3'-[1-(Cyanomethyl-carbamoyl)-3-methyl-butyl]-biphenyl-4-carboxylic acid (2-morpholin-4-yl-ethyl)-amide;
3'-[1-(Cyanomethyl-carbamoyl)-3-methyl-butyl]-biphenyl-3-carboxylic acid (2-morpholin-4-yl-ethyl)-amide;
4-Methyl-2-[3'-(2-morpholin-4-yl-ethylsulfamoyl)-biphenyl-3-yl]-pentanoic acid cyanomethyl-amide;
3'-[1-(Cyanomethyl-carbamoyl)-3-methyl-butyl]-biphenyl-2-carboxylic acid (2-morpholin-4-yl-ethyl)-amide;
3'-[1-(Cyanomethyl-carbamoyl)-3-methyl-butyl]-biphenyl-4-carboxylic acid (2-dimethylamino-ethyl)-methyl-amide;
3'-[1-(Cyanomethyl-carbamoyl)-3-methyl-butyl]-biphenyl-4-carboxylic acid (2-dimethylamino-ethyl)-amide;
3'-[1-(Cyanomethyl-carbamoyl)-3-methyl-butyl]-biphenyl-4-carboxylic acid methyl-(2-morpholin-4-yl-ethyl)-amide;
2-(3'-Fluoro-biphenyl-3-yl)-4-methyl-pentanoic acid cyanomethyl-amide;
2-[3-(6-Bromo-pyridin-2-yl)-phenyl]-4-methyl-pentanoic acid cyanomethyl-amide;
2-(2'-Cyano-biphenyl-3-yl)-4-methyl-pentanoic acid cyanomethyl-amide;
2-(3'-Cyano-biphenyl-3-yl)-4-methyl-pentanoic acid cyanomethyl-amide;
2-(4'-Cyano-biphenyl-3-yl)-4-methyl-pentanoic acid cyanomethyl-amide;
4-Methyl-2-(3-quinolin-8-yl-phenyl)-pentanoic acid cyanomethyl-amide;

4-Methyl-2-(3-quinolin-3-yl-phenyl)-pentanoic acid cyanomethyl-amide;
4-Methyl-2-(4'-trifluoromethoxy-biphenyl-3-yl)-pentanoic acid cyanomethyl-amide;
4-Methyl-2-[3-(5-nitro-thiazol-2-yl)-phenyl]-pentanoic acid cyanomethyl-amide;
2-(4'-Acetylamino-biphenyl-3-yl)-4-methyl-pentanoic acid cyanomethyl-amide;
4-Methyl-2-[4'-(4-methyl-piperazine-1-sulfonyl)-biphenyl-3-yl]-pentanoic acid cyanomethyl-amide;
4-Methyl-2-[3'-(4-methyl-piperazine-1-sulfonyl)-biphenyl-3-yl]-pentanoic acid cyanomethyl-amide;
4-Methyl-2-[4'-(piperazine-1-sulfonyl)-biphenyl-3-yl]-pentanoic acid cyanomethyl-amide;
2-{4'-[4-(2-Hydroxy-ethyl)-piperazine-1-carbonyl]-biphenyl-3-yl}-4-methyl-pentanoic acid cyanomethyl-amide;
2-{3'-[4-(2-Hydroxy-ethyl)-piperazine-1-carbonyl]-biphenyl-3-yl}-4-methyl-pentanoic acid cyanomethyl-amide;
4-Methyl-2-[4'-(2-morpholin-4-yl-ethylsulfamoyl)-biphenyl-3-yl]-pentanoic acid cyanomethyl-amide;
2-(4'-{2-[Bis-(2-hydroxy-ethyl)-amino]-ethylsulfamoyl}-biphenyl-3-yl)-4-methyl-pentanoic acid cyanomethyl-amide;
4-Methyl-2-[4'-(3-morpholin-4-yl-propylsulfamoyl)-biphenyl-3-yl]-pentanoic acid cyanomethyl-amide;
4-Methyl-2-[4'-(3-morpholin-4-yl-propylsulfamoyl)-biphenyl-3-yl]-pentanoic acid cyanomethyl-amide;
2-[4'-(2-Dimethylamino-1-methyl-ethylsulfamoyl)-biphenyl-3-yl]-4-methyl-pentanoic acid cyanomethyl-amide;
2-[4'-(2-Hydroxy-ethylsulfamoyl)-biphenyl-3-yl]-4-methyl-pentanoic acid cyanomethyl-amide;
2-[4'-(2-Hydroxy-ethylsulfamoyl)-biphenyl-3-yl]-4-methyl-pentanoic acid cyanomethyl-amide;
2-[4'-(3-Dimethylamino-pyrrolidine-1-sulfonyl)-biphenyl-3-yl]-4-methyl-pentanoic acid cyanomethyl-amide;
2-{3'-[2-(3-Dimethylamino-pyrrolidin-1-yl)-thiazol-4-yl]-biphenyl-3-yl}-4-methyl-pentanoic acid cyanomethyl-amide;
4-Methyl-2-[4'-(2-piperazin-1-yl-thiazol-4-yl)-biphenyl-3-yl]-pentanoic acid cyanomethyl-amide;
2-{3'-[2-(4-tert-Butyl-piperazin-1-yl)-thiazol-4-yl]-biphenyl-3-yl}-4-methyl-pentanoic acid cyanomethyl-amide;
2-{3'-[2-(3-Dimethylamino-pyrrolidin-1-yl)-thiazol-4-yl]-biphenyl-3-yl}-4-methyl-pentanoic acid cyanomethyl-amide;
4-Methyl-2-[3'-(2-piperazin-1-yl-thiazol-4-yl)-biphenyl-3-yl]-pentanoic acid (1-cyano-cyclopropyl)-amide;
4-Methyl-2-[3'-(2-piperazin-1-ylmethyl-thiazol-4-yl)-biphenyl-3-yl]-pentanoic acid cyanomethyl-amide;
4-Methyl-2-[4'-(2-piperazin-1-yl-thiazol-4-yl)-biphenyl-3-yl]-pentanoic acid (1-cyano-cyclopropyl)-amide;
4-Methyl-2-{4'-[methyl-(1-methyl-pyrrolidin-3-yl)-sulfamoyl]-biphenyl-3-yl}-pentanoic acid cyanomethyl-amide; and
2-[4'-(4-Formyl-piperazine-1-sulfonyl)-biphenyl-3-yl]-4-methyl-pentanoic acid cyanomethyl-amide.

7. A compound selected from the group consisting of:
N-(cyanomethyl)-4-methyl-2-[3-(pyrid-2-yl)phenyl]pentanamide;
N-(cyanomethyl)-2-[3-(1H-indol-5-yl)phenyl]-4-methylpentanamide;
N-(cyanomethyl)-2-[3-(1H-indol-6-yl)phenyl]-4-methylpentanamide;
N-cyanomethyl-2-(4'-methylsulfonylbiphenyl-3-yl)-4-methylpentanamide;
N-(cyanomethyl)-4-methyl-2-[3-(5-pyrimidinyl)phenyl]pentanamide;
N-(cyanomethyl)-4-methyl-2-[3-(2-pyrimidinyl)phenyl]pentanamide;
3'-(1-cyanomethylcarbamoyl)-3-methylbutyl]biphenyl-4-carboxamide;
N-(cyanomethyl)-2-[3-(4-isoquinolinyl)phenyl]-4-methylpentanamide;
N-(cyanomethyl)-4-methyl-2-[3-(3-quinolinyl)phenyl]pentanamide;
2-[4'-(acetylamino)[1,1'-biphenyl]-3-yl]-N-(cyanomethyl)-4-methylpentanamide;
N-(cyanomethyl)-2-[3-(3-furyl)phenyl]-4-methylpentanamide;
N-(cyanomethyl)-4-methyl-2-[3-(2-methyl-6-quinolinyl)phenyl]pentanamide;
N-(cyanomethyl)-2-[3-(4,5-dichloro-1H-imidazol-2-yl)phenyl]-4-methylpentanamide;
N-(cyanomethyl)-2-[3-(3,5-dimethyl-4-isoxazolyl)phenyl]-4-methylpentanamide;
tert-butyl 3'-(1-cyanomethylcarbamoyl-3-methylbutyl)biphenyl-4-ylcarbamate;
N-(cyanomethyl)-4-methyl-2-[3-(1-oxo-2,3-dihydro-1H-inden-5-yl)phenyl]pentanamide;
N-(cyanomethyl)-2-(3-methoxyphenyl)-4-methylpentanamide;
2,2-dichloroethyl 3'-(1-cyanomethylcarbamoyl-3-methylbutyl)biphenyl-4-ylcarbamate;
N-(cyanomethyl)-4-methyl-2-(4'-phenoxy[1,1'-biphenyl]-3-yl)pentanamide;
N-(cyanomethyl)-4-methyl-2-[3-(2-oxo-2,3-dihydro-1,3-benzothiazol-6-yl)phenyl]pentanamide;
3-(1-{[(cyanomethyl)amino]carbonyl}-3-methylbutyl)phenyl 2-(3-hydroxyphenyl)-4-methylpentanoate;
tert-butyl 3'-(1-cyanomethylcarbamoyl-3-methylbutyl)biphenyl-4-ylmethylcarbamate;
N-(cyanomethyl)-2-[3-(2,3-dihydro-1H-indol-5-yl)phenyl]-4-methylpentanamide;
tert-butyl N-5-[3-(1-cyanomethylcarbamoyl-3-methylbutyl)phenyl]pyrimidin-2-yl-N-(tert-butoxycarbonyl)carbamate;
N-(cyanomethyl)-4-methyl-2-[3-(1-methyl-1H-indol-5-yl)phenyl]pentanamide;
N-(cyanomethyl)-4-methyl-2-[3-(7-nitro-1H-indol-5-yl)phenyl]pentanamide;
N-(cyanomethyl)-4-methyl-2-[3-(1H-pyrrolo[2,3-b]pyridin-5-yl)phenyl]pentanamide;
2-[3-(7-amino-1H-indol-5-yl)phenyl]-N-(cyanomethyl)-4-methylpentanamide;
N-(cyanomethyl)-4-methyl-2-[3-(7-nitro-2,3-dihydro-1H-indol-5-yl)phenyl]pentanamide;
5-[3-(1-{[(cyanomethyl)amino]carbonyl}-3-methylbutyl)phenyl]-1H-indole-2-carboxylic acid;
5-[3-(1-{[(cyanomethyl)amino]carbonyl}-3-methylbutyl)phenyl]-1H-indole-2-carboxamide;
N-(cyanomethyl)-4-methyl-2-[3-(2-oxo-2,3-dihydro-1H-pyrrolo[2,3-b]pyridin-5-yl)phenyl]pentanamide;
N-(cyanomethyl)-4-methyl-2-[3'-(4-morpholinyl)[1,1'-biphenyl]-3-yl]pentanamide;
N-(cyanomethyl)-4-methyl-2-[4'-(4-morpholinyl)[1,1'-biphenyl]-3-yl]pentanamide;
N-(cyanomethyl)-4-methyl-2-[2'-(4-morpholinyl)[1,1'-biphenyl]-3-yl]pentanamide;
N-(cyanomethyl)-2-(3-{3-[(dimethylamino)methyl]-1H-indol-5-yl}phenyl)-4-methylpentanamide;

2-[4'-(aminomethyl)[1,1'-biphenyl]-3-yl]-N-(cyanomethyl)-4-methylpentanamide;

N-(cyanomethyl)-4-methyl-2-[4'-(4-methyl-1-piperazinyl)[1,1'-biphenyl]-3-yl]pentanamide;

N-(cyanomethyl)-4-methyl-2-[4'-(1-piperazinyl)[1,1'-biphenyl]-3-yl]pentanamide;

ethyl 4-[3'-(1-{[(cyanomethyl)amino]carbonyl}-3-methylbutyl)[1,1'-biphenyl]-4-yl]-1-piperazinecarboxylate; and 2-{3-[3-(2-aminoethyl)-1H-indol-5-yl]phenyl}-N-(cyanomethyl)-4-methylpentanamide; and the N-oxide compounds, prodrug derivatives, protected derivatives, individual isomers and mixtures of isomers thereof; and the pharmaceutically acceptable salts thereof.

8. A process for preparing a compound of Formula I

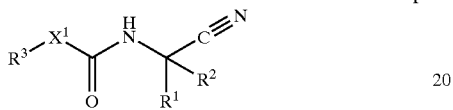

$X^1$ is selected from a group consisting of —$CR^4R^5$— or —$CHR^7$—, wherein:

$R^4$ and $R^5$ along with the carbon atom to which they are attached represents

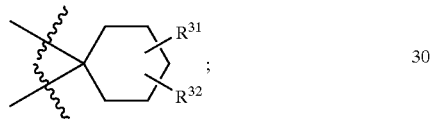

where $R^{31}$ and $R^{32}$ independently represent hydrogen or hydroxy, alternatively $R^{31}$ and $R^{32}$ can be taken together to represent an oxo (═O) group;

$R^7$ is $(C_{4-8})$alkyl or —$CH_2$— cyclopropyl;

$R^1$ is hydrogen;

$R^2$ is selected from a group consisting of hydrogen and $R^{2a}$;

alternatively $R^1$ and $R^2$ together represent —$CH_2$—$CH_2$— or —$CH_2NR^8CH_2$—;

$R^{2a}$ represents $(C_{2-4})$alkyl optionally substituted with a group selected from —$NR^8C(O)R^{35}$, —$OR^{35}$, —$SR^{35}$, —$S(O)R^{35}$, —$S(O)_2R^{35}$, —$C(O)R^{35}$, —$S(O)_2NR^8R^{35}$ and —$OP(O)(OR^8)OR^{35}$;

$R^{35}$ is selected from a group consisting of $(C_{1-4})$alkyl, —$(CH_2)_{0-3}(C_{3-12})$cycloalkyl, —$(CH_2)_{0-3}$hetero$(C_{5-10})$cycloalkyl, —$(CH_2)_{0-3}(C_{6-10})$aryl, —$(CH_2)_{0-3}$hetero$(C_{5-10})$aryl, —$(CH_2)_{0-3}(C_{9-10})$bicycloaryl and —$(CH_2)_{0-3}$hetero$(C_{8-10})$bicycloaryl;

$R^3$ is selected from a group consisting of $(C_{6-10})$aryl, and hetero$(C_{5-10})$aryl, wherein:

$R^3$ may be substituted further by a radical selected from a group consisting of —$X^3NR^8R^{21}$, —$X^3NR^8C(O)R^{21}$, —$X^3NR^8C(O)OR^{21}$, —$X^3NR^8C(O)NR^8R^{21}$, —$X^3OR^{21}$, —$X^3SR^{21}$, —$X^3C(O)R^{21}$, —$X^3C(O)OR^{21}$, —$X^3OC(O)R^{21}$, —$X^3C(O)NR^8R^{21}$, —$X^3OR^{52}$, —$X^3CONR^8R^{52}$, and —$R^{21}$, wherein:

$X^3$ is a bond or $(C_{1-6})$alkylene, $R^8$ at each occurrence independently is hydrogen or $(C_{1-6})$alkyl, $R^{52}$ represents —$CH_2CH_2$—$N(CH_2CH_2OH)_2$, —$CH(CH_3)CH_2N(CH_3)_2$, —$CH_2CH_2OH$, —$CH_2CH_2N(CH_3)_2$ or —$CH_2CN$, and $R^{21}$ is —$(C_{1-8})$alkyl or —$X^3R^{22}$, and $R^{22}$ is selected from a group consisting of hetero$(C_{5-10})$cycloalkyl, $(C_{6-10})$aryl, hetero$(C_{5-10})$aryl and hetero$(C_{8-10})$bicycloaryl, wherein:

$R^{22}$ may be substituted further by a radical selected from a group consisting of $(C_{1-4})$alkyl, —$X^3NR^8R^{23}$, —$X^3C(O)NR^8R^{23}$, —$X^3OC(O)NR^8R^{23}$, —$X^3S(O)_2NR^8R^{23}$, —$X^3OR^{52}$, —$X^3CONR^8R^{52}$, —$X^3SO_2NR^8R^{52}$, —$X^3P(O)(OR^8)OR^{23}$, —$X^3OP(O)(OR^8)OR^{23}$ and —$R^{23}$, wherein:

$X^3$ is a bond or $(C_{1-6})$alkylene and $R^8$ at each occurrence independently is hydrogen or $(C_{1-6})$alkyl, $R^{52}$ represents $CH_2CH_2$—$N(CH_2CH_2OH)_2$, $CH(CH_3)CH_2N(CH_3)_2$, $CH_2CH_2OH$, $CH_2CH_2N(CH_3)_2$ or $CH_2CN$, and $R^{23}$ is $(C_{1-8})$alkyl or —$X^3R^{24}$, wherein $X^3$ is as defined above and $R^{24}$ is selected from a group consisting of hetero$(C_{5-10})$cycloalkyl and hetero$(C_{5-10})$aryl, wherein $R^{24}$ may be substituted further by a radical selected from a group consisting of —$X^3NR^8R^{25}$, —$X^3C(O)OR^{25}$, —$X^3S(O)_2NR^8R^{25}$, —$X^3OR^{52}$ and —$R^{25}$, wherein:

$X^3$ is a bond or $(C_{1-6})$alkylene and $R^8$ at each occurrence independently is hydrogen or $(C_{1-6})$alkyl, $R^{52}$ represents —$CH_2CH_2$—$N(CH_2CH_2OH)_2$, —$CH(CH_3)CH_2N(CH_3)_2$, —$CH_2CH_2OH$, —$CH_2CH_2N(CH_3)_2$ or —$CH_2CN$, and $R^{25}$ is —$(C_{1-8})$alkyl or —$X^3R^{26}$, wherein $X^3$ is as defined above and $R^{26}$ is selected from a group consisting of hetero$(C_{5-10})$cycloalkyl; and wherein any of the $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl contained within $R^3$, $R^{22}$, $R^{24}$ and $R^{26}$ may be substituted further with up to five substituents selected from a group consisting of $(C_{1-6})$alkyl, cyano, halo, nitro, halo-substituted $(C_{1-3})$alkyl, —$X^3NR^{16}R^{16}$, —$X^3OR^{16}$, and —$X^3C(O)R^{16}$, wherein:

$X^3$ is a bond or $(C_{1-6})$alkylene, $R^{52}$ represents —$CH_2CH_2$—$N(CH_2CH_2OH)_2$, —$CH(CH_3)CH_2N(CH_3)_2$, —$CH_2CH_2OH$, —$CH_2CH_2N(CH_3)_2$ or —$CH_2CN$, $R^{16}$ at each occurence independently is selected from a group consisting of hydrogen, $(C_{1-3})$alkyl or halo-substituted $(C_{1-3})$alkyl and $R^{17}$ is —$(C_{1-3})$alkyl or halo-substituted $(C_{1-3})$alkyl; and the N-oxide derivatives, prodrug derivatives, protected derivatives, individual stereo isomers and mixtures of stereo isomers, and pharmaceutically acceptable salts thereof, with the proviso that only one of $R^3$, $R^{22}$, $R^{24}$ and $R^{26}$ represents a fused bicyclic ring structure; which process comprises:

(A) reacting a compound of Formula 2:

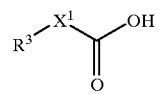

with a compound of the formula $NH_2CR^1R^2CN$, wherein $X^1$, $R^1$, $R^2$ and $R^3$ are as defined above; and (B) optionally converting a compound of Formula I into a pharmaceutically acceptable salt;

(C) optionally converting a salt form of a compound of Formula I to non-salt form;

(D) optionally converting an unoxidized form of a compound of Formula I into a pharmaceutically acceptable N-oxide;
(E) optionally converting an N-oxide form of a compound of Formula I its unoxidized form;
(F) optionally resolving an individual isomer of a compound of Formula I from a mixture of isomers;
(G) optionally converting a non-derivatized compound of Formula I into a pharmaceutically prodrug derivative; and
(H) optionally converting a prodrug derivative of a compound of Formula I to its non-derivatized form.

9. A pharmaceutical composition comprising a therapeutically effective amount of a pharmaceutical compound in combination with one or more pharmaceutically acceptable excipient(s), wherein said pharmaceutical compound has the formula:

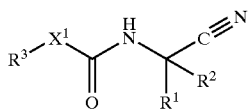

I in which:
$X^1$ is selected from a group consisting of —$CR^4R^5$—, —$CR^6R^7$— and —$NR^7$—, wherein:
$R^4$ and $R^5$ along with the carbon atom to which they are attached represents

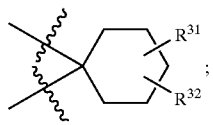

where $R^{31}$ and $R^{32}$ independently represent hydrogen or hydroxy, alternatively $R^{31}$ and $R^{32}$ can be taken together to represent an oxo (=O) group;
$R^6$ is hydrogen or $(C_{1-6})$alkyl; and
$R^7$ is $(C_{1-8})$alkyl or $(CH_2)_{1-3}$ cyclopropyl;
$R^1$ is hydrogen or $(C_{1-6})$alkyl;
$R^2$ is selected from a group consisting of hydrogen and $R^{2a}$;
alternatively $R^1$ and $R^2$ together represent $C_{2-5}$ alkylene or —$CH_2NR^8CH_2$—, or both $R^1$ and $R^2$ simultaneously represent fluoro;
$R^{2a}$ represents $(C_{1-8})$ alkyl optionally substituted with a group selected from —$NR^8R^{35}$, —$NR^8C(O)R^{35}$, —$NR^8C(O)OR^{35}$, —$NR^8C(O)NR^8R^{35}$, —$NR^8C(NR^8)NR^8R^{35}$, —$OR^{35}$, —$SR^{35}$, —$S(O)R^{35}$, —$S(O)_2R^{35}$, —$C(O)R^{35}$, —$C(O)OR^{35}$, —$OC(O)R^{35}$, —$C(O)NR^8R^{35}$, —$OC(O)NR^8R^{35}$, —$S(O)_2NR^8R^{35}$, —$P(O)(OR^8)OR^{35}$, —$OR^{52}$, —$CONR^8R^{52}$, —$SO_2NR^8R^{52}$ and —$OP(O)(OR^8)OR^{35}$;
$R^{35}$ is selected from a group consisting of $(C_{1-4})$alkyl, —$(CH_2)_{0-3}(C_{3-12})$cycloalkyl, —$(CH_2)_{0-3}$hetero$(C_{5-10})$cycloalkyl, —$(CH_2)_{0-3}(C_{6-10})$aryl, —$(CH_2)_{0-3}$hetero$(C_{5-10})$aryl, —$(CH_2)_{0-3}(C_{9-10})$bicycloaryl and —$(CH_2)_{0-3}$hetero$(C_{8-10})$bicycloaryl;
$R^3$ is selected from a group consisting of $(C_{6-10})$aryl, hetero$(C_{5-10})$aryl, $(C_{9-10})$bicycloaryl and hetero$(C_{8-10})$bicycloaryl, wherein:

$R^3$ may be substituted further by a radical selected from a group consisting of —$X^3NR^8R^{21}$, —$X^3NR^8C(O)R^{21}$, —$X^3NR^8C(O)OR^{21}$, —$X^3NR^8C(O)NR^8R^{21}$, —$X^3NR^8C(NR^8)NR^8R^{21}$, —$X^3OR^{21}$, —$X^3SR^{21}$, —$X^3S(O)R^{21}$, —$X^3S(O)_2R^{21}$, —$X^3C(O)R^{21}$, —$X^3C(O)OR^{21}$, —$X^3OC(O)R^{21}$, —$X^3C(O)NR^8R^{21}$, —$X^3OC(O)NR^8R^{21}$, —$X^3S(O)_2NR^8R^{21}$, —$X^3P(O)(OR^8)OR^{21}$, —$X^3OR^{52}$, —$X^3CONR^8R^{52}$, —$X^3SO_2NR^8R^{52}$, —$X^3OP(O)(OR^8)OR^{21}$ and —$R^{21}$, wherein:
$X^3$ is a bond or $(C_{1-6})$alkylene, $R^8$ at each occurrence independently is hydrogen or $(C_{1-6})$alkyl, $R^{52}$ represents —$CH_2CH_2$—$N(CH_2CH_2OH)_2$, —$CH(CH_3)CH_2N(CH_3)_2$, —$CH_2CH_2OH$, —$CH_2CH_2N(CH_3)_2$ or —$CH_2CN$, and $R^{21}$ is —$(C_{1-8})$alkyl or —$X^3R^{22}$, wherein $X^3$ is as defined above and $R^{22}$ is selected from a group consisting of $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl, wherein:
$R^{22}$ may be substituted further by a radical selected from a group consisting of —$X^3NR^8R^{23}$, —$X^3NR^8C(O)R^{23}$, —$X^3NR^8C(O)OR^{23}$, —$X^3NR^8C(O)NR^8R^{23}$, —$X^3OR^{23}$, —$X^3NR^8C(NR^8)NR^8R^{23}$, —$X^3SR^{23}$, —$X^3S(O)R^{23}$, —$X^3S(O)_2R^{23}$, —$X^3C(O)R^{23}$, —$X^3OC(O)R^{23}$, —$X^3C(O)OR^{23}$, —$X^3C(O)NR^8R^{23}$, —$X^3OC(O)NR^8R^{23}$, —$X^3S(O)_2NR^8R^{23}$, —$X^3OR^{52}$, —$X^3CONR^8R^{52}$, —$X^3SO_2NR^8R^{52}$, —$X^3P(O)(OR^8)OR^{23}$, —$X^3OP(O)(OR^8)OR^{23}$ and —$R^{23}$, wherein:
$X^3$ is a bond or $(C_{1-6})$alkylene and $R^8$ at each occurrence independently is hydrogen or $(C_{1-6})$alkyl, $R^{52}$ represents $CH_2CH_2$—$N(CH_2CH_2OH)_2$, $CH(CH_3)CH_2N(CH_3)_2$, $CH_2CH_2OH$, $CH_2CH_2N(CH_3)_2$ or $CH_2CN$, and $R^{23}$ is $(C_{1-8})$alkyl or —$X^3R^{24}$, wherein $X^3$ is as defined above and $R^{24}$ is selected from a group consisting of $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl, wherein
$R^{24}$ may be substituted further by a radical selected from a group consisting of —$X^3NR^8R^{25}$, —$X^3NR^8C(O)R^{25}$, —$X^3NR^8C(O)OR^{25}$, —$X^3OR^{25}$, —$X^3NR^8C(O)NR^8R^{25}$, —$X^3NR^8C(NR^8)NR^8R^{25}$, —$X^3SR^{25}$, —$X^3S(O)R^{25}$, —$X^3S(O)_2R^{25}$, —$X^3C(O)R^{25}$, —$X^3OC(O)R^{25}$, —$X^3C(O)OR^{25}$, —$X^3C(O)NR^8R^{25}$, —$X^3OC(O)NR^8R^{25}$, —$X^3S(O)_2NR^8R^{25}$, —$X^3P(O)(OR^8)OR^{25}$, —$X^3OR^{25}$, —$X^3CONR^8R^{52}$, —$X^3SO_2NR^8R^{52}$, —$X^3OP(O)(OR^8)OR^{25}$ and —$R^{25}$, wherein:
$X^3$ is a bond or $(C_{1-6})$alkylene and $R^8$ at each occurrence independently is hydrogen or $(C_{1-6})$ alkyl, $R^{52}$ represents —$CH_2CH_2$—$N(CH_2CH_2OH)_2$, —$CH(CH_3)CH_2N(CH_3)_2$, —$CH_2CH_2OH$, —$CH_2CH_2N(CH_3)_2$ or —$CH_2CN$, and $R^{25}$ is —$(C_{1-8})$alkyl or —$X^3R^{26}$, wherein $X^3$ is as defined above and $R^{26}$ is selected from a group consisting of $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl; wherein any of the $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl contained within $R^3$, $R^{22}$, $R^{24}$ and $R^{26}$ may be substituted further with up to five substituents selected from a group consisting of $(C_{1-6})$alkyl, $(C_{1-6})$alkylidene, cyano, halo, nitro, halo-substituted $(C_{1-3})$alkyl, $—X^3NR^{16}R^{16}$, $—X^3NR^{16}C(O)OR^{16}$, $—X^3NR^{16}C(O)NR^{16}R^{16}$, $—X^3NR^{16}C(NR^{16})NR^{16}R^{16}$, $—X^3OR^{16}$, $—X^3SR^{16}$, $—X^3C(O)OR^{16}$, $—X^3C(O)NR^{16}R^{16}$, $—X^3S(O)_2NR^{16}R^{16}$, $—X^3P(O)(OR^8)OR^{16}$, $—X^3OR^{52}$, $—X^3CONR^8R^{52}$, $—X^3C(O)R^{16}$, $—X^3SO_2NR^8R^{52}$, $—X^3S(O)R^{17}$, $—X^3OP(O)(OR^8)OR^{16}$, $—X^3NR^{16}C(O)R^{17}$, $—X^3S(O)_2R^{17}$ and $—X^3C(O)R^{16}$, wherein:

$X^3$ is a bond or $(C_{1-6})$alkylene, $R^{52}$ represents $—CH_2CH_2—N(CH_2CH_2OH)_2$, $—CH(CH_3)CH_2N(CH_3)_2$, $—CH_2CH_2OH$, $—CH_2CH_2N(CH_3)_2$ or $—CH_2CN$, $R^{16}$ at each occurrence independently is selected from a group consisting of hydrogen, $(C_{1-3})$alkyl or halo-substituted $(C_{1-3})$alkyl and $R^{17}$ is $—(C_{1-3})$alkyl or halo-substituted $(C_{1-3})$alkyl; or the N-oxide compounds, prodrug derivatives, protected derivatives, individual stereo isomers and mixtures of stereo isomers, or pharmaceutically acceptable salts thereof, with the proviso that only one of $R^3$, $R^{22}$, $R^{24}$ and $R^{26}$ represents a fused bicyclic ring structure.

10. The composition of claim 9 which further comprises one or more active ingredient(s) selected from the group consisting of (i) a therapeutically effective amount of a bisphosphonic acid or acid ester thereof or a pharmaceutically acceptable salt thereof and (ii) a therapeutically effective amount of an estrogen receptor agonist or a pharmaceutically acceptable salt thereof.

11. The composition of claim 10 wherein the bisphosphonic acid is selected from the group consisting of 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof.

12. The composition of claim 11 wherein the bisphosphonic acid is 1,1-dichloromethylene-1,1-diphosphonic acid or a pharmaceutically acceptable salt thereof.

13. The composition of claim 12 which comprises 1,1-dichloromethylene-1,1-diphosphonate monosodium trihydrate.

14. A pharmaceutical composition comprising a therapeutically effective amount of a compound of claim 7 in combination with one or more pharmaceutically acceptable excipient(s).

15. The composition of claim 14 which further comprises one or more active ingredient(s) selected from the group consisting of (i) a therapeutically effective amount of a bisphosphonic acid or acid ester thereof or a pharmaceutically acceptable salt thereof and (ii) a therapeutically effective amount of an estrogen receptor agonist or a pharmaceutically acceptable salt thereof.

16. The composition of claim 15 wherein the bisphosphonic acid is selected from the group consisting of 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof.

17. The composition of claim 16 wherein the bisphosphonic acid is 1,1-dichloromethylene-1,1-diphosphonic acid or a pharmaceutically acceptable salt thereof.

18. The composition of claim 17 which comprises 1,1-dichloromethylene-1,1-diphosphonate monosodium trihydrate.

19. A method for treating a disease in an animal in which inhibition of a cysteine protease can prevent, inhibit or ameliorate the pathology or symptomatology of the disease, which method comprises administering to the animal a therapeutically effective amount of a compound having the formula:

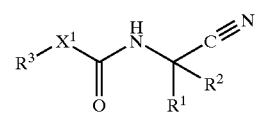

I in which:

$X^1$ is selected from a group consisting of $—CR^4R^5—$, $—CR^6R^7—$ and $—NR^7—$, wherein:

$R^4$ and $R^5$ along with the carbon atom to which they are attached represents

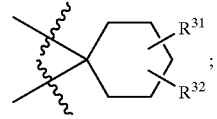

where $R^{31}$ and $R^{32}$ independently represent hydrogen or hydroxy, alternatively $R^{31}$ and $R^{32}$ can be taken together to represent an oxo (=O) group;

$R^6$ is hydrogen or $(C_{1-6})$alkyl; and $R^7$ is $(C_{1-8})$alkyl or $(CH_2)_{1-3}$ cyclopropyl;

$R^1$ is hydrogen or $(C_{1-6})$alkyl;

$R^2$ is selected from a group consisting of hydrogen and $R^{2a}$;

alternatively $R^1$ and $R^2$ together represent $C_{2-5}$ alkylene or $—CH_2NR^8CH_2—$, or both $R^1$ and $R^2$ simultaneously represent fluoro;

$R^{2a}$ represents $(C_{1-8})$ alkyl optionally substituted with a group selected from $—NR^8R^{35}$, $—NR^8C(O)R^{35}$, $—NR^8C(O)OR^{35}$, $—NR^8C(O)NR^8R^{35}$, $—NR^8C(NR^8)NR^8R^{35}$, $—OR^{35}$, $—SR^{35}$, $—S(O)R^{35}$, $—S(O)_2R^{35}$, $—C(O)R^{35}$, $—C(O)OR^{35}$, $—OC(O)R^{35}$, $—C(O)NR^8R^{35}$, $—OC(O)NR^8R^{35}$, $—S(O)_2NR^8R^{35}$, $—P(O)(OR^8)OR^{35}$, $—OR^{52}$, $—CONR^8R^{52}$, $—SO_2NR^8R^{52}$ and $—OP(O)(OR^8)OR^{35}$;

$R^{35}$ is selected from a group consisting of $(C_{1-4})$alkyl, $-(CH_2)_{0-3}(C_{3-12})$cycloalkyl, $-(CH_2)_{0-3}$hetero$(C_{5-10})$cycloalkyl, $-(CH_2)_{0-3}(C_{6-10})$aryl, $-(CH_2)_{0-3}$hetero$(C_{5-10})$aryl, $-(CH_2)_{0-3}(C_{9-10})$bicycloaryl and $-(CH_2)_{0-3}$hetero$(C_{5-10})$bicycloaryl;

$R^3$ is selected from a group consisting of $(C_{6-10})$aryl, hetero$(C_{5-10})$aryl, $(C_{9-10})$bicycloaryl and hetero$(C_{8-10})$bicycloaryl, wherein:

$R^3$ may be substituted further by a radical selected from a group consisting of $-X^3NR^8R^{21}$, $-X^3NR^8C(O)R^{21}$, $-X^3NR^8C(O)OR^{21}$, $-X^3NR^8C(O)NR^8R^{21}$, $-X^3NR^8C(NR^8)NR^8R^{21}$, $-X^3OR^{21}$, $-X^3SR^{21}$, $-X^3S(O)R^{21}$, $-X^3S(O)_2R^{21}$, $-X^3C(O)R^{21}$, $-X^3C(O)OR^{21}$, $-X^3OC(O)R^{21}$, $-X^3C(O)NR^8R^{21}$, $-X^3OC(O)NR^8R^{21}$, $-X^3S(O)_2NR^8R^{21}$, $-X^3P(O)(OR^8)OR^{21}$, $-X^3OR^{52}$, $-X^3CONR^8R^{52}$, $-X^3SO_2NR^8R^{52}$, $-X^3OP(O)(OR^8)OR^{21}$ and $-R^{21}$, wherein:

$X^3$ is a bond or $(C_{1-6})$alkylene, $R^8$ at each occurrence independently is hydrogen or $(C_{1-6})$alkyl, $R^{52}$ represents $-CH_2CH_2-N(CH_2CH_2OH)_2$, $-CH(CH_3)CH_2N(CH_3)_2$, $-CH_2CH_2OH$, $-CH_2CH_2N(CH_3)_2$ or $-CH_2CN$, and $R^{21}$ is $-(C_{1-8})$alkyl or $-X^3R^{22}$, wherein $X^3$ is as defined above and $R^{22}$ is selected from a group consisting of $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl, wherein:

$R^{22}$ may be substituted further by a radical selected from a group consisting of $-X^3NR^8R^{23}$, $-X^3NR^8C(O)R^{23}$, $-X^3NR^8C(O)OR^{23}$, $-X^3NR^8C(O)NR^8R^{23}$, $-X^3OR^{23}$, $-X^3NR^8C(NR^8)NR^8R^{23}$, $-X^3SR^{23}$, $-X^3S(O)R^{23}$, $-X^3S(O)_2R^{23}$, $-X^3C(O)R^{23}$, $-X^3OC(O)R^{23}$, $-X^3C(O)OR^{23}$, $-X^3C(O)NR^8R^{23}$, $-X^3OC(O)NR^8R^{23}$, $-X^3S(O)_2NR^8R^{23}$, $-X^3OR^{52}$, $-X^3CONR^8R^{52}$, $-X^3SO_2NR^8R^{52}$, $-X^3P(O)(OR^8)OR^{23}$, $-X^3OP(O)(OR^8)OR^{23}$ and $-R^{23}$, wherein:

$X^3$ is a bond or $(C_{1-6})$alkylene and $R^8$ at each occurrence independently is hydrogen or $(C_{1-6})$alkyl, $R^{52}$ represents $CH_2CH_2-N(CH_2CH_2OH)_2$, $CH(CH_3)CH_2N(CH_3)_2$, $CH_2CH_2OH$, $CH_2CH_2N(CH_3)_2$ or $CH_2CN$, and $R^{23}$ is $(C_{1-8})$alkyl or $-X^3R^{24}$, wherein $X^3$ is as defined above and $R^{24}$ is selected from a group consisting of $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl, wherein $R^{24}$ may be substituted further by a radical selected from a group consisting of $-X^3NR^8R^{25}$, $-X^3NR^8C(O)R^{25}$, $-X^3NR^8C(O)OR^{25}$, $-X^3OR^{25}$, $-X^3NR^8C(O)NR^8R^{25}$, $-X^3NR^8C(NR^8)NR^8R^{25}$, $-X^3SR^{25}$, $-X^3S(O)R^{25}$, $-X^3S(O)_2R^{25}$, $-X^3C(O)R^{25}$, $-X^3OC(O)R^{25}$, $-X^3C(O)OR^{25}$, $-X^3C(O)NR^8R^{25}$, $-X^3OC(O)NR^8R^{25}$, $-X^3S(O)_2NR^8R^{25}$, $-X^3P(O)(OR^8)OR^{25}$, $-X^3OR^{25}$, $-X^3CONR^8R^{52}$, $-X^3SO_2NR^8R^{52}$, $-X^3OP(O)(OR^8)OR^{25}$ and $-R^{25}$, wherein:

$X^3$ is a bond or $(C_{1-6})$alkylene and $R^8$ at each occurrence independently is hydrogen or $(C_{1-6})$alkyl, $R^{52}$ represents $-CH_2CH_2-N(CH_2CH_2OH)_2$, $-CH(CH_3)CH_2N(CH_3)_2$, $-CH_2CH_2OH$, $-CH_2CH_2N(CH_3)_2$ or $-CH_2CN$, and $R^{25}$ is $-(C_{1-8})$alkyl or $-X^3R^{26}$, wherein $X^3$ is as defined above and $R^{26}$ is selected from a group consisting of $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl; wherein any of the $(C_{3-10})$cycloalkyl, hetero$(C_{5-10})$cycloalkyl, $(C_{6-10})$aryl, hetero$(C_{5-10})$aryl, $(C_{9-10})$bicycloaryl and hetero$(C_{8-10})$bicycloaryl contained within $R^3$, $R^{22}$, $R^{24}$ and $R^{26}$ may be substituted further with up to five substituents selected from a group consisting of $(C_{1-6})$alkyl, $(C_{1-6})$alkylidene, cyano, halo, nitro, halo-substituted $(C_{1-3})$alkyl, $-X^3NR^{16}R^{16}$, $-X^3NR^{16}C(O)OR^{16}$, $-X^3NR^{16}C(O)NR^{16}R^{16}$, $-X^3NR^{16}C(NR^{16})NR^{16}R^{16}$, $-X^3OR^{16}$, $-X^3SR^{16}$, $-X^3C(O)OR^{16}$, $-X^3C(O)NR^{16}R^{16}$, $-X^3S(O)_2NR^{16}R^{16}$, $-X^3P(O)(OR^8)OR^{16}$, $-X^3OR^{52}$, $-X^3CONR^8R^{52}$, $-X^3C(O)R^{16}$, $-X^3SO_2NR^8R^{52}$, $-X^3S(O)R^{17}$, $-X^3OP(O)(OR^8)OR^{16}$, $-X^3NR^{16}C(O)R^{17}$, $-X^3S(O)_2R^{17}$ and $-X^3C(O)R^{16}$, wherein:

$X^3$ is a bond or $(C_{1-6})$alkylene, $R^{52}$ represents $-CH_2CH_2-N(CH_2CH_2OH)_2$, $-CH(CH_3)CH_2N(CH_3)_2$, $-CH_2CH_2OH$, $-CH_2CH_2N(CH_3)_2$ or $-CH_2CN$, $R^{16}$ at each occurrence independently is selected from a group consisting of hydrogen, $(C_{1-3})$alkyl or halo-substituted $(C_{1-3})$alkyl and $R^{17}$ is $-(C_{1-3})$alkyl or halo-substituted $(C_{1-3})$alkyl; and or the N-oxide compounds, prodrug derivatives, protected derivatives, individual stereo isomers and mixtures of stereo isomers, or pharmaceutically acceptable salts thereof, with the proviso that only one of $R^3$, $R^{22}$, $R^{24}$ and $R^{26}$ represents a fused bicyclic ring structure.

20. The method of claim 19 wherein the disease is osteoporosis.

21. A method for treating a disease in an animal in which inhibition of a cysteine protease can prevent, inhibit or ameliorate the pathology and/or symptomatology of the disease, which method comprises administering to the animal a therapeutically effective amount of compound of claim 7 or an N-oxide compound or individual stereo isomers or mixtures of stereo isomers thereof; or a pharmaceutically acceptable salt thereof.

22. The method of claim 21 wherein the disease is osteoporosis.

23. The method of claim 22 wherein the animal is a human.

24. The method of claim 23 wherein the human is a post-menopausal woman.

25. The method of claim 24 wherein the cysteine protease is cathepsin K.

* * * * *